US008212019B2

(12) United States Patent
Lawrence et al.

(10) Patent No.: US 8,212,019 B2
(45) Date of Patent: Jul. 3, 2012

(54) NUCLEIC ACID SILENCING SEQUENCES

(75) Inventors: Jeanne B. Lawrence, Mapleville, RI (US); Lisa L. Hall, Sudbury, MA (US)

(73) Assignee: University of Massachusetts, Shrewsbury, MA (US)

( * ) Notice: Subject to any disclaimer, the term of this patent is extended or adjusted under 35 U.S.C. 154(b) by 155 days.

(21) Appl. No.: 12/512,964

(22) Filed: Jul. 30, 2009

(65) Prior Publication Data

US 2010/0160417 A1 Jun. 24, 2010

Related U.S. Application Data

(60) Provisional application No. 61/084,918, filed on Jul. 30, 2008.

(30) Foreign Application Priority Data

Jul. 30, 2009 (WO) ................ PCT/US2009/052318

(51) Int. Cl.

*C07H 21/04* (2006.01)
*A61K 48/00* (2006.01)
*A61K 35/00* (2006.01)
*C12N 15/85* (2006.01)

(52) U.S. Cl. ................... 536/24.5; 536/23.1; 536/24.31; 536/24.33; 514/44; 435/325; 424/93.1

(58) Field of Classification Search ........................ None
See application file for complete search history.

(56) References Cited

OTHER PUBLICATIONS

Migeon et al., European Journal of Human Genetics, 2008, published on-line Oct. 31, 2007, 16, 153-162.*

Lau et al., Am. J. Hum. Genet., 61, 1997, 1353-1361.*

Brockdorff and Duthie, "X Chromosome Inactivation and the Xist Gene," Cell. Mol. Life Sci., 1998, vol. 54, pp. 104-112.

Brown et al., "The Human Xist Gene: Analysis of a 17kb Inactive X-specific RNA That Contains Conserved Repeats and is Highly Localized Within the Nucleus," Cell, 1992, vol. 71, pp. 527-542.

Cathomen and Joung, "Zinc-finger Nucleases: The Next Generation Emerges," Molecular Therapy, Jun. 10, 2008, vol. 16(7), pp. 1200-1207.

Chow et ai., "Inducible XIST-dependent X-chromosome Inactivation in Human Somatic Cells is Reversible," *PNAS*, Jun. 12, 2007, 104(24), pp. 10104-10109.

Greene and Lowrey, "The Human Xist Gene Promoter Prevents Silencing o fan Integrated Reporter Gene," Blood, 2004, vol. 104 (11), Abstract #2114.

International Search Report and Written Opinion for PCT/US209/052318, mailed Apr. 30, 2010.

Porteus, "Mammalian Gene Targeting with Designed Zinc Finger Nucleases," Molecular Therapy, 2006, vol. 13(2), pp. 438-446.

Savarese et al., "Hematopoietic Precursor Cells Transiently Reestablish Permissiveness for X Inactivation," Molecular and Cellular Biology, 2006, vol. 26(19), pp. 7167-7177.

Hall et al., "An Ectopic Human XIST Gene can induce chromosome inactivation in postdifferentiation human HT-1080 cells," Proc Natl Acad Sci USA 99:8677-8682, 2002.

Moehle et al., "Targeted gene addition into a specified location in the human genome using designed zinc finger nucleases," Proc Natl Acad Sci USA 104:3055-3060, 2007.

* cited by examiner

*Primary Examiner* — Amy Bowman
(74) *Attorney, Agent, or Firm* — Fish & Richardson P.C.

(57) ABSTRACT

The present invention features compositions and methods for introducing, into cells, nucleic acids whose expression results in chromosomal silencing. The nucleic acids are targeted to specific chromosomal regions where they subsequently reduce the expression of deleterious genes, or cause the death of deleterious cells. Where the nucleic acid sequence is a silencing sequence, it may encode an Xist RNA or other non-coding, silencing RNA. Accordingly, the present invention features, inter alia, nucleic acid constructs that include a transgene (e.g., a silencing sequence encoding an Xist RNA or other non-coding RNA that silences a segment of a chromosome); first and second sequences that direct insertion of the silencing sequence into a targeted chromosome; and, optionally, a selectable marker.

13 Claims, 20 Drawing Sheets

```
   1 ccttcagttc ttaaagcgct gcaattcgct gctgcagcca tatttcttac tctctcgggg
  61 ctggaagctt cctgactgaa gatctctctg cacttggggt tctttctaga acatttctca
 121 gtcccccaac acccttatg gcgtatttct ttaaaaaaat cacctaaatt ccataaaata
 181 tttttttaaa ttctatactt tctcctagtg tcttcttgac acgtcctcca tattttttta
 241 aagaaagtat ttggaatatt ttgaggcaat ttttaatatt taaggaattt ttctttggaa
 301 tcatttttgg tgacatctct gtttttttgtg gatcagtttt ttactcttcc actctctttt
 361 ctatattttg cccatcgggg ctgcggatac ctggttttat tattttttct ttgcccaacg
 421 gggccgtgga tacctgcctt ttaattcttt tttattcgcc catcggggcc gcggatacct
 481 gctttttatt ttttttccct tagcccatcg gggtatcgga tacctgctga ttcccttccc
 541 ctctgaaccc ccaacactct ggcccatcgg ggtgacggat atctgctttt taaaaatttt
 601 cttttttttgg cccatcgggg cttcggatac ctgctttttt tttttttatt ttccttgccc
 661 atcgggggcct cggatacctg ctttaatttt tgtttttctg cccatcgggg ccgcggatac
 721 ctgctttgat tttttttttt catcgcccat cggtgctttt tatggatgaa aaaatgttgg
 781 ttttgtgggt tgttgcactc tctggaatat ctacactttt ttttgctgct gatcatttgg
 841 tggtgtgtga gtgtacctac cgctttggca gagaatgact ctgcagttaa gctaagggcg
 901 tgttcagatt gtggaggaaa agtggccgcc attttagact tgccgcataa ctcggcttag
 961 ggctagtcgt ttgtgctaag ttaaactagg gaggcaagat ggatgatagc aggtcaggca
1021 gaggaagtca tgtgcattgc atgagctaaa cctatctgaa tgaattgatt tggggcttgt
1081 taggagcttt gcgtgattgt tgtatcggga ggcagtaaga atcatctttt atcagtacaa
1141 gggactagtt aaaaatggaa ggttaggaaa gactaaggtg cagggcttaa aatggcgatt
1201 ttgacattgc ggcattgctc agcatggcgg gctgtgcttt gttaggttgt ccaaaatggc
1261 ggatccagtt ctgtcgcagt gttcaagtgg cgggaaggcc acatcatgat gggcgaggct
1321 ttgttaagtg gttagcatgg tggtggacat gtgcggtcac acaggaaaag atggcggctg
1381 aaggtcttgc cgcagtgtaa aacatggcgg gcctctttgt ctttgctgtg tgcttttcgt
1441 gttgggtttt gccgcaggga caatatggca ggcgttgtca tatgtatatc atggcttttg
1501 tcacgtggac atcatggcgg gcttgccgca ttgttaaaga tggcgggttt tgccgcctag
1561 tgccacgcag agcgggagaa aaggtgggat ggacagtgct ggattgctgc ataacccaac
1621 caattagaaa tgggggtgga attgatcaca gccaattaga gcagaagatg gaattagact
1681 gatgacacac tgtccagcta ctcagcgaag acctgggtga attagcatgg cacttcgcag
1741 ctgtctttag ccagtcagga gaaagaagtg gaggggccac gtgtatgtct cccagtgggc
1801 ggtacaccag gtgttttcaa ggtcttttca aggacattta gcctttccac ctctgtcccc
1861 tcttatttgt cccctcctgt ccagtgctgc ctcttgcagt gctggatatc tggctgtgtg
1921 gtctgaacct ccctccattc ctctgtattg gtgcctcacc taaggctaag tatacctccc
1981 cccccacccc ccaacccccc caactcccca cccccacccc ccacccccca cctccccacc
2041 cccctacccc cctacccccc taccccccctc tggtctgccc tgcactgcac tgttgccatg
2101 ggcagtgctc caggcctgct tggtgtggac atggtggtga gccgtggcaa ggaccagaat
2161 ggatcacaga tgatcgttgg ccaacaggtg gcagaagagg aattcctgcc ttcctcaaga
2221 ggaacaccta ccccttggct aatgctgggg tcggattttg atttatattt atcttttgga
2281 tgtcagtcat acagtctgat tttgtggttt gctagtgttt gaatttaagt cttaagtgac
2341 tattatagaa atgtattaag aggctttatt tgtagaattc actttaatta catttaatga
2401 gtttttgttt tgagttcctt aaaattcctt aaagttttta gcttctcatt acaaattcct
2461 taaccttttt ttggcagtag atagtcaaag tcaaatcatt tctaatgttt taaaaatgtg
2521 ctggtcattt tctttgaaat tgacttaact attttccttt gaagagtctg tagcacagaa
2581 acagtaaaaa atttaacttc atgacctaat gtaaaaaaga gtgtttgaag gtttacacag
2641 gtccaggcct tgctttgttc ccatccttga tgctgcacta attgactaat cacctactta
2701 tcagacagga aacttgaatt gctgtggtct ggtgtcctct attcagactt attatattgg
2761 agtatttcaa tttttcgttg tatcctgcct gcctagcatc cagttcctcc ccagccctgc
2821 tcccagcaaa cccctagtct agccccagcc ctactcccac ccggccccag ccctgcccca
2881 ggcccagtcc cctaaccccc cagccctagg cccagtccca gtcctagttc ctcagtctgt
2941 ccagcttctc tcgaaagtca ctctaatttt cattgattca gtgctcaaaa taagttgtcc
3001 attggtatcc tattatactg ggatattccg tttacccttg gcattgctga tcttcagtac
3061 tgactccttg accattttca gttaagcata caatcccatt tgtctgtgat ctcaggacaa
3121 agaatttcct tactcggtac gttgaagtta gggaatgtca attgagagct ttctatcaga
3181 gcattattgc ccacaatttg agttacttat cattttctcg atcccctgcc cttaaaggag
3241 aaaccatttc tctgtcattg cttctgtagt cacagtccca atttgagta gtgatctttt
```

FIG. 6A

```
3301 cttgtgtact gtgttggcca cctaaaactc tttgcattga gtaaaattct aattgccaat
3361 aatcctaccc attggattag acagcactct gaaccccatt tgcattcagc aggggggtcgc
3421 agacaacccg tcttttgttg gacagttaaa atgctcagtc ccaattgtca tagctttgcc
3481 tattaaacaa aggcacccta ctgcgctttt tgctgtgctt ctggagaatc ctgctgttct
3541 tggacaatta aagaacaaag tagtaattgc taattgtctc acccattaat catgaagact
3601 accagtcgcc cttgcatttg ccttgaggca gcgctgacta cctgagattt aagagtttct
3661 taaattattg agtaaaatcc caattatcca tagttctgtt agttacacta tggcctttgc
3721 aaacatcttt gcataacagc agtgggactg actcattctt agagcccctt cccttggaat
3781 attaatggat acaatagtaa ttattcatgg ttctgcgtaa cagagaagac ccacttatgt
3841 gtatgccttt atcattgctc ctagatagtg tgaactacct accaccttgc attaatatgt
3901 aaaacactaa ttgcccatag tcccactcat tagtctagga tgtcctcttt gccattgctg
3961 ctgagttctg actacccaag tttccttctc ttaaacagtt gatatgcata attgcatata
4021 ttcatggttc tgtgcaataa aatggattc tcaccccatc ccaccttctg tgggatgttg
4081 ctaacgagtg cagattattc aataacagct cttgaacagt taatttgcac agttgcaatt
4141 gtccagagtc ctgtccatta gaaagggact ctgtatccta tttgcacgct acaatgtggg
4201 ctgatcaccc aaggactctt cttgtgcatt gatgttcata attgtatttg tccacgatct
4261 tgtgcactaa cccttccact ccctttgtat tccagcaggg gacccttact actcaagacc
4321 tctgtactag gacagtttat gtgcacaatc ctaattgatt agaactgagt cttttatatc
4381 aaggtccctg catcatcttt gctttacatc aagaggtgc tggttaccta atgcccctcc
4441 tccagaaatt attgatgtgc aaaatgcaat ttccctatct gctgttagtc tggggtctca
4501 tcccctcata ttcctttgt cttacagcag gggtacttg ggactgttaa tgcgcataat
4561 tgcaattatg gtcttttcca ttaaattaag atcccaactg ctcacaccct cttagcatta
4621 cagtagaggg tgctaatcac aaggacattt cttttgtact gttaatgtgc tacttgcatt
4681 tgtccctctt cctgtgcact aaagacccca ctcacttccc tagtgttcag cagtggatga
4741 cctctagtca agacctttgc actaggatag ttaatgtgaa ccatggcaac tgatcacaac
4801 aatgtctttc agatcagatc cattttatcc tccttgtttt acagcaaggg atattaatta
4861 cctatgttac ctttccctgg gactatgaat gtgcaaaatt ccaatgttca tggtctctcc
4921 ctttaaacct atattctacc ccttttacat tatagaaagg gatgctggaa acccagagtc
4981 cttctcttgg gactcttaat gtgtatttct aattatccat gactcttaat gtgcatattt
5041 tcaattgcct aattgatttc aattgtctaa gacatttcaa atgtctaatt gattagaact
5101 gagtctttta tatcaagcta atatctagct tttatatcaa gctaatatct tgacttctca
5161 gcatcataga agggggtact gatttcctaa agtctttctt gaatttctat tatgcaaaat
5221 tgccctgagg ccgggtgtgg tggctcacac ctgtaatccc agcactttgg gaggctgagg
5281 tgggaagatc ccttactgcc aggagtttga gaccagcctg gccaacatta aaaaaaaaaa
5341 aaaaagtaag acaattgccc tggaatccca tccccctcac acctccttgg caaagcagca
5401 ggagtgctaa ctagctagtg cttcttctct tatactgctt aaatgcgcat aattagcagt
5461 agttgatgtg cccctatgtt agagtagaat cccgcttcct tgctccattt gcattactgc
5521 aggagcttct aactagcctg aattcactct cttggactgt taatgtgcat acttatattt
5581 gctgctgtac tttttacca tgtaaggacc ccacccactg tatttacatc ccagctggaa
5641 gtacctacta cttaagaccc ttagactagt aaagttagcg tgcataatct taggtgttat
5701 atacacattt tcagttgcat acagttgtgc cttttatcag gactcctgta cttatcaaag
5761 cagagagtgc taatcaatat taagcccttc tcttcgaact gtagatggca tgtaattgca
5821 gttgtcaatg gtccttcaat tagacttggg tttctgacct atcacaccct ctttgcttta
5881 ttgcatgggg tactattcac ttaaggcccc tttctcaaac tgttaatgtg cctaatgaca
5941 attacatcag tatccttcct tttgaaggac agcatggttg gtgacaccta aggccccatt
6001 tcttggcctc ccaatatgtg tgattgtatt tgtcgaggtt gctatgcact agagaaggaa
6061 agtgctcccc tcatccccac ttttcccttc cagcaggaag tgcccacccc ataagaccct
6121 tttatttgga gagtctaggt gcacaattgt aagtgaccac aagcatgcat cttggacatt
6181 tatgtgcgta atcgcacact gctcattcca tgtgaataag gtcctactct ccgacccctt
6241 ttgcaataca gaagggttgc tgataacgca gtcccctttt cttggcatgt tgtgtgtgat
6301 tataatcgtc tgggatccta tgcactagaa aaggagggtc ctctccacat acctcagtct
6361 cacctttccc ttccagcagg gagtgcccac tccataagac tctcacattt ggacagtcaa
6421 ggtgcgtaat tgttaagtga acacaaccat gcaccttaga catggatttg cataactaca
6481 cacagctcaa cctatctgaa taaaatccta ctctcagacc ccttttgcag tacagcaggg
6541 gtgctgatca ccaaggccct ttttcctggc ctggtatgcg tgtgattatg tttgtcccgg
```

FIG. 6B

```
6601 ttcctgtgta ttagacatgg aagcctcccc tgccacactc cacccccaat cttcctttcc
6661 cttccggcag gagtgccctc tccataagac gcttacgttt ggacaatcaa ggtgcacagt
6721 tgtaagtgac cacaggcata caccttggac attaatgtgc ataaccactt tgcccattcc
6781 atctgaataa ggtcctactc tcagacccct tttgcagtac agcaggggtg ctgatcacca
6841 aggccccttt tcttggcctg ttatgtgcgt gattatattt gtctgggttc ctgtgtatta
6901 gacaaggaag ccttcccccc gcccccaccc ccactcccag tcttcctttc ccttccagca
6961 gggagtgccc cctccataag atcattacat ttggacaatc aaggtgcaca attataagtg
7021 accacagcca tgcaccttgg acattattgg acattaatgt gcgtaactgc acatggccca
7081 tcccatctga ataaggacct actctcagat gcctttgcag tacagcaggg gtactgaatc
7141 accaaggccc tttttcttgg cctgttatgt gtgtgattat atttatccca gtttctgtgt
7201 aatagacatg aaagcctccc ctgccacacc ccacctccaa tcttcctttc ccttccacca
7261 gggagtgtcc actccatata cccttacatt tggacaatca aggtgcacaa ttgtaagtga
7321 gcataggcac tcaccttgga catgaatgtg cataactgca catggcccat cccatctgaa
7381 taaggtccta ctctcagacc ctttttgcag tacagcaggg gtgctgatca ccaaggcccc
7441 ttttcctggc ctgttatgtg tgtgattata tttgttccag ttcctgtgta atagacatgg
7501 aagcctcccc tgccacactc cacccccaat cttcctttcc ttctggcagg aagtacccgc
7561 tccataagac ccttacattt ggacagtcaa ggtgcacaat tgtatgtgac cacaaccatg
7621 caccttggac ataaatgtgt gtaactgcac atggcccatc ccatctgaat aaggtcctac
7681 tctcagaccc cttttgcagt acagtaggtg tgctgataac caaggcccct cttcctggcc
7741 tgttaacgta tgtgattata tttgtctggg ttccagtgta taagacatgg aagcctcccc
7801 tgccccaccc caccctcaat cttcctttcc cttctggcag ggagtgccag ctccataaga
7861 accttacatt tggacagtca aggtgcacaa ttctaagtga ccgcagccat gcaccttggt
7921 caataatgtg tgtaactgca cacggcctat ctcatctgaa taaggcctta ctctcagacc
7981 ccttttgcag tacagcaggg gtgctgataa ccaaggccca ttttcctggc ctgttatgtg
8041 tgtgattata tttgtccagg tttctgtgta ctagacaagg aagcctcctc tgccccatcc
8101 catctacgca taatctttct tttcctccca gcagggagtg ctcactccat aagaccctta
8161 catttggaca atcaaggtgc acaattgtaa gtgaccacaa ccatgcatct tggaaattta
8221 tgtgcataac tgcacatggc ttatcctatt tgaataaagt cctactctca gacccccttt
8281 gcagtatagc tggggtgctg atcactgagg cctctttgct tggcttgtct atattcttgt
8341 gtactagata agggcacctt ctcatggact ccctttgctt ttcaacaagg agtacccact
8401 actttttaag attcttatat ttgtccaaag tacatggttt taattgacca caacaatgtc
8461 ccttggacat taatgtatgt aatcaccaca tggttcatcc taattaaaca aagttctacc
8521 ttctcaccct ccatttgcag tataccaggg ttgctgaccc cctaagtccc cttttcttgg
8581 cttgttgaca tgcataattg catttatgtt ggttcttgtg ccctagacaa ggatgcccca
8641 cctcttttca atagtgggtg cccactcctt atgatcttta catttgaaca gttaatgtga
8701 ataattgcag ttgtccacaa ccctatcact tctaggacca ttatacctct tttgcattac
8761 tgtggggtat actgtttccc tccaaggccc cttctggtgg actatcaaca tataattgaa
8821 attttctttt gtctttgtca gtagattaag gtcatacccc atcacctttc ctttgtagta
8881 caacagggtg tcctgatcaa ccaaagtcct gttgttttgg actgttaata tgtgcaatta
8941 catttgctcc tgatctgtgc actagataag gatcctacct actttcttag tgtttttagc
9001 aggtagtgcc cactactcaa gactgtcact tggaatgttc atgtgcacaa actcaattct
9061 ctaagcatgt tcctgtacca cctttgcttt agagcagggg gatgatattc actaagtgcc
9121 ccttcttttg gacttaatat gcattaatgc aattgtccac ctcttctttt agactaagag
9181 ttgatctcca catattcccc ttgcatcagg ggcatgttaa ttatgaatga acccttttct
9241 tttaatatta atgtcataat tgtatttgtg gacctgtgta ggagaaaaag accctatgtt
9301 cctcccatta ccctttggat tgctgctgag aagtgttaac tactcataat ctcagctctt
9361 ggacaattaa tagcattaat aacaattatc aagggcactg atcattagat aagactcctg
9421 cttcctcgtt gcttacatcg gggtactga cccactaagg ccccttgtac tgttaatgtg
9481 aatatttgca attatatatg tctccttctg gtagagtggg atattatgcc ctagtatccc
9541 ctttgcatta ctgcaggggc tgctgactac tcaaaacttc tcctgggact gttaataggc
9601 acaatggcag ttatcaatgg ttttctccct ccctgacctt gttaagcaag cgccccaccc
9661 caccccttagt ttcccatggc ataataaagt ataagcattg gagtattcca tgcacttgtc
9721 tatcaaacag tggtccatac tcccaaccct tttgcattgc gccagtgtgt aaaatcacag
9781 gtagccatgg tgtcatgctt tatatacgaa gtcttccctc tctctgcccc ttgtgtgccc
9841 ttggcccctt tttacagact attgctcaca atctcaggtg tccatatttg cagctattag
```

FIG. 6C

```
 9901 gtaagattgt gctgtctccc tcttcccttc cctctgccct gccccttttg cctctttgct
 9961 gggtaatgtt gaccagacaa ggccctttct cttggactta aacaattctc agttgcactt
10021 tccttggtcc acccattata catgaacccc tctacttcct ttcgcattgc ttctgagtat
10081 gctgactacc caaagcccct tctgtgttat taataaacac agtactgatt gtcccatttt
10141 tcagcccatc agtccaagat ctccctacca ctttggtgtg ttggtgcagt gttgactatg
10201 aaaagcaggc ctgaactagg tggataagcc ttcactcatt ttctttcatt tattaatgat
10261 cctagtttca attattgtca gattctgggg acaagaacca ttcttgccca cctgtgttac
10321 tgctttactg tgcaaaatac tgaaggcaag tcagacccag ggagctggat tgccatcctt
10381 tattttgtgt ttccagtgta cactataaaa ttgtctcccc aggaaggaag gttggcactt
10441 tctctgcatt cttctttcca gagcagattg cctggttaag aatctcttgt tgtcccttct
10501 gtatattgtt attgtaaagt gccaaatgcc aggatacagc cagaaaaatt gcttattatt
10561 attaaaaaaa tttttttaag aaagacatct ggattgtagg gtggactcga taacctggtc
10621 attatttttt tgaagccaaa atatccattt atactatgta cctggtgacc agtgtctctc
10681 attttaactg agggtggtgg gtctgtggat agaacactga ctcttgctat tttaatatca
10741 aagatattct agagtggaac tcttaagacc agtatctttg tgtgggcttt accagcattc
10801 acttttagaa aaactaccta aattttataa tcctttaatt tcttcatctg gagcacctgc
10861 ccctacttat ttcaagaaga ttgcagtaaa acgattaaat gagggaacat atgcagaggt
10921 gcttttaaaa agcatatgcc accttttta ttaattatta tataaaatga agcatttaat
10981 tatagtaata atttgaagta gtttgaagta ccacactgag gtgaggactt aaaaatgata
11041 agacgagttc cctattttat aagaaaaata agccaaaatt aaatattctt ttggatataa
11101 atttcaacag tgagatagct gcctagtgga aatgaataat atcccagcca ctagtgtaca
11161 gggtgttttg tggcacagga ttatgtaata tggaactgct caagcaaata actagtcatc
11221 acaacagcag ttctttgtaa taactgaaaa agaatattgt ttctcggaga aggatgtcaa
11281 aagatcggcc cagctcaggg agcagtttgc cctactagct cctcggacag ctgtaaagaa
11341 gagtctctgg ctctttagaa tactgatccc attgaagata ccacgctgca tgtgtcctta
11401 gtagtcatgt ctccttaggc tcctcttgga cattctgagc atgtgagacc tgaggactgc
11461 aaacagctat aagaggctcc aaattaatca tatctttccc tttgagaatc tggccaagct
11521 ccagctaatc tacttggatg ggttgccagc tatctggaga aaaagatctt cctcagaaga
11581 ataggcttgt tgttttacag tgttagtgat ccattccctt tgacgatccc taggtggaga
11641 tggggcatga ggatcctcca ggggaaaagc tcactaccac tgggcaacaa ccctaggtca
11701 ggaggttctg tcaagatact ttcctggtcc cagataggaa gataaagtct caaaaacaac
11761 caccacacgt caagctcttc attgttccta tctgccaaat cattatactt cctacaagca
11821 gtgcagagag ctgagtcttc agcaggtcca agaaatttga acacactgaa ggaagtcagc
11881 cttcccacct gaagatcaac atgcctggca ctctagcact tgaggatagc tgaatgaatg
11941 tgtatttctt tgtctctttc tttcttgtct ttgctctttg ttctctatct aaagtgtgtc
12001 ttacccattt ccatgtttct cttgctaatt tctttcgtgt gtgcctttgc ctcatttctt
12061 ctttttgttc acaagagtgg tctgtgtctt gtcttagaca tatctctcat ttttcatttt
12121 gttgctattt ctctttgctc tcctagatgt ggctcttctt tcacgcttta tttcatgtct
12181 ccttttttggg tcacatgctg tgtgcttttt gtccttttct tgttctgtct acctctcctt
12241 tctctgccta cctctctttt ctctttgtga actgtgatta tttgttaccc cttccccttc
12301 tcgttcgttt taaatttcac ctttttttctg agtctggcct cctttctgct gtttctactt
12361 tttatctcac atttctcatt tctgcatttc ctttctgcct ctcttgggct attctctctc
12421 tcctcccctg cgtgcctcag catctcttgc tgtttgtgat tttctatttc agtattaatc
12481 tctgttggct tgtatttgtt ctctgcttct tccctttcta ctcacctttg agtatttcag
12541 cctcttcatg aatctatctc cctctctttg atttcatgta atctctcctt aaatatttct
12601 ttgcatatgt gggcaagtgt acgtgtgtgt gtgtcatgtg tggcagaggg gcttcctaac
12661 ccctgcctga taggtgcaga acgtcggcta tcagagcaag cattgtggag cggttcctta
12721 tgccaggctg ccatgtgaga tgatccaaga ccaaaacaag gccctagact gcagtaaaac
12781 ccagaactca agtagggcag aaggtggaag gctcatatgg atagaaggcc caaagtataa
12841 gacagatggt ttgagacttg agacccgagg actaagatgg aaagcccatg ttccaagata
12901 gatagaagcc tcaggcctga aaccaacaaa agcctcaaga gccaagaaaa cagagggtgg
12961 cctgaattgg accgaaggcc tgagttggat ggaagtctca aggcttgagt tagaagtctt
13021 aagacctggg acaggacaca tggaaggcct aagaactgag acttgtgaca caaggccaac
13081 gacctaagat tagcccaggg ttgtagctgg aagacctaca acccaaggat ggaaggcccc
13141 tgtcacaaag cctacctaga tggatagagg acccaagcga aaaaggtatc tcaagactaa
```

FIG. 6D

```
13201 cggccggaat ctggaggccc atgacccaga acccaggaag gatagaagct tgaagacctg
13261 gggaaatccc aagatgagaa ccctaaaccc tacctctttt ctattgttta cacttcttac
13321 tcttagatat ttccagttct cctgtttatc tttaagcctg attcttttga gatgtacttt
13381 ttgatgttgc cggttacctt tagattgaca gtattatgcc tgggccagtc ttgagccagc
13441 tttaaatcac agcttttacc tatttgttag gctatagtgt tttgtaaact tctgtttcta
13501 ttcacatctt ctccacttga gagagacacc aaaatccagt cagtatctaa tctggctttt
13561 gttaacttcc ctcaggagca gacattcata taggtgatac tgtatttcag tcctttcttt
13621 tgaccccaga agccctagac tgagaagata aaatggtcag gttgttgggg aaaaaaaaag
13681 tgccaggctc tctagagaaa aatgtgaaga gatgctccag gccaatgaga agaattagac
13741 aagaaataca cagatgtgcc agacttctga gaagcacctg ccagcaacag cttccttctt
13801 tgagcttagg tgagcaggat tctggggttt gggatttcta gtgatggtta tggaaagggt
13861 gactgtgcct gggacaaagc gaggtcccaa ggggacagcc tgaactccct gctcatagta
13921 gtggccaaat aatttggtgg actgtgccaa cgctactcct gggtttaata cccatctcta
13981 ggcttaaaga tgagagaacc tgggactgtt gagcatgttt aatactttcc ttgatttttt
14041 tcttcctgtt tatgtgggaa gttgatttaa atgactgata atgtgtatga aagcactgta
14101 aaacataaga gaaaaaccaa ttagtgtatt ggcaatcatg cagttaacat ttgaaagtgc
14161 agtgtaaatt gtgaagcatt atgtaaatca ggggtccaca gtttttctgt aaggggtcaa
14221 atcataaata ctttagactg tgggccatat ggtttctgtt acatatttgt tttttaaaca
14281 acgtttttat aaggtcaaaa tcattcttag tttttgagcc aattggattt ggcctgctgt
14341 tcatagctta ccaccccctg atgtattatt tgttattcag agaaaatttc tgaatactac
14401 tagtttcctt ttctgtgcct gtccctgtgc taggcactaa aaatgcaatg attattgata
14461 tctaggtgac ctgaaaaaaa atagtgaatg tgctttgtaa actgtaaagc acttgtattc
14521 tactgtgata agcgttgtgg atacaaagaa aggagcaagc ataaaaaagt gctctttcaa
14581 aaggatatag tactatgcag acacaaggaa ttgtttgata aatgaataaa ttatatgtat
14641 atttgaggcc aatttgtgtt tgctgctctg gtaattttga gtaaaaatgc agtattccag
14701 gtatcagaaa cgaaaacaca tggaaactgc ttttaaactt taaaatatac tgaaaacata
14761 agggactaag cttgttgtgg tcacctataa tgtgccagat accatgctgg gtgctagagc
14821 taccaaaggg ggaaaagtat tctcatagca acaaaaaatt tcagaaaggt gcatattaaa
14881 gtgctttgta aactaaagca tgatacaaat gtcaatgggc tacatattta tgaatgaatg
14941 aatggatgaa tgaatattaa gtgcctctta cataccagct atttgggta ctgtaaaata
15001 caagattaat tctcctatgt aataagagga aagtttatcc tctatactat tcagatgtaa
15061 ggaatgatat attgcttaat tttaaacaat caagacttta ctggtgaggt taagttaaat
15121 tattactgat acatttttcc aggtaaccag gaaagagcta gtatgaggaa atgaagtaat
15181 agatgtgaga tccagaccga aagtcactta attcagcttg cgaatgtgct ttctaaatta
15241 taaagcactt gtaaatgaaa aatttgatgc tttctgtatg aataaaactt tctgtaagct
15301 aggtattgtc tctacaaaat tctcattgta tagttaaacc acagtgagaa gggttctata
15361 agtagttata caaaccaagg gtttaaatac ctgttaaata gatcaatttt gattgcctac
15421 tatgtgaact cactgttaaa ggcactgaaa atttatcata tttcatttag ccacagccaa
15481 aaataaggca atacctatgt tagcattttg tgaactctaa ggcaccatat aaatgtaact
15541 gttgattttc tcacttggtg ctgggtacta ggtttataaa attgtatgat agttattata
15601 ttgtgcaaat aaagtaggaa aatttgaata acaatgatta tcttttgaat acgcatacgc
15661 aagggattgg ttgtctgaag aatgccacta tagtagttat ctattgtgtg ccaatctcat
15721 tgctaggcat tggggatgca aagataaacc atctttattg tgtcttgggt agcagaagaa
15781 aatatgtgta aaatcaattt ataatttgta aactgccacc catatataag ctatatctgc
15841 tgaatgatca ttgattactc ttatccttag agataacaac tggggcaca aacatttatt
15901 atcattattg aacctacaac agagatctat gtgtagattt acgaagccta cagttctata
15961 cagataggaa tgaactattg gcttactgaa tggtgattac tttctgtggg gctcggaact
16021 acatgcccta ggatataaaa atgatgttat cattatagag tgctcacaga aggaaatgaa
16081 gtaatatagg tgtgagatcc agaccaaaag ttatttaaca agtttattca gtgatgaaaa
16141 catgggacaa atggactata taaggcagtg tactaagctg agtagagaga taaagtcctg
16201 tccagaagat acatgctttc ctggcctgat tgaggagatg gaaaattttt gcaaaaaaca
16261 aggtgtttgt ggtcttccat ccagtttctt aagtgctgat gataaaagtg aattagaccc
16321 accttgacct ggcctacaga agtaaaggag taaaaataaa tgcctcaggc gtgcttttg
16381 attcatttga taaacaaagc atcttttatg tggaatatac cattctgggt cctgaggata
16441 agagagatga gggcattaga tcactgacag ctgaagatag a  (SEQ ID NO:1)
```

FIG. 6E

```
   1 cttcagttct taaagcgctg caattcgctg ctgcagccat atttcttact ctctcggggc
  61 tggaagcttc ctgactgaag atctctctgc acttggggtt ctttctagaa cattttctag
 121 tcccccaaca ccctttatgg cgtatttctt taaaaaaatc acctaaattc cataaaatat
 181 tttttaaat tctatacttt ctcctagtgt cttcttgaca cgtcctccat atttttttaa
 241 agaaagtatt tggaatattt tgaggcaatt tttaatattt aaggaatttt tctttggaat
 301 catttttggt tgacatctct gtttttgtg gatcagtttt ttactcttcc actctctttt
 361 ctatatttg cccatcgggg ctgcggatac ctggttttat tattttttct ttgcccaacg
 421 gggccgtgga tacctgcctt ttaattcttt tttattcgcc catcggggcc gcggatacct
 481 gctttttatt ttttttcct tagcccatcg gggtatcgga tacctgctga ttcccttccc
 541 ctctgaaccc ccaacactct ggcccatcgg ggtgacggat atctgctttt taaaaatttt
 601 ctttttttgg cccatcgggg cttcggatac ctgctttttt ttttttttatt tttccttgcc
 661 catcggggcc tcggatacct gctttaattt ttgtttttct ggcccatcgg ggccgcggat
 721 acctgctttg atttttttt ttcatcgccc atcggtgctt tttatggatg aaaaaatgtt
 781 ggttttgtgg gttgttgcac tctctggaat atctacactt ttttttgctg ctgatcattt
 841 ggtggtgtgt gagtgtacct accgctttgg cagagaatga ctctgcagtt aagctaaggg
 901 cgtgttcaga ttgtggagga aaagtggccg ccattttaga cttgccgcat aactcggctt
 961 agggctagtc gtttgtgcta agttaaacta gggaggcaag atggatgata gcaggtcagg
1021 cagaggaagt catgtgcatt gcatgagcta aacctatctg aatgaattga tttggggctt
1081 gttaggagct ttgcgtgatt gttgtatcgg gaggcagtaa gaatcatctt ttatcagtac
1141 aagggactag ttaaaaatgg aaggttagga aagactaagg tgcagggctt aaaatggcga
1201 ttttgacatt gcggcattgc tcagcatggc gggctgtgct ttgttaggtt gtccaaaatg
1261 gcggatccag ttctgtcgca gtgttcaagt ggcgggaagg ccacatcatg atgggcgagg
1321 ctttgttaag tggttagcat ggtggtggac atgtgcggtc acacaggaaa agatggcggc
1381 tgaaggtctt gccgcagtgt aaaacatggc gggcctcttt gtctttgctg tgtgctttc
1441 gtgttgggtt ttgccgcagg gacaatatgg caggcgttgt catatgtata tcatggcttt
1501 tgtcacgtgg acatcatggc gggcttgccg cattgttaaa gatggcgggt tttgccgcct
1561 agtgccacgc agagcgggag aaaaggtggg atggacagtg ctggattgct gcataaccca
1621 accaattaga aatgggggtg gaattgatca cagccaatta gagcagaaga tggaattaga
1681 ctgatgacac actgtccagc tactcagcga agacctgggt gaattagcat ggcacttcgc
1741 agctgtcttt agccagtcag gagaaagaag tggagggcc acgtgtatgt ctcccagtgg
1801 gcggtacacc aggtgttttc aaggtctttt caaggacatt tagcctttcc acctctgtcc
1861 cctcttattt gtcccctcct gtccagtgct gcctcttgca gtgctggata tctggctgtg
1921 tggtctgaac ctccctccat tcctctgtat tggtgcctca cctaaggcta agtatacctc
1981 ccccccacc ccccaacccc cccaactccc caccccccacc ccccaccccc cacctcccca
2041 ccccctacc cccctacccc cctaccccc tctggtctgc cctgcactgc actgttgcca
2101 tgggcagtgc tccaggcctg cttggtgtgg acatggtggt gagccgtggc aaggaccaga
2161 atggatcaca gatgatcgtt ggccaacagg tggcagaaga ggaattcctg ccttcctcaa
2221 gaggaacacc taccccttgg ctaatgctgg ggtcggattt tgatttatat ttatcttttg
2281 gatgtcagtc atacagtctg attttgtggt ttgctagtgt ttgaatttaa gtcttaagtg
2341 actattatag aaatgtatta agaggcttta tttgtagaat tcactttaat tacatttaat
2401 gagtttttgt tttgagttcc ttaaaattcc ttaaagtttt tagcttctca ttacaaattc
2461 cttaaccttt ttttggcagt agatagtcaa agtcaaatca tttctaatgt tttaaaaatg
2521 tgctggtcat tttctttgaa attgacttaa ctattttcct ttgaagagtc tgtagcacag
2581 aaacagtaaa aaatttaact tcatgaccta atgtaaaaaa gagtgtttga aggtttacac
2641 aggtccaggc cttgctttgt tcccatcctt gatgctgcac taattgacta atcacctact
2701 tatcagacag gaaacttgaa ttgctgtggt ctggtgtcct ctattcagac ttattatatt
2761 ggagtatttc aatttttcgt tgtatcctgc ctgcctagca tccagttcct ccccagccct
2821 gctcccagca aaccccctagt ctagccccag ccctactccc accccgcccc agccctgccc
2881 cagccccagt cccctaaccc cccagcccta gccccagtcc cagtcctagt tcctcagtcc
2941 cgcccagctt ctctcgaaag tcactctaat tttcattgat tcagtgctca aaataagttg
3001 tccattgctt atcctattat actgggatat tccgtttacc cttggcattg ctgatcttca
3061 gtactgactc cttgaccatt ttcagttaat gcatacaatc ccatttgtct gtgatctcag
3121 gacaaagaat ttccttactc ggtacgttga agttagggaa tgtcaattga gagctttcta
3181 tcagagcatt attgcccaca atttgagtta cttatcattt tctcgatccc ctgcccttaa
3241 aggagaaacc atttctctgt cattgcttct gtagtcacag tcccaatttt gagtagtgat
```

FIG. 7A

```
3301 cttttcttgt gtactgtgtt ggccacctaa aactctttgc attgagtaaa attctaattg
3361 ccaataatcc tacccattgg attagacagc actctgaacc ccatttgcat tcagcagggg
3421 gtcgcagaca acccgtcttt tgttggacag ttaaaatgct cagtcccaat tgtcatagct
3481 ttgcctatta aacaaaggca ccctactgcg ctttttgctg tgcttctgga gaatcctgct
3541 gttcttggac aattaaagaa caaagtagta attgctaatt gtctcaccca ttaatcatga
3601 agactaccag tcgcccttgc atttgccttg aggcagcgct gactacctga gatttaagag
3661 tttcttaaat tattgagtaa aatcccaatt atccatagtt ctgttagtta cactatggcc
3721 tttgcaaaca tctttgcata acagcagtgg gactgactca ttcttagagc cccttccctt
3781 ggaatattaa tggatacaat agtaattatt catggttctg cgtaacagag aagacccact
3841 tatgtgtatg cctttatcat tgctcctaga tagtgtgaac tacctaccac cttgcattaa
3901 tatgtaaaac actaattgcc catagtccca ctcattagtc taggatgtcc tctttgccat
3961 tgctgctgag ttctgactac ccaagtttcc ttctcttaaa cagttgatat gcataattgc
4021 atatattcat ggttctgtgc aataaaaatg gattctcacc ccatcccacc ttctgtggga
4081 tgttgctaac gagtgcagat tattcaataa cagctcttga acagttaatt tgcacagttg
4141 caattgtcca gagtcctgtc cattagaaag ggactctgta tcctatttgc acgctacaat
4201 gtgggctgat cacccaagga ctcttcttgt gcattgatgt tcataattgt atttgtccac
4261 gatcttgtgc actaaccctt ccactccctt tgtattccag caggggaccc ttactactca
4321 agacctctgt actaggacag tttatgtgca caatcctaat tgattagaac tgagtctttt
4381 atatcaaggt ccctgcatca tctttgcttt acatcaagag ggtgctggtt acctaatgcc
4441 cctcctccag aaattattga tgtgcaaaat gcaatttccc tatctgctgt tagtctgggg
4501 tctcatcccc tcatattcct tttgtcttac agcagggggt acttgggact gttaatgcgc
4561 ataattgcaa ttatggtctt ttccattaaa ttaagatccc aactgctcac accctcttag
4621 cattacagta gagggtgcta atcacaagga catttctttt gtactgttaa tgtgctactt
4681 gcatttgtcc ctcttcctgt gcactaaaga ccccactcac ttccctagtg ttcagcagtg
4741 gatgacctct agtcaagacc tttgcactag gatagttaat gtgaaccatg gcaactgatc
4801 acaacaatgt ctttcagatc agatccattt tatcctcctt gttttacagc aagggatatt
4861 aattacctat gttacctttc cctgggacta tgaatgtgca aaattccaat gttcatggtc
4921 tctcccttta aacctatatt ctaccccttt tacattatag aaagggatgc tggaaaccca
4981 gagtccttct cttgggactc ttaatgtgta tttctaatta tccatgactc ttaatgtgca
5041 tattttcaat tgcctaattg atttcaattg tctaagacat ttcaaatgtc taattgatta
5101 gaactgagtc ttttatatca agctaatatc tagcttttat atcaagctaa tatcttgact
5161 tctcagcatc atagaagggg gtactgattt cctaaagtct ttcttgaatt tctattatgc
5221 aaaattgccc tgaggccggg tgtggtggct cacacctgta atcccagcac tttgggaggc
5281 tgaggtggga agatccctta ctgccaggag tttgagacca gcctggccaa cattaaaaaa
5341 aaaaaaaagt aagacaattg ccctggaatc ccatcccccct cacacctcct tggcaaagca
5401 gcaggagtgc taactagcta gtgcttcttc tcttatactg cttaaatgcg cataattagc
5461 agtagttgat gtgcccctat gttagagtag aatcccgctt ccttgctcca tttgcattac
5521 tgcaggagct tctaactagc ctgaattcac tctcttggac tgttaatgtg catacttata
5581 tttgctgctg tactttttta ccatgtaagg accccaccca ctgtatttac atcccagctg
5641 gaagtaccta ctacttaaga cccttagact agtaaagtta gcgtgcataa tcttaggtgt
5701 tatatacaca ttttcagttg catacagttg tgccttttat caggactcct gtacttatca
5761 aagcagagag tgctaatcaa tattaagccc ttctcttcga actgtagatg gcatgtaatt
5821 gcagttgtca atggtccttc aattagactt gggtttctga cctatcacac cctctttgct
5881 ttattgcatg gggtactatt cacttaaggc ccctttctca aactgttaat gtgcctaatg
5941 acaattacat cagtatcctt ccttttgaag gacagcatgg ttggtgacac ctaaggcccc
6001 atttcttggc ctcccaatat gtgtgattgt atttgtcgag gttgctatgc actagagaag
6061 gaaagtgctc ccctcatccc cacttttccc ttccagcagg aagtgcccac cccataagac
6121 ccttttattt ggagagtcta ggtgcacaat tgtaagtgac cacaagcatg catcttggac
6181 atttatgtgc gtaatcgcac actgctcatt ccatgtgaat aaggtcctac tctccgaccc
6241 cttttgcaat acagaagggt tgctgataac gcagtcccct tttcttggca tgttgtgtgt
6301 gattataatc gtctgggatc ctatgcacta gaaaaggagg gtcctctcca catacctcag
6361 tctcaccttt cccttccagc agggagtgcc cactccataa gactctcaca tttggacagt
6421 caaggtgcgt aattgttaag tgaacacaac catgcacctt agacatggat ttgcataact
6481 acacacagct caacctatct gaataaaatc ctactctcag accccttttg cagtacagca
6541 ggggtgctga tcaccaaggc ccttttttcct ggcctggtat gcgtgtgatt atgtttgtcc
```

FIG. 7B

```
6601 cggttcctgt gtattagaca tggaagcctc ccctgccaca ctccaccccc aatcttcctt
6661 tcccttccgg cagggagtgc cctctccata agacgcttac gtttggacaa tcaaggtgca
6721 cagttgtaag tgaccacagg catacacctt ggacattaat gtgcataacc actttgccca
6781 ttccatctga ataaggtcct actctcagac ccctttgca gtacagcagg ggtgctgatc
6841 accaaggccc cttttcttgg cctgttatgt gcgtgattat atttgtctgg gttcctgtgt
6901 attagacaag gaagccttcc ccccgccccc acccccactc ccagtcttcc tttcccttcc
6961 agcagggagt gccccctcca taagatcatt acatttggac aatcaaggtg cacaattata
7021 agtgaccaca gccatgcacc ttggacatta ttggacatta atgtgcgtaa ctgcacatgg
7081 cccatcccat ctgaataagg tcctactctc agatgccctt tgcagtacag caggggtact
7141 gaatcaccaa ggcccttttt cttggcctgt tatgtgtgtg attatattta tcccagtttc
7201 tgtgtaatag acatgaaagc ctcccctgcc acaccccacc tccaatcttc ctttcccttc
7261 caccagggag tgtccactcc atataccctt acatttggac aatcaaggtg cacaattgta
7321 agtgagcata ggcactcacc ttggacatga atgtgcataa ctgcacatgg cccatcccat
7381 ctgaataagg tcctactctc agaccctttt tgcagtacag caggggtgct gatcaccaag
7441 gcccctttc ctggcctgtt atgtgtgtga ttatatttgt tccagttcct gtgtaataga
7501 catggaagcc tcccctgcca cactccaccc ccaatcttcc tttcccttct ggcaggaagt
7561 acccgctcca taagaccctt acatttggac agtcaaggtg cacaattgta tgtgaccaca
7621 accatgcacc ttggacataa atgtgtgtaa ctgcacatgg cccatcccat ctgaataagg
7681 tcctactctc agacccctt tgcagtacag taggtgtgct gataaccaag gcccctcttc
7741 ctggcctgtt aacgtatgtg attatatttg tctgggttcc agtgtataag acatggaagc
7801 ctcccctgcc ccaccccacc ctcaatcttc ctttcccttc tggcagggag tgccagctcc
7861 ataagaacct tacatttgga cagtcaaggt gcacaattct aagtgaccgc agccatgcac
7921 cttggtcaat aatgtgtgta actgcacacg gcctatctca tctgaataag gccttactct
7981 cagacccctt ttgcagtaca gcaggggtgc tgataaccaa ggcccatttt cctggcctgt
8041 tatgtgtgtg attatatttg tccaggtttc tgtgtactag acaaggaagc ctcctctgcc
8101 ccatcccatc tacgcataat ctttcttttc ctcccagcag ggagtgctca ctccataaga
8161 cccttacatt tggacaatca aggtgcacaa ttgtaagtga ccacaaccat gcatcttgga
8221 aatttatgtg cataactgca catggcttat cctatttgaa taaagtccta ctctcagacc
8281 ccctttgcag tatagctggg gtgctgatca ctgaggcctc tttgcttggc ttgtctatat
8341 tcttgtgtac tagataaggg caccttctca tggactccct ttgcttttca acaaggagta
8401 cccactactt tttaagattc ttatatttgt ccaaagtaca tggttttaat tgaccacaac
8461 aatgtccctt ggacattaat gtatgtaatc accacatggt tcatcctaat taaacaaagt
8521 tctaccttct caccctccat ttgcagtata ccagggttgc tgacccccta agtccccttt
8581 tcttggcttg ttgacatgca taattgcatt tatgttggtt cttgtgccct agacaaggat
8641 gccccacctc ttttcaatag tgggtgccca ctccttatga tctttacatt tgaacagtta
8701 atgtgaataa ttgcagttgt ccacaaccct atcacttcta ggaccattat acctcttttg
8761 cattactgtg gggtatactg tttccctcca aggcccttc tggtggacta tcaacatata
8821 attgaaattt tcttttgtct ttgtcagtag attaaggtca taccccatca cctttccttt
8881 gtagtacaac agggtgtcct gatcaaccaa agtcctgttg ttttggactg ttaatatgtg
8941 caattacatt tgctcctgat ctgtgcacta gataaggatc ctacctactt tcttagtgtt
9001 tttagcaggt agtgcccact actcaagact gtcacttgga atgttcatgt gcacaaactc
9061 aattctctaa gcatgttcct gtaccacctt tgctttagag caggggggatg atattcacta
9121 agtgcccctt cttttggact taatatgcat taatgcaatt gtccacctct tcttttagac
9181 taagagttga tctccacata ttccccttgc atcaggggca tgttaattat gaatgaaccc
9241 ttttctttta atattaatgt cataattgta tttgtggacc tgtgtaggag aaaaagaccc
9301 tatgttcctc ccattaccct ttggattgct gctgagaagt gttaactact cataatctca
9361 gctcttggac aattaatagc attaataaca attatcaagg gcactgatca ttagataaga
9421 ctcctgcttc ctcgttgctt acatcggggg tactgaccca ctaaggcccc ttgtactgtt
9481 aatgtgaata tttgcaatta tatatgtctc cttctggtag agtgggatat tatgccctag
9541 tatccccttt gcattactgc aggggctgct gactactcaa aacttctcct gggactgtta
9601 ataggcacaa tggcagttat caatggtttt ctccctccct gaccttgtta agcaagcgcc
9661 ccaccccacc cttagtttcc catggcataa taaagtataa gcattggagt attccatgca
9721 cttgtctatc aaacagtggt ccatactccc aaccctttg cattgcgcca gtgtgtaaaa
9781 tcacaggtag ccatggtgtc atgctttata tacgaagtct tccctctctc tgccccttgt
9841 gtgcccttgg cccctttta cagactattg ctcacaatct caggtgtcca tatttgcagc
```

FIG. 7C

```
 9901 tattaggtaa gattgtgctg tctccctctt cccttccctc tgccctgccc cttttgcctc
 9961 tttgctgggt aatgttgacc agacaaggcc ctttctcttg gacttaaaca attctcagtt
10021 gcactttcct tggtcccacc cattatacat gaacccctct acttcctttc gcattgcttc
10081 tgagtatgct gactacccaa agccccttct gtgttattaa taaacacagt actgattgtc
10141 ccatttttca gcccatcagt ccaagatctc cctaccactt tggtgtgttg gtgcagtgtt
10201 gactatgaaa agcaggcctg aactaggtgg ataagccttc actcattttc tttcatttat
10261 taatgatcct agtttcaatt attgtcagat tctggggaca agaaccattc ttgcccacct
10321 gtgttactgc tttactgtgc aaaatactga aggcaagtca gacccaggga gctggattgc
10381 catcctttat tttgtgtttc cagtgtacac tataaaattg tctccccagg aaggaaggtt
10441 ggcactttct ctgcattctt ctttccagag cagattgcct ggttaagaat ctcttgttgt
10501 ccccttttgta tattgttatt gtaaagtgcc aaatgccagg atacagccag aaaaattgct
10561 tattattatt aaaaaaattt ttttaagaaa gacatctgga ttgtagggtg gactcgataa
10621 cctggtcatt atttttttga agccaaaata tccatttata ctatgtacct ggtgaccagt
10681 gtctctcatt ttaactgagg gtggtgggtc tgtggataga acactgactc ttgctatttt
10741 aatatcaaag atattctaga gtggaactct taagaccagt atctttgtgt gggctttacc
10801 agcattcact tttagaaaaa ctacctaaat tttataatcc tttaatttct tcatctggag
10861 cacctgcccc tacttatttc aagaagattg cagtaaaacg attaaatgag ggaacatatg
10921 cagaggtgct tttaaaaagc atatgccacc tttttattta attattatat aaaatgaagc
10981 atttaattat agtaataatt tgaagtagtt tgaagtacca cactgaggtg aggacttaaa
11041 aatgataaga cgagttccct attttataag aaaaataagc caaaattaaa tattcttttg
11101 gatataaatt tcaacagtga gatagctgcc tagtggaaat gaataatatc ccagccacta
11161 gtgtacaggg tgttttgtgg cacaggatta tgtaatatgg aactgctcaa gcaaataact
11221 agtcatcaca acagcagttc tttgtaataa ctgaaaaaga atattgtttc tcggagaagg
11281 atgtcaaaag atcggcccag ctcagggagc agtttgccct actagctcct cggacagctg
11341 taaagaagag tctctggctc tttagaatac tgtaagtact acttcgtagc tattaagtaa
11401 tctttttcct attctatttt ctttctctta gatgccacct atagaaaagt cagagggtcc
11461 agtaagtttc tttccttctt cccacctcat ctgcaatata tatatataga gagagaaata
11521 gatacataca tacatgcata aatacacata tgtgagttaa ccagcagaac tgtagaatta
11581 atattgtgga cccagctcta tgctaggtta cactgataac ctgggtagga atgatatcat
11641 cctatataat ttcattcctg agatgatttt atcgttgagg agctaatgtg agcacatttg
11701 aaataacttt agaaaataat aagtgctgtt ttgtgtgaat cataagtagt agttttagga
11761 agggaaccca caaggatttg aagttgatag aataaactta aggaagtggg tttgcttttt
11821 ctctttaagc caagatagga ttaatattgc agccatctgg atagtccagt tggtttattt
11881 taatttcatt tgtttttttac ctcttttgga gccatggaaa gagatgaaag ggatagagca
11941 tagccattgt gtttggctat ttgcgaaggt tggcaaatta gtgattgcta aatctcataa
12001 gcttgagtat tttaaagttc agagattgag ggcataaatc taatacttcg gctccttcca
12061 caattttact acatttctgc ccaagaacag atgaccatgg ataatgcata tcgtagatac
12121 tttttaagtt tggaaccttt ttgccaagag ggtagtggag aagtgaagtc aaaaccttga
12181 ccttccttgc ctactttatg ctgtagttta tataccttct ttcctcccac ctttcgtaaa
12241 gctaaaagaa gcttagcctc cttaatgttt tccagctgac aaaatattgt ttaacataac
12301 attcgaaact tttttctgg tgcacattca tgcatcacag caggagcaac aagaaccata
12361 taagtgaact ggcttcactt atagcccgtt ttaattcata tccatatttc ctcagggctt
12421 gtttccatgc ctcccagccc cactccatat gcttaacaac attgtctggc tgactgaggg
12481 ttatatacat catggtcttg aaccttcttg gaaacatggt ctgtgccatt gtttctcaaa
12541 cccaagtaat gcttcatgat gaaacacctt ctaaaggaac aaaatttct gagatcctaa
12601 aaaaatgtgt tttgaggaac actgacttaa caaagatatt tgaaatgtaa atatgttttc
12661 caatttcacg ttgtctttgt caaagatgtg ttttatataa cttatgtaga acttggggat
12721 ccattagaat atattcacaa atccccaggg ttatcacccc aatttgagaa accctggtct
12781 atgcttatga aatcttctat tggtaattaa attgtcattc attgtcaaca tacaattata
12841 attattattg gaatttgttt taaatgaatg aatttggagg tgattctgta ccttaagtca
12901 agaggaagga tggcttgatt ttaggtggat tgattatact agatagcatc caaaggtgaa
12961 tcttgaagct gtatttaaat tcattgcttg aaataatttc caccccttaag aaaaatctct
13021 agcaattgta aaaagggatg ctctggaaat gtgggcatct tcaaaataga gataattctt
13081 gtgttagttc aacaaatatt attgtaccag gtgctggaat aaatagcaaa accaaagaca
13141 ggatttatat caaggaattt gctttcttat ggaggatgca gaaggaaatc attatggttt
```

FIG. 7D

```
13201 tgggcagaaa tgcttagact ttagtcctgg ctctgagttt ggttcagatc accatcaatc
13261 tgaccatctc gagactgcta gtgaaataag ataggggctt atatcaaata cctaaatccc
13321 tgaaaatgac attttgtgat ttggaaaatt ttcaaaagtc taatgaagga aactttttg
13381 gcatttcttt aaatgattat tgtcatttct tttctgactt ttccctttat aaaaccttaa
13441 catgtaggat tggaggaagt tttctgacca ttttctcata tcctctttca gctttatctt
13501 tctgtaactt ccatttctct agccacctcc ctaaattaca gaagactgtg agacccaggg
13561 ctgctgtgat taggcattca taatttcttt tcagggtgtt tgtgccctga ttatcaaatg
13621 tacagcttga agggagttca tgtcttaaag taatgaatta agagttgacc tttgttgact
13681 gctaaaatat tcttatatgt gaaagcatcc tggaaaaata cgttaccagc ttaaagagaa
13741 agaaactaat gattatatct gaactgagct aatgcctctt ctcttccccc aaaccttatc
13801 agtttggatg gcaaagagta atgatgtgtc agttaaacag agctaatgcc ttcctctgcc
13861 ttgtcttaaa gactggattg ggagaaaatt gatattctca ctaccatatt ttgggctgta
13921 ggcaagtagc attttacaca ggtttccttc aaaaatccaa ctcaagttgg agctcatgta
13981 tttaagacat agctggcctg ctgaatttaa caagttaaac ttcagtggcc atgtacagtt
14041 atatatcact atatatatgt gtattaggct gtcgagttgg tcatgttttt gttggtgact
14101 taggctttac ttgatagctc ttccttgacc tttccaaatt gagtactgat acatggagct
14161 tgggcttctt ctgcatctta tacaaatgag tttggtaaag aagcctctcc tttactgttt
14221 tgatgtttat attagaaata acttttgatt atttttttc atgttaggat gagaaactga
14281 aacaaaatgt aaatttgacc ggtgctagac ttcttaaatt atgggtagac ttaaagtatt
14341 attttcctta accaattaga atgctagtct tctagtgttc ccggaaacat gagaggttat
14401 gcagtagacc caagcaatac cctcttatta cataatcaag tgcgtataag aatttaaaaa
14461 tagggatatg actggaacat cactgtactt taccaggtcc cattataaaa ttatctatgt
14521 tactttaccc atagctttga aaactagtgg catagtatat tttatagtat gctgttagtg
14581 tgattggcat tgaacagtga tgggatataa tcactctaca atctatatgt tattaaagtt
14641 ttccagcctt atagatctcc cttgactgaa aattagctac taacttacga cttatttttt
14701 acagcagatt gactaggtct ttccaggaaa tctgttgatg tacaaaaaca aagtttaatt
14761 gctaatgttt ttttaaaaaa taacttttg atattacgga tacctggtta tttgggcctt
14821 gtatatttta acatcaaaat tacctattat aaatccatat aaacagaaaa gaaagagagt
14881 aagtctttag atcagatctg caaacaatga tggtacgtac tgtagaaaaa tctggaacat
14941 agacttacca gttcttaggt tccattttgc ttgcttttta aaaactgtgt cttataagtc
15001 ttcagcaact ggttgggaga tttttagaaa aaataacctt ttaatgttag aacagtgtag
15061 agatttacag aatgattctg aagatagagt ttctgtgtac ttcacaccca gtttttccca
15121 gtgttaacat tttacattag tttggtacat ttgtcacaac aaaccaatat tgatacatta
15181 ttattaacta gagtccatat tttattcaga tttccttagt ttttccttaa tgttcttttt
15241 gtgttccagg atcccattga agataccacg ctgcatgtgt ccttagtagt catgtctcct
15301 taggctcctc ttggtaatga cagtttctca gactctttgt ttttgatgaa cttcacagtt
15361 ttgaggacta atggtccagt attctataga atgtctctct attggaattt gtctgatgtt
15421 cttctcatga ctagattggg tttatgagtg tttaggagga agaccacaaa ggtagagtgc
15481 cattcttatc acttatcaag agtacatact atcaacatga cttatcactg tttatgttat
15541 ccttaatcac ctgtctgagg tactatttgt caggtttctc cagcgtaaaa ttagtcttta
15601 tttctccatt tccctactat actgttcaca taggaagtca ctatgtgcag ccagcactta
15661 aggaatggga aattaccttc cacctcattg agggcagagt atttacataa attatttgga
15721 attcttttgc acaggatgtc ttttctccac aatgtattgt gtttattcag tcatttatat
15781 cagtatgatc tcagggatat tttatactct gggttataat acagtattac tttattctgt
15841 tgttcaaatt gttccagctt tggccattgg gaggtctttc atttggcttt gatataaccc
15901 catgaatgtg ggttttttgt ttgagcactt tcttattttt ggaactacaa catgcttcag
15961 actcatttgc atatctcctg cctggaccta aaatgatgta tttctgcaag gagccttgat
16021 actttttatt ggagagtaat attagaaatc aagaagtgaa tgctaggtgc gctcattact
16081 actggagtgt cattccttca agaccttttc agttgacaag agcaaggaga tatatatttg
16141 cattctaacg tgtgtatatg cacatagcta taaatatata taaccatctg tatctatatt
16201 aaactaaatg tgtttatacc tacgtctcca actctaatca ttgccacatg gatcattata
16261 gtctcacctc cttgcttatc tgttacctcc catttctaca gtgagaaacc tggcttggtt
16321 gggaaatttt tctgttaata ttacggtagt gagtgtttga catttgcttc tatggttaag
16381 tttagggaga gtttagctgt agggtattct tgaaactaga aatgaccctt ctgccctaaa
16441 tgtttctgcc agtttgaaa cgtaaaatag gttgcagaaa caaactttat cttaagaacc
```

FIG. 7E

```
16501 agaatttact tcaatccaca ttttgacatt gattttcaga ttaaattatt ctgatatcgc
16561 caggtaagct gttccttggg tatgcatttc ttctttccgt ttttttctaa gagctaaagg
16621 accctgagaa cactggaggt gggaaaggaa gggaaaggca tgttcacacg tgggatagga
16681 aaggttcatt tactgacctc cagctagcct tccaaagtgc ctatttaaga cccaaggagt
16741 agatgtcttc cttggcaatt gtaacccaaa tataattttt aacctttcaa ttttagtcaa
16801 gaaagttggt gtgctgttac aaaaagtgcc ctgattaaca gcattgtcat gtgcattgca
16861 tattaatcag caatttaaaa taacatgaaa ttatgttgag tataatttta atattttata
16921 ttagatatta gtttgagaca gtgtttctca agtctgtata ataagtttga tagtagggag
16981 gttttctctc aagaaaagaa ttattcagtg tgcacctaca taatcactgc ttagattcta
17041 caattaatat tttgctatat ttgattaaac gttttctgta aaagaaaaat attattatgt
17101 actatttagg tttatgggaa taattgttaa gttaaagtgt atgaacaaac ctggaatgaa
17161 atctgtttgc ctacatctat aatacaacta taaaacatag cagatgtaca aattagtagt
17221 taatagataa ctaaaatgca aatatggcac tactattata gtattatagt ttcttttgag
17281 tggcgtgtct gtaatatcac atgctgtgtt gatgcacttc accaaactgc tgttttcaaa
17341 ctgctttaaa tcctgccatt atagcacata gcaatgctat ttcactttca tttggcacaa
17401 aacacattta tatattgttt gcttctcttc ttttctgtaa tccccaggca acaaaactag
17461 aacatttgcc actaatctgg caacgtggtc ctatattatg aagtagtcat atagctgatc
17521 taaactatcc ttacagtgaa atgagagtat tgtgaaagtt ttgtagaaag ctccccatat
17581 gtcctgagaa tctatgcaca gaccccacag ttaaaagacc tttgaattgt gggaagacat
17641 gggtttaagt atcacttggt taccttctat ttgtgtaaca ttgaggtagt ttcatcttct
17701 gggttcccag tttccttaga gaatgaaaat gttgaattat gtgatttttt tttttttttg
17761 agacggagtt ttgctctttc gcccaggctg gagtgaagta gcacgatctc gactcactgc
17821 aacctccttc cccatgatc aagcaattct cctgcctcag cctcccaagt agctgggatt
17881 acaggcaccc gccccccacc ccccgccccc agctaatgtt tgtattttta gtacagatgg
17941 agttttgccg tgttggccag gctggtctcg aacttctgac ctcaggtgat ccactcgcct
18001 tggcctccca aagtgctagg attacaggca tgagccactg cgcctggcct atgtgattat
18061 taatatcacg tctagctgtg acaattctgt ctgatgctgg agtatttgaa ccagatggct
18121 ggctgtgcca ctcagttatt ctctccataa gactttgata ttttgttggt ctgcaagatg
18181 acggattctc aaaattcttg tcagtgaata ttgaacccta gtgaaatgta tggttctgta
18241 tcagttccaa aatgtaacca ctttctctag ccttagattc ccagttccaa aatgtaacca
18301 ttttctctag ccttagattc ccgttaaggg aaagggaatg ctctttgagt atgtcatcac
18361 catagtaaca ggcaaaacta gagggctttg atgctaaagc aagatactcc ataaatatgc
18421 ttaagaagac ttggggagac tggaatagtt gttccctttt agatgccagt gtataaatga
18481 atttgagcta ggatccgttt atttaaaatt tctttaggtg tatttgcttg catatggagt
18541 gcacatttac tctcattaat ggagttttag gaagcagtag agtaaatgca taaacatgta
18601 tgaaccgcca tgtttaactg gaagcctgca tttggaagtc aagtatctaa tcttagatta
18661 aattaggatg gggaaggatg ttggcaagag attttgaagc ttgttctgct tatattgaga
18721 acatcataga acagtttggc ctttttaaag ctagagaata gtgttgaata agtgatgttc
18781 catatattcc tgtttgacat tgacataaag gtttcctcat gatacagtaa tccctgatca
18841 gggatctgga agcctgtatt catttaaggt actcaggttt aacatactgg gtgcttttca
18901 caccatacta tacagtacca tgcaaagtgc tttcaagact gcaaatttgg cttagatccc
18961 ctttagtgag ctcctatgct atagtaaagg tagatagcca attattaaaa acagtcaaga
19021 caattgcacc tctaagcagt agtagcagtt gccacaccac cttgaatctt gaagtatttt
19081 cagcaacagg atgaccatta gccacaaatt tagtgtcagc ccttaaggtc ggtattggtt
19141 tgacccatat tttcatgtag ttctttttct tcacttgtct aatcttcccg tgtactgcca
19201 gggcttgtca ttagaggact ttagggagac caagcaggct agaaagtaga gacaggagat
19261 acctatgtct aatgcttcag tttatacttc ctaggttttt ttcattgggg tttttgtaac
19321 tcttttggta tcctaccggt gctttggtag cctactgaac cctgtctttc ttcttaagga
19381 cattctgagc atgtgagacc tgaggactgc aaacagctat aagaggctcc aaattaatca
19441 tatctttccc tttgagaatc tggccaagct ccagctaatc tacttggatg ggttgccagc
19501 tatctggaga aaaaggtagt ttggggaatt tattgttgta gtgcttctgt ctttggattg
19561 aacttcccac aactctcctt tttaaagcag aacacagctg ggcatggtgg ctcctgcttg
19621 taattccagg gctttgggag gttgaggtgg ggggatcact tgaggccagg agttgaagac
19681 ccatgtctct acaataaaat aaaattagtt gggcatggtg gtacgtgcct gtagtcctac
19741 ctactctgga ggctgaggca gcaggattgc ttgagcccag gagttcaagg ctgcagtgag
```

FIG. 7F

```
19801 ccatcattag ccactgcact ccagcctagg tggcagagcg ggacccagtc tcttaaaaag
19861 aaagaaaagc agaacgtgag ccagttttca tcaattccta tactttttct tttgcatgta
19921 cacatacatt ttaactttac ataatgagtt cggcctgttt catttatccc tcagagctgg
19981 gctccagtga ggtctgtaag ggcaagcata cttgatcccc aatgaagaat gagagatgca
20041 aagcactaaa ttatttcttt tctcaccaca cagcaagata gatttaatga acttaacacc
20101 ttttgattag tggcctttta aattattccc actttccttt ggcagatggg tattaagttc
20161 tcaggatttg tttacaaata agactaactt catctgtatt agctcagttt tggtaggcct
20221 aattccatta tcactgccat ttccttgttt taagaaatca aaatttctta gcttgaaaaa
20281 caattgaaat tgttaaaaag tggaatagga gagccccggg ggcctgtata aggaatttac
20341 tgaatccctg gttttctgta ccttgttttt ccttctgcat agatttgctt aactgttttt
20401 gtggcgtgta tttttttttt ttcgcagttt cgctcttgtt gcccaggctg gagtgcaatg
20461 gcgcaatctc agctcactgc aacctctgtc tcctgggttc aagttattct cctgcctcag
20521 cctctcgagt agctgagatt acaggcatgc gcgaccacgc caggctaatt ttgtattttt
20581 agtagagacg gggtttctcc atgttggtca ggctggtctc aaactcctga cctcaggtga
20641 ttcacccgcc tcgacctccc aaactgctgg gattacaggc gtgagccacc acgcctggcc
20701 agctgttgtt ataactggag ttctatgtgc ttgtgaccat tcttggtttc tccgaatatc
20761 ctagaacttt ggtggcgccc tattatacag gttgttgaag aaatgttacc atgtggattg
20821 agtaggaaac aattctcttt atcttggcaa tattatggca tggcactact taaagtacaa
20881 attaaaagag ggggatgcta cagaactagc tgacaggcac tttgatagag gtggatttct
20941 cagttcttaa aatagctctt tataaaggaa gccagaggca ttgtggagga gaattcttac
21001 ataactcata gggttagacc acatccgacc ttttctgtgt ggcttcatgg ctctcttggt
21061 tgagaaagca ttagtttctc cttccattag tttcaacctc ttgatttctt gacccccccta
21121 ctatattttg tgctgagaac acaagggtat taacaaccca cattgtagag gatcgctcag
21181 taataaagac tggagaataa aatgcagcat gggaatattg gcaattactc agttctaaat
21241 ttctcttgga aatgagggaa agcatacaga atagagctgg aatgaatagg ataatttttt
21301 ttttttttgc taagttggta gccagaatat aacagctccg cacaactgta aatgtccact
21361 cttcaatcca catgaagaaa agggtaaaaa tatggttgaa ctcaaccact agttgcccat
21421 tagaacagac tttcccagtg tactgcattt caatactttt tcttttatct cttttcagat
21481 cttcctcaga agaataggct tgttgtttta cagtgttagt gatccattcc ctttgacgat
21541 ccctaggtgg agatggggca tgaggatcct ccaggggaaa agctcactac cactgggcaa
21601 caaccctagg tcaggaggtt ctgtcaagat actttcctgg tcccagatag gaagataaag
21661 tctcaaaaac aaccaccaca cgtcaaggtg cgtaagctgt ccctaaaagc ataataagta
21721 gtcttaattt tgattttgtt ttccagtata cattgcactt agtgtttcac tgaggtcgta
21781 ttcatcatta ttctgcatat gatttggtaa aaacagcttc ctaactaacc tgggaagcaa
21841 ctgggtgtga gattaactgg ttaaagtgat gatgtaaaga gggtagcggg ttgcatgtgt
21901 tcgggtgttt ggagtgggac tatagcacgt ggcagaggct tacagctaag ttgttctttt
21961 aggagaacat ggacaactgt cacatcagtg acattgatca catgggcaaa tcattctgtt
22021 ccatgtggtc cccaaagtct ctcttaaagc cttacagaag aactttgcca atcatttaca
22081 tacttcagga tggcttggga tgccatggtg tataatacaa caagtgagag gtgtgtcttt
22141 ttatgctatg gttgctgatt gatggaagcc gcataaatac aaatggaaac ctgactaaaa
22201 atggcacaaa gttatctgtc atcaggcagg agctaaagaa ccaggaccct acattctcta
22261 ggtcagtgtt gggagaggct gattagcgag tgagaattgg cagataaagg tgaccattcg
22321 gtgcaataaa tcctgaacgt ataggctttg cccagcattc ttcgtaaata gtgggtagct
22381 ataaatttca tgaaatattt tcatgggtaa gaactcttga aatgttataa ttgactagaa
22441 atctctgtag atttagaaat agagagttac taacaaattg ttagaaagtc taggaactag
22501 aaagctaagt tgagagttat ctaggaagat ctatctattg tactcataat ctttagataa
22561 attctcctag ggccagtagt ctatgtgaat tttctttttc ttcttcttct tcttcttttt
22621 ttttgtattt tagctgcaat gttaaacaac ctatgtgaat tttcttattg tgagaatatt
22681 tgccttccag agtgactcac ctttatctca aagagcaata ttgtgagttt tgaaaatgct
22741 gctctaaggc tgtgttttgt tagtcctgag ccaggagact taaagcaaac ttgaggggtc
22801 ttaaaacatc gaagtgagcc ttaaacattg ggaagacctt atgtttttcc ctctcatatc
22861 tattattttt gtgatctcag ttattaatca tttaaaggga ctctttccta gctgattggc
22921 acttaaaaca ggatggaagt cttttttttt tttttttttt ttgagatgga gttttgctct
22981 tgttgcccag gctggagtgc aatggtgcaa tctcagctca ctgcaacctc tgcctcccgg
23041 gttcaagcga ttctcctgcc tcagcctccc aagtagctgg gattacagtc atgcaccacc
```

FIG. 7G

```
23101 acgcccggct aattttgtat ttttaataga gacggtgttt ctccatgttg gtcaggctgg
23161 tctcaaactc ctgacctcag gtgatccgcc cacctcaacc tcccaaagtg ctgggattat
23221 gggcgtgagc caccgcgccc ggcagttctg gtctttaact aaggtataag gctatgactg
23281 gtagtggtgt ctctagtgac tcatcaagtg atatttggca agacattttc ccatttatgc
23341 cagtttccta ttctgttgaa tgaggaaatt ttctctctaa agacctaaaa gttttgactt
23401 tataggtttc aaagttctgt ggaaacattt tctattgctt attaatttga atcttatgta
23461 actctagcac agtactcaat atttatggca tttacatggt ttatctcatg tttttttata
23521 gctcttcatt gttcctatct gccaaatcat tatacttcct acaagcagtg cagagagctg
23581 agtcttcagc aggtccaaga aatttgaaca cactgaagga agtcagcctt cccacctgaa
23641 gatcaacatg cctggcactc tagcacttga ggatagctga atgaagtaag ttgttgatgt
23701 tgcagtcctg tgaggatcac ttcagaactg ttataacagc tgtttttttgg gagctggtgt
23761 tggatggggt gtgttggtct aatgtgaagt ggggctaaat gtgagatgga aagatgacca
23821 gtcttccata ttactgactg ggttcactga agcaactcaa agacattatg gtcttcttac
23881 cagttgtatc acagaagaat ttagcctttg cttgtgtgtt ctatgtcttc actgtatagg
23941 ccctctgtca ttcttagagc cttaaacgtt gagaagctta aaacaccatt tctgctttct
24001 gctgaaaggg taaccctttc tcatctccgt ttgtgagaga ctctgtcgtc agttaagatt
24061 agtgtaaaaa gaaaactaaa ctctgaagta gccattataa aagtgtgaga atgaagtcag
24121 ttttctaaag agttggggaa aggtgatgct aaaggagggg attgagcaag tcctatcaaa
24181 gagcctttta tgaaaatact tagtcatctg tgacatccca tttggctctt ccagaaatcc
24241 tagtaaatag ttgtaacagg atgttaagag gcatacattg tgtgttttaa atcctctgct
24301 actcattagg tatatgacct ttgacaactt aaagtctcta gacttctctg tttgtgaggg
24361 ttaaatgaaa tcatgtatgt aaagtgctca cctattgcag tgcctggcac atgtcaagta
24421 aaaggtaacc caagaagact cataagttca tttcccacaa tataagtgac cactagcact
24481 atcaggtagc aggcagagtt ggcatgcttt ggttctatgt aagaaatccc taaggtaaaa
24541 gtttataaat agaagagcat ctgtgttggt attggtggtt gttattattg tagtactata
24601 agtagtattc gtagtaacaa tagtttatta taattactaa tgacactttt tgattttttt
24661 tatctttctg tgatgctttt catgcctctt gtgcccctca ctgtatcttg cctcttctac
24721 tacttacttc ctctgaatgt ctgcctttgc ttatctcttg cactcaagtg tgtatttctt
24781 tgtctctttc tttcttgtct ttgctctttg ttctctatct aaagtgtgtc ttacccattt
24841 ccatgtttct cttgctaatt tctttcgtgt gtgcctttgc ctcattttct ctttttgttc
24901 acaagagtgg tctgtgtctt gtcttagaca tatctctcat ttttcatttt gttgctattt
24961 ctctttgctc tcctagatgt ggctcttctt tcacgcttta tttcatgtct ccttttttggg
25021 tcacatgctg tgtgcttttt gtccttttct tgttctgtct acctctcctt tctctgccta
25081 cctctctttt ctctttgtga actgtgatta tttgttaccc cttccccttc tcgttcgttt
25141 taaatttcac cttttttctg agtctggcct cctttctgct gtttctactt tttatctcac
25201 atttctcatt tctgcatttc ctttctgcct ctcttgggct attctctctc tcctcccctg
25261 cgtgcctcag catctcttgc tgtttgtgat tttctatttc agtattaatc tctgttggct
25321 tgtatttgtt ctctgcttct tccctttcta ctcacctttg agtatttcag cctcttcatg
25381 aatctatctc cctctctttg atttcatgta atctctcctt aaatatttct ttgcatatgt
25441 gggcaagtgt acgtgtgtgt gtgtcatgtg tggcagaggg gcttcctaac ccctgcctga
25501 taggtgcaga acgtcggcta tcagagcaag cattgtggag cggttcctta tgccaggctg
25561 ccatgtgaga tgatccaaga ccaaaacaag gccctagact gcagtaaaac ccagaactca
25621 agtagggcag aaggtggaag gctcatatgg atagaaggcc caaagtataa gacagatggt
25681 ttgagacttg agacccgagg actaagatgg aaagcccatg ttccaagata gatagaagcc
25741 tcaggcctga aaccaacaaa agcctcaaga gccaagaaaa cagagggtgg cctgaattgg
25801 accgaaggcc tgagttggat ggaagtctca aggcttgagt tagaagtctt aagacctggg
25861 acaggacaca tggaaggcct aagaactgag acttgtgaca caaggccaac gacctaagat
25921 tagcccaggg ttgtagctgg aagacctaca acccaaggat ggaaggcccc tgtcacaaag
25981 cctacctaga tggatagagg acccaagcga aaaaggtatc tcaagactaa cggccggaat
26041 ctggaggccc atgacccaga acccaggaag gatagaagct tgaagacctg ggaaatcccc
26101 aagatgagaa ccctaaaccc tacctctttt ctattgttta cacttcttac tcttagatat
26161 ttccagttct cctgtttatc tttaagcctg attcttttga gatgtacttt ttgatgttgc
26221 cggttacctt tagattgaca gtattatgcc tgggccagtc ttgagccagc tttaaatcac
26281 agcttttacc tatttgttag gctatagtgt tttgtaaact tctgtttcta ttcacatctt
26341 ctccacttga gagagacacc aaaatccagt cagtatctaa tctggctttt gttaacttcc
```

FIG. 7H

```
26401 ctcaggagca gacattcata taggtgatac tgtatttcag tcctttcttt tgaccccaga
26461 agccctagac tgagaagata aaatggtcag gttgttgggg aaaaaaaagt gccaggctct
26521 ctagagaaaa atgtgaagag atgctccagg ccaatgagaa gaattagaca agaaatacac
26581 agatgtgcca gacttctgag aagcacctgc cagcaacagc ttccttcttt gagcttaggt
26641 gagcaggatt ctggggtttg ggatttctag tgatggttat ggaaagggtg actgtgcctg
26701 ggacaaagcg aggtcccaag gggacagcct gaactccctg ctcatagtag tggccaaata
26761 atttggtgga ctgtgccaac gctactcctg ggtttaatac ccatctctag gcttaaagat
26821 gagagaacct gggactgttg agcatgttta atactttcct tgattttttt cttcctgttt
26881 atgtgggaag ttgatttaaa tgactgataa tgtgtatgaa agcactgtaa aacataagag
26941 aaaaaccaat tagtgtattg gcaatcatgc agttaacatt tgaaagtgca gtgtaaattg
27001 tgaagcatta tgtaaatcag gggtccacag tttttctgta aggggtcaaa tcataaatac
27061 tttagactgt gggccatatg gtttctgtta catatttgtt ttttaaacaa cgtttttata
27121 aggtcaaaat cattcttagt ttttgagcca attggatttg gcctgctgtt catagcttac
27181 caccccctga tgtattattt gttattcaga gaaaatttct gaatactact agtttccttt
27241 tctgtgcctg tccctgtgct aggcactaaa aatgcaatga ttattgatat ctaggtgacc
27301 tgaaaaaaaa tagtgaatgt gctttgtaaa ctgtaaagca cttgtattct actgtgataa
27361 gcgttgtgga tacaaagaaa ggagcaagca taaaaaagtg ctctttcaaa aggatatagt
27421 actatgcaga cacaaggaat tgtttgataa atgaataaat tatatgtata tttgaggcca
27481 atttgtgttt gctgctctgg taattttgag taaaaatgca gtattccagg tatcagaaac
27541 gaaaacacat ggaaactgct tttaaacttt aaaatatact gaaaacataa gggactaagc
27601 ttgttgtggt cacctataat gtgccagata ccatgctggg tgctagagct accaaagggg
27661 gaaaagtatt ctcatagaac aaaaaatttc agaaaggtgc atattaaagt gctttgtaaa
27721 ctaaagcatg atacaaatgt caatgggcta catatttatg aatgaatgaa tggatgaatg
27781 aatattaagt gcctcttaca taccagctat tttgggtact gtaaaataca agattaattc
27841 tcctatgtaa taagaggaaa gtttatcctc tatactattc agatgtaagg aatgatatat
27901 tgcttaattt taaacaatca agactttact ggtgaggtta agttaaatta ttactgatac
27961 atttttccag gtaaccagga aagagctagt atgaggaaat gaagtaatag atgtgagatc
28021 cagaccgaaa gtcacttaat tcagcttgcg aatgtgcttt ctaaattata aagcacttgt
28081 aaatgaaaaa tttgatgctt tctgtatgaa taaaactttc tgtaagctag gtattgtctc
28141 tacaaaattc tcattgtata gttaaaccac agtgagaagg gttctataag tagttataca
28201 aaccaagggt ttaaatacct gttaaataga tcaattttga ttgcctacta tgtgaactca
28261 ctgttaaagg cactgaaaat ttatcatatt tcatttagcc acagccaaaa ataaggcaat
28321 acctatgtta gcattttgtg aactctaagg caccatataa atgtaactgt tgattttctc
28381 acttggtgct gggtactagg tttataaaat tgtatgatag ttattatatt gtgcaaataa
28441 agtaggaaaa tttgaataac aatgattatc ttttgaatac gcatacgcaa gggattggtt
28501 gtctgaagaa tgccactata gtagttatct attgtgtgcc aatctcattg ctaggcattg
28561 gggatgcaaa gataaaccat ctttattgtg tcttgggtag cagaagaaaa tatgtgtaaa
28621 atcaatttat aatttgtaaa ctgccaccca tatataagct atatctgctg aatgatcatt
28681 gattactctt atccttagag ataacaactg gggcacaaa catttattat cattattgaa
28741 cctacaacag agatctatgt gtagatttac aaagcctaca gttctataca gataggaatg
28801 aactattggc ttactgaatg gtgattactt tctgtggggc tcggaactac atgccctagg
28861 atataaaaat gatgttatca ttatagagtg ctcacagaag gaaatgaagt aatataggtg
28921 tgagatccag accaaaagtc atttaacaag tttattcagt gatgaaaaca tgggacaaat
28981 ggactaatat aaggcagtgt actaagctga gtagagagat aaagtcctgt ccagaagata
29041 catgcttcct ggcctgattg aggagatgga aaatttttgc aaaaaacaag gtgttgtggt
29101 cttccatcca gtttcttaag tgctgatgat aaaagtgaat tagacccacc ttgacctggc
29161 ctacagaagt aaaggagtaa aaataaatgc ctcaggcgtg ctttttgatt catttgataa
29221 acaaagcatc ttttatgtgg aatataccat tctgggtcct gaggataaga gagatgaggg
29281 cattagatca ctgacagctg aagatagaag aacatctttg gtttgattgt ttaaataata
29341 tttcaatgcc tattctctgc aaggtactat gtttcgtaaa ttaaataggt ctggcccaga
29401 agacccactc aattgccttt gagattaaaa aaaaaaaaaa aaagaaagaa aaatgcaagt
29461 ttctttcaaa ataaagagac atttttccta gtttcaggaa tcccccaaat cacttcctca
29521 ttggcttagt ttaaagccag gagactgata aaagggctca gggtttgttc tttaattcat
29581 taactaaaca ttctgctttt attacagtta aatggttcaa gatgtaacaa ctagttttaa
29641 aggtatttgc tcattggtct ggcttagaga caggaagaca tatgagcaat aaaaaaaaga
```

FIG. 7I

```
29701 ttcttttgca tttaccaatt tagtaaaaat ttattaaaac tgaataaagt gctgttctta
29761 agtgcttgaa agacgtaaac caaagtgcac tttatctcat ttatcttatg gtggaaacac
29821 aggaacaaat tctctaagag actgtgtttc tttagttgag aagaaacttc attgagtagc
29881 tgtgatatgt tcgatactaa ggaaaaacta aacagatcac ctttgacatg cgttgtagag
29941 tgggaataag agagggcttt ttattttttc gttcatacga gtattgatga agatgatact
30001 aaatgctaaa tgaaatatat ctgctccaaa aggcatttat tctgacttgg agatgcaaca
30061 aaaacacaaa aatggaatga agtgatactc ttcatcaaac agaagtgact gttatctcaa
30121 ccattttgtt aaatcctaaa cagaaaacaa aaaaaatcat gacgaaaaga cacttgctta
30181 ttaattggct tggaaagtag aatataggag aaaggttact gtttattttt tttcatgtat
30241 tcattcattc tacaaatata ttcgggtgcc aataggtact tggtataagg tttttggccc
30301 cagagacatg ggaaaaaaat gcatgccttc ccagagaatg cctaatactt tcctttggc
30361 ttgttttctt gttaggggca tggcttagtc cctaaataac attgtgtggt ttaattccta
30421 ctccgtatct cttctaccac tctggccact acgataagca ggtagctggg ttttgtagtg
30481 agcttgctcc ttaagttaca ggaactctcc ttataataga cacttcattt tcctagtcca
30541 tccctcatga aaaatgactg accactgctg ggcagcagga gggatgatga ccaactaatt
30601 cccaaacccc agtctcattg gtaccagcct tggggaacca cctacacttg agccacaatt
30661 ggttttgaag tgcatttaca aggtttgtct attttcagtt ctttactttt tacatgctga
30721 cacatacata cactgcctaa atagatctct ttcagaaaca atcctcagat aacgcatagc
30781 aaaatggaga tggagacatg atttctcatg caacagcttc tctaattata ccttagaaat
30841 gttctccttt ttatcatcaa atctgctcaa gaagggcttt ttatagtaga ataatatcag
30901 tggatgaaaa cagcttaaca ttttaccatg cttaagtttt aagaataaaa taaaaattgg
30961 aaataattgg ccaaaattga aaggaaaaat ttttttaaaa tttctctaaa tgtaggcctg
31021 gctgggcttt gacctttttcc gtttttaaat cactcacaga gggtgggaca ggaggaagag
31081 tgaaggaaaa ggtcaaacct gttttaaggg caacctgcct ttgttctgaa ttggtcttaa
31141 gaacattacc agctccaggt ttaaattgtt cagtttcatg cagttccaat agctgatcat
31201 tgttgagatg aggacaaaat cctttgtcct cactagtttg ctttacattt ttgaaaagta
31261 ttatttttgt ccaagtgctt atcaactaaa ccttgtgtta ggtaagaatg gaatttatta
31321 agtgaatcag tgtgaccctt cttgtcataa gattatctta aagctgaagc caaaatatgc
31381 ttcaaaagaa gaggacttta ttgttcattg tagttcatac attcaaagca tctgaactgt
31441 agtttctata gcaagccaat tacatccata agtggagaag gaaatagata aatgtcaaag
31501 tatgattggt ggagggagca aggttgaaga taatctgggg ttgaaatttt ctagttttca
31561 ttctgtacat ttttagttag acatcagatt tgaaatatta atgtttacct ttcaatgtgt
31621 ggtatcagct ggactcagta acaccccttt cttcagctgg ggatggggaa tggattattg
31681 gaaaatggaa agaagaaagt aactaaaagc cttcctttca cagtttctgg catcactacc
31741 actactgatt aaacaagaat aagagaacat tttatcatca tctgctttat tcacataaat
31801 gaagttgtga tgaataaatc tgcttttatg cagacacaag gaattaagtg gcttcgtcat
31861 tgtccttcta cctcaaagat aatttattcc aaaagctaag ataaatggaa gactcttgaa
31921 cttgtgaact gatgtgaaat gcagaatctc ttttgagtct ttgctgtttg gaagattgaa
31981 aaatattgtt cagcatgggt gaccaccaga aagtaatctt aagccatcta gatgtcacaa
32041 ttgaaacaaa ctggggagtt ggttgctatt gtaaaataaa atatactgtt ttga (SEQ
      ID NO:3)
```

FIG. 7J

```
                              SEQUENCE LISTING

<160> NUMBER OF SEQ ID NOS: 2

<210> SEQ ID NO 1
<211> LENGTH: 16481
<212> TYPE: DNA
<213> ORGANISM: Homo sapiens

<400> SEQUENCE: 1

ccttcagttc ttaaagcgct gcaattcgct gctgcagcca tatttcttac tctctcgggg      60

ctggaagctt cctgactgaa gatctctctg cacttggggt tctttctaga acattttcta     120

gtcccccaac accctttatg gcgtatttct ttaaaaaaat cacctaaatt ccataaaata     180

ttttttttaaa ttctatactt tctcctagtg tcttcttgac acgtcctcca tattttttta     240

aagaaagtat ttggaatatt ttgaggcaat ttttaatatt taaggaattt ttctttggaa     300

tcatttttgg tgacatctct gttttttgtg gatcagtttt ttactcttcc actctctttt     360

ctatattttg cccatcgggg ctgcggatac ctggttttat tattttttct ttgcccaacg     420

gggccgtgga tacctgcctt ttaattcttt tttattcgcc catcggggcc gcggatacct     480

gctttttatt tttttttcct tagcccatcg gggtatcgga tacctgctga ttcccttccc     540
```

-continued

```
ctctgaaccc ccaacactct ggcccatcgg ggtgacggat atctgctttt taaaaatttt    600
cttttttttgg cccatcgggg cttcggatac ctgctttttt ttttttttatt ttccttgccc    660
atcggggcct cggatacctg ctttaatttt tgtttttctg cccatcgggg ccgcggatac    720
ctgctttgat ttttttttttt catcgcccat cggtgctttt tatggatgaa aaaatgttgg    780
ttttgtgggt tgttgcactc tctggaatat ctacactttt ttttgctgct gatcatttgg    840
tggtgtgtga gtgtacctac cgctttggca gagaatgact ctgcagttaa gctaagggcg    900
tgttcagatt gtggaggaaa agtggccgcc attttagact tgccgcataa ctcggcttag    960
ggctagtcgt ttgtgctaag ttaaactagg gaggcaagat ggatgatagc aggtcaggca   1020
gaggaagtca tgtgcattgc atgagctaaa cctatctgaa tgaattgatt tggggcttgt   1080
taggagcttt gcgtgattgt tgtatcggga ggcagtaaga atcatctttt atcagtacaa   1140
gggactagtt aaaaatggaa ggttaggaaa gactaaggtg cagggcttaa aatggcgatt   1200
ttgacattgc ggcattgctc agcatggcgg gctgtgcttt gttaggttgt ccaaaatggc   1260
ggatccagtt ctgtcgcagt gttcaagtgg cgggaaggcc acatcatgat gggcgaggct   1320
ttgttaagtg gttagcatgg tggtggacat gtgcggtcac acaggaaaag atggcggctg   1380
aaggtcttgc cgcagtgtaa aacatggcgg gcctctttgt ctttgctgtg tgcttttcgt   1440
gttgggtttt gccgcaggga caatatggca ggcgttgtca tatgtatatc atggcttttg   1500
tcacgtggac atcatggcgg gcttgccgca ttgttaaaga tggcgggttt tgccgcctag   1560
tgccacgcag agcgggagaa aaggtgggat ggacagtgct ggattgctgc ataacccaac   1620
caattagaaa tgggggtgga attgatcaca gccaattaga gcagaagatg gaattagact   1680
gatgacacac tgtccagcta ctcagcgaag acctgggtga attagcatgg cacttcgcag   1740
ctgtctttag ccagtcagga gaaagaagtg gaggggccac gtgtatgtct cccagtgggc   1800
ggtacaccag gtgttttcaa ggtcttttca aggacattta gcctttccac ctctgtcccc   1860
tcttatttgt cccctcctgt ccagtgctgc ctcttgcagt gctggatatc tggctgtgtg   1920
gtctgaacct ccctccattc ctctgtattg gtgcctcacc taaggctaag tatacctccc   1980
cccccacccc ccaacccccc caactcccca cccccacccc ccacccccca cctccccacc   2040
cccctacccc cctacccccc tacccccctc tggtctgccc tgcactgcac tgttgccatg   2100
ggcagtgctc caggcctgct tggtgtggac atggtggtga gccgtggcaa ggaccagaat   2160
ggatcacaga tgatcgttgg ccaacaggtg gcagaagagg aattcctgcc ttcctcaaga   2220
ggaacaccta ccccttggct aatgctgggg tcggattttg atttatattt atcttttgga   2280
tgtcagtcat acagtctgat tttgtggttt gctagtgttt gaatttaagt cttaagtgac   2340
tattatagaa atgtattaag aggctttatt tgtagaattc actttaatta catttaatga   2400
gtttttgttt tgagttcctt aaaattcctt aaagttttta gcttctcatt acaaattcct   2460
taaccttttt ttggcagtag atagtcaaag tcaaatcatt tctaatgttt taaaaatgtg   2520
ctggtcattt tctttgaaat tgacttaact attttccttt gaagagtctg tagcacagaa   2580
acagtaaaaa atttaacttc atgacctaat gtaaaaaaga gtgtttgaag gtttacacag   2640
gtccaggcct tgctttgttc ccatccttga tgctgcacta attgactaat cacctactta   2700
tcagacagga aacttgaatt gctgtggtct ggtgtcctct attcagactt attatattgg   2760
agtatttcaa tttttcgttg tatcctgcct gcctagcatc cagttcctcc ccagccctgc   2820
tcccagcaaa cccctagtct agccccagcc ctactcccac ccggccccag ccctgcccca   2880
ggcccagtcc cctaaccccc cagccctagg cccagtccca gtcctagttc ctcagtctgt   2940
```

```
ccagcttctc tcgaaagtca ctctaatttt cattgattca gtgctcaaaa taagttgtcc   3000
attggtatcc tattatactg ggatattccg tttacccttg gcattgctga tcttcagtac   3060
tgactccttg accattttca gttaagcata caatcccatt tgtctgtgat ctcaggacaa   3120
agaatttcct tactcggtac gttgaagtta gggaatgtca attgagagct ttctatcaga   3180
gcattattgc ccacaatttg agttacttat cattttctcg atcccctgcc cttaaaggag   3240
aaaccatttc tctgtcattg cttctgtagt cacagtccca attttgagta gtgatctttt   3300
cttgtgtact gtgttggcca cctaaaactc tttgcattga gtaaaattct aattgccaat   3360
aatcctaccc attggattag acagcactct gaaccccatt tgcattcagc agggggtcgc   3420
agacaacccg tcttttgttg gacagttaaa atgctcagtc ccaattgtca tagctttgcc   3480
tattaaacaa aggcacccta ctgcgctttt tgctgtgctt ctggagaatc ctgctgttct   3540
tggacaatta aagaacaaag tagtaattgc taattgtctc acccattaat catgaagact   3600
accagtcgcc cttgcatttg ccttgaggca gcgctgacta cctgagattt aagagtttct   3660
taaattattg agtaaaatcc caattatcca tagttctgtt agttacacta tggcctttgc   3720
aaacatcttt gcataacagc agtgggactg actcattctt agagcccctt cccttggaat   3780
attaatggat acaatagtaa ttattcatgg ttctgcgtaa cagagaagac ccacttatgt   3840
gtatgccttt atcattgctc ctagatagtg tgaactacct accaccttgc attaatatgt   3900
aaaacactaa ttgcccatag tcccactcat tagtctagga tgtcctcttt gccattgctg   3960
ctgagttctg actacccaag tttccttctc ttaaacagtt gatatgcata attgcatata   4020
ttcatggttc tgtgcaataa aaatggattc tcaccccatc ccaccttctg tgggatgttg   4080
ctaacgagtg cagattattc aataacagct cttgaacagt taatttgcac agttgcaatt   4140
gtccagagtc ctgtccatta gaaagggact ctgtatccta tttgcacgct acaatgtggg   4200
ctgatcaccc aaggactctt cttgtgcatt gatgttcata attgtatttg tccacgatct   4260
tgtgcactaa cccttccact ccctttgtat tccagcaggg gacccttact actcaagacc   4320
tctgtactag gacagtttat gtgcacaatc ctaattgatt agaactgagt cttttatatc   4380
aaggtccctg catcatcttt gctttacatc aagagggtgc tggttaccta atgcccctcc   4440
tccagaaatt attgatgtgc aaaatgcaat ttccctatct gctgttagtc tggggtctca   4500
tcccctcata ttccttttgt cttacagcag ggggtacttg ggactgttaa tgcgcataat   4560
tgcaattatg gtcttttcca ttaaattaag atcccaactg ctcacaccct cttagcatta   4620
cagtagaggg tgctaatcac aaggacattt cttttgtact gttaatgtgc tacttgcatt   4680
tgtccctctt cctgtgcact aaagacccca ctcacttccc tagtgttcag cagtggatga   4740
cctctagtca agacctttgc actaggatag ttaatgtgaa ccatggcaac tgatcacaac   4800
aatgtctttc agatcagatc cattttatcc tccttgtttt acagcaaggg atattaatta   4860
cctatgttac ctttccctgg gactatgaat gtgcaaaatt ccaatgttca tggtctctcc   4920
ctttaaacct atattctacc ccttttacat tatagaaagg gatgctggaa acccagagtc   4980
cttctcttgg gactcttaat gtgtatttct aattatccat gactcttaat gtgcatattt   5040
tcaattgcct aattgatttc aattgtctaa gacatttcaa atgtctaatt gattagaact   5100
gagtctttta tatcaagcta atatctagct tttatatcaa gctaatatct tgacttctca   5160
gcatcataga agggggtact gatttcctaa agtctttctt gaatttctat tatgcaaaat   5220
tgccctgagg ccgggtgtgg tggctcacac ctgtaatccc agcactttgg gaggctgagg   5280
tgggaagatc ccttactgcc aggagtttga gaccagcctg gccaacatta aaaaaaaaaa   5340
```

```
aaaaagtaag acaattgccc tggaatccca tccccctcac acctccttgg caaagcagca   5400

ggagtgctaa ctagctagtg cttcttctct tatactgctt aaatgcgcat aattagcagt   5460

agttgatgtg cccctatgtt agagtagaat cccgcttcct tgctccattt gcattactgc   5520

aggagcttct aactagcctg aattcactct cttggactgt taatgtgcat acttatattt   5580

gctgctgtac ttttttacca tgtaaggacc ccacccactg tatttacatc ccagctggaa   5640

gtacctacta cttaagaccc ttagactagt aaagttagcg tgcataatct taggtgttat   5700

atacacattt tcagttgcat acagttgtgc cttttatcag gactcctgta cttatcaaag   5760

cagagagtgc taatcaatat taagcccttc tcttcgaact gtagatggca tgtaattgca   5820

gttgtcaatg gtccttcaat tagacttggg tttctgacct atcacaccct ctttgcttta   5880

ttgcatgggg tactattcac ttaaggcccc tttctcaaac tgttaatgtg cctaatgaca   5940

attacatcag tatccttcct tttgaaggac agcatggttg gtgacaccta aggccccatt   6000

tcttggcctc ccaatatgtg tgattgtatt tgtcgaggtt gctatgcact agagaaggaa   6060

agtgctcccc tcatccccac ttttcccttc cagcaggaag tgcccacccc ataagaccct   6120

tttatttgga gagtctaggt gcacaattgt aagtgaccac aagcatgcat cttggacatt   6180

tatgtgcgta atcgcacact gctcattcca tgtgaataag gtcctactct ccgacccctt   6240

ttgcaataca gaagggttgc tgataacgca gtccccttttt cttggcatgt tgtgtgtgat   6300

tataatcgtc tgggatccta tgcactagaa aaggagggtc ctctccacat acctcagtct   6360

cacctttccc ttccagcagg gagtgcccac tccataagac tctcacattt ggacagtcaa   6420

ggtgcgtaat tgttaagtga acacaaccat gcaccttaga catggatttg cataactaca   6480

cacagctcaa cctatctgaa taaaatccta ctctcagacc ccttttgcag tacagcaggg   6540

gtgctgatca ccaaggccct tttcctggc ctggtatgcg tgtgattatg tttgtcccgg   6600

ttcctgtgta ttagacatgg aagcctcccc tgccacactc cacccccaat cttcctttcc   6660

cttccggcag gagtgccctc tccataagac gcttacgttt ggacaatcaa ggtgcacagt   6720

tgtaagtgac cacaggcata caccttggac attaatgtgc ataaccactt tgcccattcc   6780

atctgaataa ggtcctactc tcagacccct tttgcagtac agcaggggtg ctgatcacca   6840

aggccccttt tcttggcctg ttatgtgcgt gattatattt gtctgggttc ctgtgtatta   6900

gacaaggaag ccttcccccc gcccccaccc ccactcccag tcttcctttc ccttccagca   6960

gggagtgccc cctccataag atcattacat ttggacaatc aaggtgcaca attataagtg   7020

accacagcca tgcaccttgg acattattgg acattaatgt gcgtaactgc acatggccca   7080

tcccatctga ataaggacct actctcagat gcctttgcag tacagcaggg gtactgaatc   7140

accaaggccc tttttcttgg cctgttatgt gtgtgattat atttatccca gtttctgtgt   7200

aatagacatg aaagcctccc ctgccacacc ccacctccaa tcttcctttc ccttccacca   7260

gggagtgtcc actccatata cccttacatt tggacaatca aggtgcacaa ttgtaagtga   7320

gcataggcac tcaccttgga catgaatgtg cataactgca catggcccat cccatctgaa   7380

taaggtccta ctctcagacc ctttttgcag tacagcaggg gtgctgatca ccaaggcccc   7440

ttttcctggc ctgttatgtg tgtgattata tttgttccag ttcctgtgta atagacatgg   7500

aagcctcccc tgccacactc cacccccaat cttcctttcc ttctggcagg aagtacccgc   7560

tccataagac ccttacattt ggacagtcaa ggtgcacaat tgtatgtgac cacaaccatg   7620

caccttggac ataaatgtgt gtaactgcac atggcccatc ccatctgaat aaggtcctac   7680

tctcagaccc cttttgcagt acagtaggtg tgctgataac caaggcccct cttcctggcc   7740
```

```
tgttaacgta tgtgattata tttgtctggg ttccagtgta taagacatgg aagcctcccc   7800
tgccccaccc caccctcaat cttcctttcc cttctggcag ggagtgccag ctccataaga   7860
accttacatt tggacagtca aggtgcacaa ttctaagtga ccgcagccat gcaccttggt   7920
caataatgtg tgtaactgca cacggcctat ctcatctgaa taaggcctta ctctcagacc   7980
ccttttgcag tacagcaggg gtgctgataa ccaaggccca ttttcctggc ctgttatgtg   8040
tgtgattata tttgtccagg tttctgtgta ctagacaagg aagcctcctc tgccccatcc   8100
catctacgca taatctttct tttcctccca gcagggagtg ctcactccat aagaccctta   8160
catttggaca atcaaggtgc acaattgtaa gtgaccacaa ccatgcatct tggaaattta   8220
tgtgcataac tgcacatggc ttatcctatt tgaataaagt cctactctca gacccccttt   8280
gcagtatagc tggggtgctg atcactgagg cctctttgct tggcttgtct atattcttgt   8340
gtactagata agggcacctt ctcatggact ccctttgctt ttcaacaagg agtacccact   8400
actttttaag attcttatat ttgtccaaag tacatggttt taattgacca caacaatgtc   8460
ccttggacat taatgtatgt aatcaccaca tggttcatcc taattaaaca aagttctacc   8520
ttctcaccct ccatttgcag tataccaggg ttgctgaccc cctaagtccc cttttcttgg   8580
cttgttgaca tgcataattg catttatgtt ggttcttgtg ccctagacaa ggatgcccca   8640
cctcttttca atagtgggtg cccactcctt atgatcttta catttgaaca gttaatgtga   8700
ataattgcag ttgtccacaa ccctatcact tctaggacca ttatacctct tttgcattac   8760
tgtggggtat actgtttccc tccaaggccc cttctggtgg actatcaaca tataattgaa   8820
attttctttt gtctttgtca gtagattaag gtcataccc atcacctttc ctttgtagta    8880
caacagggtg tcctgatcaa ccaaagtcct gttgttttgg actgttaata tgtgcaatta   8940
catttgctcc tgatctgtgc actagataag gatcctacct actttcttag tgtttttagc   9000
aggtagtgcc cactactcaa gactgtcact tggaatgttc atgtgcacaa actcaattct   9060
ctaagcatgt tcctgtacca cctttgcttt agagcagggg gatgatattc actaagtgcc   9120
ccttcttttg gacttaatat gcattaatgc aattgtccac ctcttctttt agactaagag   9180
ttgatctcca catattcccc ttgcatcagg ggcatgttaa ttatgaatga accctttttct  9240
tttaatatta atgtcataat tgtatttgtg gacctgtgta ggagaaaaag accctatgtt   9300
cctcccatta ccctttggat tgctgctgag aagtgttaac tactcataat ctcagctctt   9360
ggacaattaa tagcattaat aacaattatc aagggcactg atcattagat aagactcctg   9420
cttcctcgtt gcttacatcg gggtactga cccactaagg ccccttgtac tgttaatgtg    9480
aatatttgca attatatatg tctccttctg gtagagtggg atattatgcc ctagtatccc   9540
ctttgcatta ctgcaggggc tgctgactac tcaaaacttc tcctgggact gttaataggc   9600
acaatggcag ttatcaatgg ttttctccct ccctgacctt gttaagcaag cgccccaccc   9660
caccccttagt ttcccatggc ataataaagt ataagcattg gagtattcca tgcacttgtc  9720
tatcaaacag tggtccatac tcccaaccct tttgcattgc gccagtgtgt aaaatcacag   9780
gtagccatgg tgtcatgctt tatatacgaa gtcttccctc tctctgcccc ttgtgtgccc   9840
ttggcccctt tttacagact attgctcaca atctcaggtg tccatatttg cagctattag   9900
gtaagattgt gctgtctccc tcttcccttc cctctgccct gccccttttg cctctttgct   9960
gggtaatgtt gaccagacaa ggccctttct cttggactta aacaattctc agttgcactt  10020
tccttggtcc acccattata catgaacccc tctacttcct ttcgcattgc ttctgagtat  10080
gctgactacc caaagcccct tctgtgttat taataaacac agtactgatt gtcccatttt  10140
```

```
tcagcccatc agtccaagat ctccctacca ctttggtgtg ttggtgcagt gttgactatg  10200
aaaagcaggc ctgaactagg tggataagcc ttcactcatt ttctttcatt tattaatgat  10260
cctagtttca attattgtca gattctgggg acaagaacca ttcttgccca cctgtgttac  10320
tgctttactg tgcaaaatac tgaaggcaag tcagacccag ggagctggat tgccatcctt  10380
tattttgtgt ttccagtgta cactataaaa ttgtctcccc aggaaggaag gttggcactt  10440
tctctgcatt cttctttcca gagcagattg cctggttaag aatctcttgt tgtcccttct  10500
gtatattgtt attgtaaagt gccaaatgcc aggatacagc cagaaaaatt gcttattatt  10560
attaaaaaaa tttttttaag aaagacatct ggattgtagg gtggactcga taacctggtc  10620
attatttttt tgaagccaaa atatccattt atactatgta cctggtgacc agtgtctctc  10680
attttaactg agggtggtgg gtctgtggat agaacactga ctcttgctat tttaatatca  10740
aagatattct agagtggaac tcttaagacc agtatctttg tgtgggcttt accagcattc  10800
acttttagaa aaactaccta aattttataa tcctttaatt tcttcatctg gagcacctgc  10860
ccctacttat ttcaagaaga ttgcagtaaa acgattaaat gagggaacat atgcagaggt  10920
gcttttaaaa agcatatgcc acctttttta ttaattatta tataaaatga agcatttaat  10980
tatagtaata atttgaagta gtttgaagta ccacactgag gtgaggactt aaaaatgata  11040
agacgagttc cctattttat aagaaaaata agccaaaatt aaatattctt ttggatataa  11100
atttcaacag tgagatagct gcctagtgga aatgaataat atcccagcca ctagtgtaca  11160
gggtgttttg tggcacagga ttatgtaata tggaactgct caagcaaata actagtcatc  11220
acaacagcag ttctttgtaa taactgaaaa agaatattgt ttctcggaga aggatgtcaa  11280
aagatcggcc cagctcaggg agcagtttgc cctactagct cctcggacag ctgtaaagaa  11340
gagtctctgg ctctttagaa tactgatccc attgaagata ccacgctgca tgtgtcctta  11400
gtagtcatgt ctccttaggc tcctcttgga cattctgagc atgtgagacc tgaggactgc  11460
aaacagctat aagaggctcc aaattaatca tatctttccc tttgagaatc tggccaagct  11520
ccagctaatc tacttggatg ggttgccagc tatctggaga aaaagatctt cctcagaaga  11580
ataggcttgt tgttttacag tgttagtgat ccattccctt tgacgatccc taggtggaga  11640
tggggcatga ggatcctcca ggggaaaagc tcactaccac tggcaacaa ccctaggtca  11700
ggaggttctg tcaagatact ttcctggtcc cagataggaa gataaagtct caaaaacaac  11760
caccacacgt caagctcttc attgttccta tctgccaaat cattatactt cctacaagca  11820
gtgcagagag ctgagtcttc agcaggtcca agaaatttga acacactgaa ggaagtcagc  11880
cttcccacct gaagatcaac atgcctggca ctctagcact tgaggatagc tgaatgaatg  11940
tgtatttctt tgtctctttc tttcttgtct ttgctctttg ttctctatct aaagtgtgtc  12000
ttacccattt ccatgtttct cttgctaatt tctttcgtgt gtgcctttgc ctcattttct  12060
ctttttgttc acaagagtgg tctgtgtctt gtcttagaca tatctctcat ttttcatttt  12120
gttgctattt ctctttgctc tcctagatgt ggctcttctt tcacgcttta tttcatgtct  12180
cctttttggg tcacatgctg tgtgcttttt gtccttttct tgttctgtct acctctcctt  12240
tctctgccta cctctctttt ctctttgtga actgtgatta tttgttaccc cttccccttc  12300
tcgttcgttt taaatttcac cttttttctg agtctggcct cctttctgct gtttctactt  12360
tttatctcac atttctcatt tctgcatttc ctttctgcct ctcttgggct attctctctc  12420
tcctcccctg cgtgcctcag catctcttgc tgtttgtgat tttctatttc agtattaatc  12480
tctgttggct tgtatttgtt ctctgcttct tccctttcta ctcacctttg agtatttcag  12540
```

```
cctcttcatg aatctatctc cctctctttg atttcatgta atctctcctt aaatatttct  12600
ttgcatatgt gggcaagtgt acgtgtgtgt gtgtcatgtg tggcagaggg gcttcctaac  12660
ccctgcctga taggtgcaga acgtcggcta tcagagcaag cattgtggag cggttcctta  12720
tgccaggctg ccatgtgaga tgatccaaga ccaaaacaag gccctagact gcagtaaaac  12780
ccagaactca agtagggcag aaggtggaag gctcatatgg atagaaggcc caaagtataa  12840
gacagatggt ttgagacttg agacccgagg actaagatgg aaagcccatg ttccaagata  12900
gatagaagcc tcaggcctga aaccaacaaa agcctcaaga gccaagaaaa cagagggtgg  12960
cctgaattgg accgaaggcc tgagttggat ggaagtctca aggcttgagt tagaagtctt  13020
aagacctggg acaggacaca tggaaggcct aagaactgag acttgtgaca caaggccaac  13080
gacctaagat tagcccaggg ttgtagctgg aagacctaca acccaaggat ggaaggcccc  13140
tgtcacaaag cctacctaga tggatagagg acccaagcga aaaaggtatc tcaagactaa  13200
cggccggaat ctggaggccc atgacccaga acccaggaag gatagaagct tgaagacctg  13260
gggaaatccc aagatgagaa ccctaaaccc tacctctttt ctattgttta cacttcttac  13320
tcttagatat ttccagttct cctgtttatc tttaagcctg attcttttga gatgtacttt  13380
ttgatgttgc cggttacctt tagattgaca gtattatgcc tgggccagtc ttgagccagc  13440
tttaaatcac agcttttacc tatttgttag gctatagtgt tttgtaaact tctgtttcta  13500
ttcacatctt ctccacttga gagagacacc aaaatccagt cagtatctaa tctggctttt  13560
gttaacttcc ctcaggagca gacattcata taggtgatac tgtatttcag tcctttcttt  13620
tgaccccaga agccctagac tgagaagata aaatggtcag gttgttgggg aaaaaaaaag  13680
tgccaggctc tctagagaaa aatgtgaaga gatgctccag gccaatgaga agaattagac  13740
aagaaataca cagatgtgcc agacttctga gaagcacctg ccagcaacag cttccttctt  13800
tgagcttagg tgagcaggat tctggggttt gggatttcta gtgatggtta tggaaagggt  13860
gactgtgcct gggacaaagc gaggtcccaa ggggacagcc tgaactccct gctcatagta  13920
gtggccaaat aatttggtgg actgtgccaa cgctactcct gggtttaata cccatctcta  13980
ggcttaaaga tgagagaacc tgggactgtt gagcatgttt aatactttcc ttgatttttt  14040
tcttcctgtt tatgtgggaa gttgatttaa atgactgata atgtgtatga aagcactgta  14100
aaacataaga gaaaaaccaa ttagtgtatt ggcaatcatg cagttaacat ttgaaagtgc  14160
agtgtaaatt gtgaagcatt atgtaaatca ggggtccaca gtttttctgt aaggggtcaa  14220
atcataaata ctttagactg tgggccatat ggtttctgtt acatatttgt tttttaaaca  14280
acgtttttat aaggtcaaaa tcattcttag tttttgagcc aattggattt ggcctgctgt  14340
tcatagctta ccaccccctg atgtattatt tgttattcag agaaaatttc tgaatactac  14400
tagtttcctt ttctgtgcct gtccctgtgc taggcactaa aaatgcaatg attattgata  14460
tctaggtgac ctgaaaaaaa atagtgaatg tgctttgtaa actgtaaagc acttgtattc  14520
tactgtgata agcgttgtgg atacaaagaa aggagcaagc ataaaaaagt gctctttcaa  14580
aaggatatag tactatgcag acacaaggaa ttgtttgata aatgaataaa ttatatgtat  14640
atttgaggcc aatttgtgtt tgctgctctg gtaattttga gtaaaaatgc agtattccag  14700
gtatcagaaa cgaaaacaca tggaaactgc ttttaaactt taaaatatac tgaaaacata  14760
agggactaag cttgttgtgg tcacctataa tgtgccagat accatgctgg gtgctagagc  14820
taccaaaggg ggaaaagtat tctcatagca acaaaaaatt tcagaaaggt gcatattaaa  14880
gtgctttgta aactaaagca tgatacaaat gtcaatgggc tacatattta tgaatgaatg  14940
```

```
aatggatgaa tgaatattaa gtgcctctta cataccagct attttgggta ctgtaaaata  15000

caagattaat tctcctatgt aataagagga aagtttatcc tctatactat tcagatgtaa  15060

ggaatgatat attgcttaat tttaaacaat caagacttta ctggtgaggt taagttaaat  15120

tattactgat acatttttcc aggtaaccag gaaagagcta gtatgaggaa atgaagtaat  15180

agatgtgaga tccagaccga aagtcactta attcagcttg cgaatgtgct ttctaaatta  15240

taaagcactt gtaaatgaaa aatttgatgc tttctgtatg aataaaactt tctgtaagct  15300

aggtattgtc tctacaaaat tctcattgta tagttaaacc acagtgagaa gggttctata  15360

agtagttata caaaccaagg gtttaaatac ctgttaaata gatcaatttt gattgcctac  15420

tatgtgaact cactgttaaa ggcactgaaa atttatcata tttcatttag ccacagccaa  15480

aaataaggca atacctatgt tagcattttg tgaactctaa ggcaccatat aaatgtaact  15540

gttgattttc tcacttggtg ctgggtacta ggtttataaa attgtatgat agttattata  15600

ttgtgcaaat aaagtaggaa aatttgaata acaatgatta tcttttgaat acgcatacgc  15660

aagggattgg ttgtctgaag aatgccacta tagtagttat ctattgtgtg ccaatctcat  15720

tgctaggcat tggggatgca aagataaacc atctttattg tgtcttgggt agcagaagaa  15780

aatatgtgta aaatcaattt ataatttgta aactgccacc catatataag ctatatctgc  15840

tgaatgatca ttgattactc ttatccttag agataacaac tgggggcaca aacatttatt  15900

atcattattg aacctacaac agagatctat gtgtagattt acgaagccta cagttctata  15960

cagataggaa tgaactattg gcttactgaa tggtgattac tttctgtggg gctcggaact  16020

acatgcccta ggatataaaa atgatgttat cattatagag tgctcacaga aggaaatgaa  16080

gtaatatagg tgtgagatcc agaccaaaag ttatttaaca agtttattca gtgatgaaaa  16140

catgggacaa atggactata taaggcagtg tactaagctg agtagagaga taaagtcctg  16200

tccagaagat acatgctttc ctggcctgat tgaggagatg gaaaattttt gcaaaaaaca  16260

aggtgtttgt ggtcttccat ccagtttctt aagtgctgat gataaaagtg aattagaccc  16320

accttgacct ggcctacaga agtaaaggag taaaaataaa tgcctcaggc gtgctttttg  16380

attcatttga taaacaaagc atcttttatg tggaatatac cattctgggt cctgaggata  16440

agagagatga gggcattaga tcactgacag ctgaagatag a                     16481
```

<210> SEQ ID NO 2
<211> LENGTH: 32094
<212> TYPE: DNA
<213> ORGANISM: Homo sapiens

<400> SEQUENCE: 2

```
cttcagttct taaagcgctg caattcgctg ctgcagccat atttcttact ctctcggggc     60

tggaagcttc ctgactgaag atctctctgc acttggggtt ctttctagaa cattttctag    120

tcccccaaca ccctttatgg cgtatttctt taaaaaaatc acctaaattc cataaaaatat    180

ttttttaaat tctatacttt ctcctagtgt cttcttgaca cgtcctccat attttttttaa    240

agaaagtatt tggaatattt tgaggcaatt tttaatattt aaggaatttt tctttggaat    300

catttttggt tgacatctct gttttttgtg gatcagtttt ttactcttcc actctctttt    360

ctatattttg cccatcgggg ctgcggatac ctggttttat tattttttct ttgcccaacg    420

gggccgtgga tacctgcctt ttaattcttt tttattcgcc catcggggcc gcggatacct    480

gctttttatt tttttttcct tagcccatcg gggtatcgga tacctgctga ttcccttccc    540

ctctgaaccc ccaacactct ggcccatcgg ggtgacggat atctgctttt taaaaatttt    600
```

-continued

```
cttttttgg cccatcgggg cttcggatac ctgcttttt tttttttatt tttccttgcc    660
catcggggcc tcggatacct gctttaattt ttgtttttct ggcccatcgg ggccgcggat   720
acctgctttg attttttttt ttcatcgccc atcggtgctt tttatggatg aaaaaatgtt   780
ggttttgtgg gttgttgcac tctctggaat atctacactt ttttttgctg ctgatcattt   840
ggtggtgtgt gagtgtacct accgctttgg cagagaatga ctctgcagtt aagctaaggg   900
cgtgttcaga ttgtggagga aaagtggccg ccattttaga cttgccgcat aactcggctt   960
agggctagtc gtttgtgcta agttaaacta gggaggcaag atggatgata gcaggtcagg  1020
cagaggaagt catgtgcatt gcatgagcta aacctatctg aatgaattga tttggggctt  1080
gttaggagct ttgcgtgatt gttgtatcgg gaggcagtaa gaatcatctt ttatcagtac  1140
aagggactag ttaaaaatgg aaggttagga aagactaagg tgcagggctt aaaatggcga  1200
ttttgacatt gcggcattgc tcagcatggc gggctgtgct ttgttaggtt gtccaaaatg  1260
gcggatccag ttctgtcgca gtgttcaagt ggcgggaagg ccacatcatg atgggcgagg  1320
ctttgttaag tggttagcat ggtggtggac atgtgcggtc acacaggaaa agatggcggc  1380
tgaaggtctt gccgcagtgt aaaacatggc gggcctcttt gtctttgctg tgtgcttttc  1440
gtgttgggtt ttgccgcagg gacaatatgg caggcgttgt catatgtata tcatggcttt  1500
tgtcacgtgg acatcatggc gggcttgccg cattgttaaa gatggcgggt tttgccgcct  1560
agtgccacgc agagcgggag aaaaggtggg atggacagtg ctggattgct gcataaccca  1620
accaattaga aatgggggtg gaattgatca cagccaatta gagcagaaga tggaattaga  1680
ctgatgacac actgtccagc tactcagcga agacctgggt gaattagcat ggcacttcgc  1740
agctgtcttt agccagtcag gagaaagaag tggaggggcc acgtgtatgt ctcccagtgg  1800
gcggtacacc aggtgttttc aaggtctttt caaggacatt tagcctttcc acctctgtcc  1860
cctcttattt gtcccctcct gtccagtgct gcctcttgca gtgctggata tctggctgtg  1920
tggtctgaac ctccctccat tcctctgtat tggtgcctca cctaaggcta agtatacctc  1980
ccccccacc ccccaacccc cccaactccc cacccccacc ccccaccccc cacctcccca  2040
cccccctacc cccctacccc cctacccccc tctggtctgc cctgcactgc actgttgcca  2100
tgggcagtgc tccaggcctg cttggtgtgg acatggtggt gagccgtggc aaggaccaga  2160
atggatcaca gatgatcgtt ggccaacagg tggcagaaga ggaattcctg ccttcctcaa  2220
gaggaacacc taccccttgg ctaatgctgg ggtcggattt tgatttatat ttatcttttg  2280
gatgtcagtc atacagtctg attttgtggt ttgctagtgt ttgaatttaa gtcttaagtg  2340
actattatag aaatgtatta agaggcttta tttgtagaat tcactttaat tacatttaat  2400
gagtttttgt tttgagttcc ttaaaattcc ttaaagtttt tagcttctca ttacaaattc  2460
cttaaccttt ttttggcagt agatagtcaa agtcaaatca tttctaatgt tttaaaaatg  2520
tgctggtcat tttctttgaa attgacttaa ctattttcct ttgaagagtc tgtagcacag  2580
aaacagtaaa aaatttaact tcatgaccta atgtaaaaaa gagtgtttga aggtttacac  2640
aggtccaggc cttgctttgt tcccatcctt gatgctgcac taattgacta atcacctact  2700
tatcagacag gaaacttgaa ttgctgtggt ctggtgtcct ctattcagac ttattatatt  2760
ggagtatttc aatttttcgt tgtatcctgc ctgcctagca tccagttcct ccccagccct  2820
gctcccagca aacccctagt ctagccccag ccctactccc accccgcccc agccctgccc  2880
cagccccagt cccctaaccc cccagcccta gccccagtcc cagtcctagt tcctcagtcc  2940
cgcccagctt ctctcgaaag tcactctaat tttcattgat tcagtgctca aaataagttg  3000
```

-continued

```
tccattgctt atcctattat actgggatat tccgtttacc cttggcattg ctgatcttca   3060
gtactgactc cttgaccatt ttcagttaat gcatacaatc ccatttgtct gtgatctcag   3120
gacaaagaat ttccttactc ggtacgttga agttagggaa tgtcaattga gagctttcta   3180
tcagagcatt attgcccaca atttgagtta cttatcattt tctcgatccc ctgcccttaa   3240
aggagaaacc atttctctgt cattgcttct gtagtcacag tcccaatttt gagtagtgat   3300
cttttcttgt gtactgtgtt ggccacctaa aactctttgc attgagtaaa attctaattg   3360
ccaataatcc tacccattgg attagacagc actctgaacc ccatttgcat tcagcagggg   3420
gtcgcagaca acccgtcttt tgttggacag ttaaaatgct cagtcccaat tgtcatagct   3480
ttgcctatta aacaaaggca ccctactgcg ctttttgctg tgcttctgga gaatcctgct   3540
gttcttggac aattaaagaa caaagtagta attgctaatt gtctcaccca ttaatcatga   3600
agactaccag tcgcccttgc atttgccttg aggcagcgct gactacctga gatttaagag   3660
tttcttaaat tattgagtaa aatcccaatt atccatagtt ctgttagtta cactatggcc   3720
tttgcaaaca tctttgcata acagcagtgg gactgactca ttcttagagc cccttccctt   3780
ggaatattaa tggatacaat agtaattatt catggttctg cgtaacagag aagacccact   3840
tatgtgtatg cctttatcat tgctcctaga tagtgtgaac tacctaccac cttgcattaa   3900
tatgtaaaac actaattgcc catagtccca ctcattagtc taggatgtcc tctttgccat   3960
tgctgctgag ttctgactac ccaagtttcc ttctcttaaa cagttgatat gcataattgc   4020
atatattcat ggttctgtgc aataaaaatg gattctcacc ccatcccacc ttctgtggga   4080
tgttgctaac gagtgcagat tattcaataa cagctcttga acagttaatt tgcacagttg   4140
caattgtcca gagtcctgtc cattagaaag ggactctgta tcctatttgc acgctacaat   4200
gtgggctgat cacccaagga ctcttcttgt gcattgatgt tcataattgt atttgtccac   4260
gatcttgtgc actaaccctt ccactccctt tgtattccag caggggaccc ttactactca   4320
agacctctgt actaggacag tttatgtgca caatcctaat tgattagaac tgagtctttt   4380
atatcaaggt ccctgcatca tctttgcttt acatcaagag ggtgctggtt acctaatgcc   4440
cctcctccag aaattattga tgtgcaaaat gcaatttccc tatctgctgt tagtctgggg   4500
tctcatcccc tcatattcct tttgtcttac agcagggggt acttgggact gttaatgcgc   4560
ataattgcaa ttatggtctt ttccattaaa ttaagatccc aactgctcac accctcttag   4620
cattacagta gagggtgcta atcacaagga catttctttt gtactgttaa tgtgctactt   4680
gcatttgtcc ctcttcctgt gcactaaaga ccccactcac ttccctagtg ttcagcagtg   4740
gatgacctct agtcaagacc tttgcactag gatagttaat gtgaaccatg gcaactgatc   4800
acaacaatgt ctttcagatc agatccattt tatcctcctt gttttacagc aagggatatt   4860
aattacctat gttacctttc cctgggacta tgaatgtgca aaattccaat gttcatggtc   4920
tctcccttta aacctatatt ctaccccttt tacattatag aaagggatgc tggaaaccca   4980
gagtccttct cttgggactc ttaatgtgta tttctaatta tccatgactc ttaatgtgca   5040
tattttcaat tgcctaattg atttcaattg tctaagacat ttcaaatgtc taattgatta   5100
gaactgagtc ttttatatca agctaatatc tagcttttat atcaagctaa tatcttgact   5160
tctcagcatc atagaagggg gtactgattt cctaaagtct ttcttgaatt tctattatgc   5220
aaaattgccc tgaggccggg tgtggtggct cacacctgta atcccagcac tttgggaggc   5280
tgaggtggga agatccctta ctgccaggag tttgagacca gcctggccaa cattaaaaaa   5340
aaaaaaaagt aagacaattg ccctggaatc ccatccccct cacacctcct tggcaaagca   5400
```

-continued

```
gcaggagtgc taactagcta gtgcttcttc tcttatactg cttaaatgcg cataattagc   5460

agtagttgat gtgcccctat gttagagtag aatcccgctt ccttgctcca tttgcattac   5520

tgcaggagct tctaactagc ctgaattcac tctcttggac tgttaatgtg catacttata   5580

tttgctgctg tacttttta ccatgtaagg accccaccca ctgtatttac atcccagctg   5640

gaagtaccta ctacttaaga cccttagact agtaaagtta gcgtgcataa tcttaggtgt   5700

tatatacaca ttttcagttg catacagttg tgccttttat caggactcct gtacttatca   5760

aagcagagag tgctaatcaa tattaagccc ttctcttcga actgtagatg gcatgtaatt   5820

gcagttgtca atggtccttc aattagactt gggtttctga cctatcacac cctctttgct   5880

ttattgcatg gggtactatt cacttaaggc ccctttctca aactgttaat gtgcctaatg   5940

acaattacat cagtatcctt ccttttgaag gacagcatgg ttggtgacac ctaaggcccc   6000

atttcttggc ctcccaatat gtgtgattgt atttgtcgag gttgctatgc actagagaag   6060

gaaagtgctc ccctcatccc cacttttccc ttccagcagg aagtgcccac cccataagac   6120

ccttttattt ggagagtcta ggtgcacaat tgtaagtgac cacaagcatg catcttggac   6180

atttatgtgc gtaatcgcac actgctcatt ccatgtgaat aaggtcctac tctccgaccc   6240

cttttgcaat acagaagggt tgctgataac gcagtcccct tttcttggca tgttgtgtgt   6300

gattataatc gtctgggatc ctatgcacta gaaaaggagg gtcctctcca catacctcag   6360

tctcaccttt cccttccagc agggagtgcc cactccataa gactctcaca tttggacagt   6420

caaggtgcgt aattgttaag tgaacacaac catgcacctt agacatggat ttgcataact   6480

acacacagct caacctatct gaataaaatc ctactctcag acccctttttg cagtacagca   6540

ggggtgctga tcaccaaggc ccttttttcct ggcctggtat gcgtgtgatt atgtttgtcc   6600

cggttcctgt gtattagaca tggaagcctc ccctgccaca ctccaccccc aatcttcctt   6660

tcccttccgg cagggagtgc cctctccata agacgcttac gtttggacaa tcaaggtgca   6720

cagttgtaag tgaccacagg catacacctt ggacattaat gtgcataacc actttgccca   6780

ttccatctga ataaggtcct actctcagac cccttttgca gtacagcagg ggtgctgatc   6840

accaaggccc cttttcttgg cctgttatgt gcgtgattat atttgtctgg gttcctgtgt   6900

attagacaag gaagccttcc ccccgccccc accccccactc ccagtcttcc tttcccttcc   6960

agcagggagt gccccctcca taagatcatt acatttggac aatcaaggtg cacaattata   7020

agtgaccaca gccatgcacc ttggacatta ttggacatta atgtgcgtaa ctgcacatgg   7080

cccatcccat ctgaataagg tcctactctc agatgccctt tgcagtacag caggggtact   7140

gaatcaccaa ggcccttttt cttggcctgt tatgtgtgtg attatattta tcccagtttc   7200

tgtgtaatag acatgaaagc ctcccctgcc acaccccacc tccaatcttc ctttcccttc   7260

caccagggag tgtccactcc atatacccttt acatttggac aatcaaggtg cacaattgta   7320

agtgagcata ggcactcacc ttggacatga atgtgcataa ctgcacatgg cccatcccat   7380

ctgaataagg tcctactctc agaccctttt tgcagtacag caggggtgct gatcaccaag   7440

gccccttttc ctggcctgtt atgtgtgtga ttatatttgt tccagttcct gtgtaataga   7500

catggaagcc tcccctgcca cactccaccc ccaatcttcc tttcccttct ggcaggaagt   7560

acccgctcca taagaccctt acatttggac agtcaaggtg cacaattgta tgtgaccaca   7620

accatgcacc ttggacataa atgtgtgtaa ctgcacatgg cccatcccat ctgaataagg   7680

tcctactctc agacccctttt tgcagtacag taggtgtgct gataaccaag gcccctcttc   7740

ctggcctgtt aacgtatgtg attatatttg tctgggttcc agtgtataag acatggaagc   7800
```

```
ctcccctgcc ccaccccacc ctcaatcttc ctttcccttc tggcagggag tgccagctcc   7860
ataagaacct tacatttgga cagtcaaggt gcacaattct aagtgaccgc agccatgcac   7920
cttggtcaat aatgtgtgta actgcacacg gcctatctca tctgaataag gccttactct   7980
cagacccctt ttgcagtaca gcaggggtgc tgataaccaa ggcccatttt cctggcctgt   8040
tatgtgtgtg attatatttg tccaggtttc tgtgtactag acaaggaagc ctcctctgcc   8100
ccatcccatc tacgcataat ctttcttttc ctcccagcag ggagtgctca ctccataaga   8160
cccttacatt tggacaatca aggtgcacaa ttgtaagtga ccacaaccat gcatcttgga   8220
aatttatgtg cataactgca catggcttat cctatttgaa taaagtccta ctctcagacc   8280
ccctttgcag tatagctggg gtgctgatca ctgaggcctc tttgcttggc ttgtctatat   8340
tcttgtgtac tagataaggg caccttctca tggactccct ttgcttttca acaaggagta   8400
cccactactt tttaagattc ttatatttgt ccaaagtaca tggttttaat tgaccacaac   8460
aatgtccctt ggacattaat gtatgtaatc accacatggt tcatcctaat taaacaaagt   8520
tctaccttct caccctccat ttgcagtata ccagggttgc tgacccccta agtccccttt   8580
tcttggcttg ttgacatgca taattgcatt tatgttggtt cttgtgccct agacaaggat   8640
gccccacctc ttttcaatag tgggtgccca ctccttatga tctttacatt tgaacagtta   8700
atgtgaataa ttgcagttgt ccacaaccct atcacttcta ggaccattat acctcttttg   8760
cattactgtg gggtatactg tttccctcca aggccccttc tggtggacta tcaacatata   8820
attgaaattt tcttttgtct ttgtcagtag attaaggtca taccccatca cctttccttt   8880
gtagtacaac agggtgtcct gatcaaccaa agtcctgttg ttttggactg ttaatatgtg   8940
caattacatt tgctcctgat ctgtgcacta gataaggatc ctacctactt tcttagtgtt   9000
tttagcaggt agtgcccact actcaagact gtcacttgga atgttcatgt gcacaaactc   9060
aattctctaa gcatgttcct gtaccacctt tgctttagag caggggggatg atattcacta   9120
agtgcccctt cttttggact taatatgcat taatgcaatt gtccacctct tcttttagac   9180
taagagttga tctccacata ttccccttgc atcaggggca tgttaattat gaatgaaccc   9240
ttttctttta atattaatgt cataattgta tttgtggacc tgtgtaggag aaaaagaccc   9300
tatgttcctc ccattaccct ttggattgct gctgagaagt gttaactact cataatctca   9360
gctcttggac aattaatagc attaataaca attatcaagg gcactgatca ttagataaga   9420
ctcctgcttc ctcgttgctt acatcggggg tactgaccca ctaaggcccc ttgtactgtt   9480
aatgtgaata tttgcaatta tatatgtctc cttctggtag agtgggatat tatgccctag   9540
tatccccttt gcattactgc aggggctgct gactactcaa aacttctcct gggactgtta   9600
ataggcacaa tggcagttat caatggtttt ctccctccct gaccttgtta agcaagcgcc   9660
ccaccccacc cttagtttcc catggcataa taaagtataa gcattggagt attccatgca   9720
cttgtctatc aaacagtggt ccatactccc aacccttttg cattgcgcca gtgtgtaaaa   9780
tcacaggtag ccatggtgtc atgctttata tacgaagtct tccctctctc tgccccttgt   9840
gtgcccttgg cccctttttta cagactattg ctcacaatct caggtgtcca tatttgcagc   9900
tattaggtaa gattgtgctg tctccctctt cccttccctc tgccctgccc cttttgcctc   9960
tttgctgggt aatgttgacc agacaaggcc ctttctcttg gacttaaaca attctcagtt  10020
gcactttcct tggtcccacc cattatacat gaacccctct acttcctttc gcattgcttc  10080
tgagtatgct gactacccaa agccccttct gtgttattaa taaacacagt actgattgtc  10140
ccatttttca gcccatcagt ccaagatctc cctaccactt tggtgtgttg gtgcagtgtt  10200
```

-continued

```
gactatgaaa agcaggcctg aactaggtgg ataagccttc actcattttc tttcatttat  10260
taatgatcct agtttcaatt attgtcagat tctggggaca agaaccattc ttgcccacct  10320
gtgttactgc tttactgtgc aaaatactga aggcaagtca gacccaggga gctggattgc  10380
catcctttat tttgtgtttc cagtgtacac tataaaattg tctccccagg aaggaaggtt  10440
ggcactttct ctgcattctt ctttccagag cagattgcct ggttaagaat ctcttgttgt  10500
ccccttgta tattgttatt gtaaagtgcc aaatgccagg atacagccag aaaaattgct  10560
tattattatt aaaaaaattt ttttaagaaa gacatctgga ttgtagggtg gactcgataa  10620
cctggtcatt attttttga agccaaaata tccatttata ctatgtacct ggtgaccagt  10680
gtctctcatt ttaactgagg gtggtgggtc tgtggataga acactgactc ttgctatttt  10740
aatatcaaag atattctaga gtggaactct taagaccagt atctttgtgt gggctttacc  10800
agcattcact tttagaaaaa ctacctaaat tttataatcc tttaatttct tcatctggag  10860
cacctgcccc tacttatttc aagaagattg cagtaaaacg attaaatgag ggaacatatg  10920
cagaggtgct tttaaaaagc atatgccacc tttttatta attattatat aaaatgaagc  10980
atttaattat agtaataatt tgaagtagtt tgaagtacca cactgaggtg aggacttaaa  11040
aatgataaga cgagttccct attttataag aaaaataagc caaaattaaa tattcttttg  11100
gatataaatt tcaacagtga gatagctgcc tagtggaaat gaataatatc ccagccacta  11160
gtgtacaggg tgttttgtgg cacaggatta tgtaatatgg aactgctcaa gcaaataact  11220
agtcatcaca acagcagttc tttgtaataa ctgaaaaaga atattgtttc tcggagaagg  11280
atgtcaaaag atcggcccag ctcagggagc agtttgccct actagctcct cggacagctg  11340
taaagaagag tctctggctc tttagaatac tgtaagtact acttcgtagc tattaagtaa  11400
tctttttcct attctatttt ctttctctta gatgccacct atagaaaagt cagagggtcc  11460
agtaagtttc tttccttctt cccacctcat ctgcaatata tatatataga gagagaaata  11520
gatacataca tacatgcata aatacacata tgtgagttaa ccagcagaac tgtagaatta  11580
atattgtgga cccagctcta tgctaggtta cactgataac ctgggtagga atgatatcat  11640
cctatataat ttcattcctg agatgatttt atcgttgagg agctaatgtg agcacatttg  11700
aaataacttt agaaaataat aagtgctgtt ttgtgtgaat cataagtagt agttttagga  11760
agggaaccca caaggatttg aagttgatag aataaactta aggaagtggg tttgcttttt  11820
ctctttaagc caagatagga ttaatattgc agccatctgg atagtccagt tggtttattt  11880
taatttcatt tgttttttac ctcttttgga gccatggaaa gagatgaaag ggatagagca  11940
tagccattgt gtttggctat ttgcgaaggt tggcaaatta gtgattgcta aatctcataa  12000
gcttgagtat tttaaagttc agagattgag ggcataaatc taatacttcg gctccttcca  12060
caattttact acatttctgc ccaagaacag atgaccatgg ataatgcata tcgtagatac  12120
tttttaagtt tggaaccttt ttgccaagag ggtagtggag aagtgaagtc aaaaccttga  12180
ccttccttgc ctactttatg ctgtagttta tataccttct ttcctcccac ctttcgtaaa  12240
gctaaaagaa gcttagcctc cttaatgttt tccagctgac aaaatattgt ttaacataac  12300
attcgaaact ttttttctgg tgcacattca tgcatcacag caggagcaac aagaaccata  12360
taagtgaact ggcttcactt atagcccgtt ttaattcata tccatatttc ctcagggctt  12420
gtttccatgc ctcccagccc cactccatat gcttaacaac attgtctggc tgactgaggg  12480
ttatatacat catggtcttg aaccttcttg gaaacatggt ctgtgccatt gtttctcaaa  12540
cccaagtaat gcttcatgat gaaacacctt ctaaaggaac aaaattttct gagatcctaa  12600
```

```
aaaaatgtgt tttgaggaac actgacttaa caaagatatt tgaaatgtaa atatgttttc  12660
caatttcacg ttgtctttgt caaagatgtg ttttatataa cttatgtaga acttggggat  12720
ccattagaat atattcacaa atccccaggg ttatcacccc aatttgagaa accctggtct  12780
atgcttatga aatcttctat tggtaattaa attgtcattc attgtcaaca tacaattata  12840
attattattg gaatttgttt taaatgaatg aatttggagg tgattctgta ccttaagtca  12900
agaggaagga tggcttgatt ttaggtggat tgattatact agatagcatc caaaggtgaa  12960
tcttgaagct gtatttaaat tcattgcttg aaataatttc caccccttaag aaaaatctct  13020
agcaattgta aaaagggatg ctctggaaat gtgggcatct tcaaaataga gataattctt  13080
gtgttagttc aacaaatatt attgtaccag gtgctggaat aaatagcaaa accaaagaca  13140
ggatttatat caaggaattt gctttcttat ggaggatgca gaaggaaatc attatggttt  13200
tgggcagaaa tgcttagact ttagtcctgg ctctgagttt ggttcagatc accatcaatc  13260
tgaccatctc gagactgcta gtgaaataag ataggggctt atatcaaata cctaaatccc  13320
tgaaaatgac attttgtgat ttggaaaatt ttcaaaagtc taatgaagga aacttttttg  13380
gcatttcttt aaatgattat tgtcatttct tttctgactt ttccctttat aaaaccttaa  13440
catgtaggat tggaggaagt tttctgacca ttttctcata tcctctttca gctttatctt  13500
tctgtaactt ccatttctct agccacctcc ctaaattaca gaagactgtg agacccaggg  13560
ctgctgtgat taggcattca taatttcttt tcagggtgtt tgtgccctga ttatcaaatg  13620
tacagcttga agggagttca tgtcttaaag taatgaatta agagttgacc tttgttgact  13680
gctaaaatat tcttatatgt gaaagcatcc tggaaaaata cgttaccagc ttaaagagaa  13740
agaaactaat gattatatct gaactgagct aatgcctctt ctcttccccc aaaccttatc  13800
agtttggatg gcaaagagta atgatgtgtc agttaaacag agctaatgcc ttcctctgcc  13860
ttgtcttaaa gactggattg ggagaaaatt gatattctca ctaccatatt ttgggctgta  13920
ggcaagtagc attttacaca ggtttccttc aaaaatccaa ctcaagttgg agctcatgta  13980
tttaagacat agctggcctg ctgaatttaa caagttaaac ttcagtggcc atgtacagtt  14040
atatatcact atatatatgt gtattaggct gtcgagttgg tcatgttttt gttggtgact  14100
taggctttac ttgatagctc ttccttgacc tttccaaatt gagtactgat acatggagct  14160
tgggcttctt ctgcatctta tacaaatgag tttggtaaag aagcctctcc tttactgttt  14220
tgatgtttat attagaaata acttttgatt atttttttc atgttaggat gagaaactga  14280
aacaaaatgt aaatttgacc ggtgctagac ttcttaaatt atgggtagac ttaaagtatt  14340
attttcctta accaattaga atgctagtct tctagtgttc ccggaaacat gagaggttat  14400
gcagtagacc caagcaatac cctcttatta cataatcaag tgcgtataag aatttaaaaa  14460
tagggatatg actggaacat cactgtactt taccaggtcc cattataaaa ttatctatgt  14520
tactttaccc atagctttga aaactagtgg catagtatat tttatagtat gctgttagtg  14580
tgattggcat tgaacagtga tgggatataa tcactctaca atctatatgt tattaaagtt  14640
ttccagcctt atagatctcc cttgactgaa aattagctac taacttacga cttatttttt  14700
acagcagatt gactaggtct ttccaggaaa tctgttgatg tacaaaaaca aagtttaatt  14760
gctaatgttt ttttaaaaaa taactttttg atattacgga tacctggtta tttgggcctt  14820
gtatatttta acatcaaaat tacctattat aaatccatat aaacagaaaa gaaagagagt  14880
aagtctttag atcagatctg caaacaatga tggtacgtac tgtagaaaaa tctggaacat  14940
agacttacca gttcttaggt tccattttgc ttgcttttta aaaactgtgt cttataagtc  15000
```

```
ttcagcaact ggttgggaga tttttagaaa aaataacctt ttaatgttag aacagtgtag  15060
agatttacag aatgattctg aagatagagt ttctgtgtac ttcacaccca gtttttccca  15120
gtgttaacat tttacattag tttggtacat ttgtcacaac aaaccaatat tgatacatta  15180
ttattaacta gagtccatat tttattcaga tttccttagt ttttccttaa tgttcttttt  15240
gtgttccagg atcccattga agataccacg ctgcatgtgt ccttagtagt catgtctcct  15300
taggctcctc ttggtaatga cagtttctca gactctttgt ttttgatgaa cttcacagtt  15360
ttgaggacta atggtccagt attctataga atgtctctct attggaattt gtctgatgtt  15420
cttctcatga ctagattggg tttatgagtg tttaggagga agaccacaaa ggtagagtgc  15480
cattcttatc acttatcaag agtacatact atcaacatga cttatcactg tttatgttat  15540
ccttaatcac ctgtctgagg tactatttgt caggtttctc cagcgtaaaa ttagtcttta  15600
tttctccatt tccctactat actgttcaca taggaagtca ctatgtgcag ccagcactta  15660
aggaatggga aattaccttc cacctcattg agggcagagt atttacataa attatttgga  15720
attcttttgc acaggatgtc ttttctccac aatgtattgt gtttattcag tcatttatat  15780
cagtatgatc tcagggatat tttatactct gggttataat acagtattac tttattctgt  15840
tgttcaaatt gttccagctt tggccattgg gaggtctttc atttggcttt gatataaccc  15900
catgaatgtg ggtttttttgt ttgagcactt tcttattttt ggaactacaa catgcttcag  15960
actcatttgc atatctcctg cctggaccta aaatgatgta tttctgcaag gagccttgat  16020
actttttatt ggagagtaat attagaaatc aagaagtgaa tgctaggtgc gctcattact  16080
actggagtgt cattccttca agaccttttc agttgacaag agcaaggaga tatatatttg  16140
cattctaacg tgtgtatatg cacatagcta taaatatata taaccatctg tatctatatt  16200
aaactaaatg tgtttatacc tacgtctcca actctaatca ttgccacatg gatcattata  16260
gtctcacctc cttgcttatc tgttacctcc catttctaca gtgagaaacc tggcttggtt  16320
gggaaatttt tctgttaata ttacggtagt gagtgtttga catttgcttc tatggttaag  16380
tttagggaga gtttagctgt agggtattct tgaaactaga aatgaccctt ctgccctaaa  16440
tgtttctgcc agttttgaaa cgtaaaatag gttgcagaaa caaactttat cttaagaacc  16500
agaatttact tcaatccaca ttttgacatt gattttcaga ttaaattatt ctgatatcgc  16560
caggtaagct gttccttggg tatgcatttc ttctttccgt ttttttctaa gagctaaagg  16620
accctgagaa cactggaggt gggaaaggaa gggaaaggca tgttcacacg tgggatagga  16680
aaggttcatt tactgacctc cagctagcct tccaaagtgc ctatttaaga cccaaggagt  16740
agatgtcttc cttggcaatt gtaacccaaa tataattttt aacctttcaa ttttagtcaa  16800
gaaagttggt gtgctgttac aaaaagtgcc ctgattaaca gcattgtcat gtgcattgca  16860
tattaatcag caatttaaaa taacatgaaa ttatgttgag tataatttta atattttata  16920
ttagatatta gtttgagaca gtgtttctca agtctgtata ataagtttga tagtagggag  16980
gttttctctc aagaaaagaa ttattcagtg tgcacctaca taatcactgc ttagattcta  17040
caattaatat tttgctatat ttgattaaac gttttctgta aaagaaaaat attattatgt  17100
actatttagg tttatgggaa taattgttaa gttaaagtgt atgaacaaac ctggaatgaa  17160
atctgtttgc ctacatctat aatacaacta taaaacatag cagatgtaca aattagtagt  17220
taatagataa ctaaaatgca aatatggcac tactattata gtattatagt ttcttttgag  17280
tggcgtgtct gtaatatcac atgctgtgtt gatgcacttc accaaactgc tgttttcaaa  17340
ctgctttaaa tcctgccatt atagcacata gcaatgctat ttcactttca tttggcacaa  17400
```

```
aacacattta tatattgttt gcttctcttc ttttctgtaa tccccaggca acaaaactag  17460
aacatttgcc actaatctgg caacgtggtc ctatattatg aagtagtcat atagctgatc  17520
taaactatcc ttacagtgaa atgagagtat tgtgaaagtt ttgtagaaag ctccccatat  17580
gtcctgagaa tctatgcaca gaccccacag ttaaaagacc tttgaattgt gggaagacat  17640
gggtttaagt atcacttggt taccttctat ttgtgtaaca ttgaggtagt ttcatcttct  17700
gggttcccag tttccttaga gaatgaaaat gttgaattat gtgatttttt tttttttttg  17760
agacggagtt ttgctctttc gcccaggctg gagtgaagta gcacgatctc gactcactgc  17820
aacctccttc ccccatgatc aagcaattct cctgcctcag cctcccaagt agctgggatt  17880
acaggcaccc gccccccacc ccccgccccc agctaatgtt tgtattttta gtacagatgg  17940
agttttgccg tgttggccag gctggtctcg aacttctgac ctcaggtgat ccactcgcct  18000
tggcctccca aagtgctagg attacaggca tgagccactg cgcctggcct atgtgattat  18060
taatatcacg tctagctgtg acaattctgt ctgatgctgg agtatttgaa ccagatggct  18120
ggctgtgcca ctcagttatt ctctccataa gactttgata ttttgttggt ctgcaagatg  18180
acggattctc aaaattcttg tcagtgaata ttgaacccta gtgaaatgta tggttctgta  18240
tcagttccaa aatgtaacca ctttctctag ccttagattc ccagttccaa aatgtaacca  18300
ttttctctag ccttagattc ccgttaaggg aaagggaatg ctctttgagt atgtcatcac  18360
catagtaaca ggcaaaacta gagggctttg atgctaaagc aagatactcc ataaatatgc  18420
ttaagaagac ttggggagac tggaatagtt gttccctttt agatgccagt gtataaatga  18480
atttgagcta ggatccgttt atttaaaatt tctttaggtg tatttgcttg catatggagt  18540
gcacatttac tctcattaat ggagttttag gaagcagtag agtaaatgca taaacatgta  18600
tgaaccgcca tgtttaactg gaagcctgca tttggaagtc aagtatctaa tcttagatta  18660
aattaggatg gggaaggatg ttggcaagag attttgaagc ttgttctgct tatattgaga  18720
acatcataga acagtttggc ctttttaaag ctagagaata gtgttgaata agtgatgttc  18780
catatattcc tgtttgacat tgacataaag gtttcctcat gatacagtaa tccctgatca  18840
gggatctgga agcctgtatt catttaaggt actcaggttt aacatactgg gtgcttttca  18900
caccatacta tacagtacca tgcaaagtgc tttcaagact gcaaatttgg cttagatccc  18960
ctttagtgag ctcctatgct atagtaaagg tagatagcca attattaaaa acagtcaaga  19020
caattgcacc tctaagcagt agtagcagtt gccacaccac cttgaatctt gaagtatttt  19080
cagcaacagg atgaccatta gccacaaatt tagtgtcagc ccttaaggtc ggtattggtt  19140
tgacccatat tttcatgtag ttctttttct tcacttgtct aatcttcccg tgtactgcca  19200
gggcttgtca ttagaggact ttagggagac caagcaggct agaaagtaga gacaggagat  19260
acctatgtct aatgcttcag tttatacttc ctaggttttt ttcattgggg tttttgtaac  19320
tcttttggta tcctaccggt gctttggtag cctactgaac cctgtctttc ttcttaagga  19380
cattctgagc atgtgagacc tgaggactgc aaacagctat aagaggctcc aaattaatca  19440
tatctttccc tttgagaatc tggccaagct ccagctaatc tacttggatg ggttgccagc  19500
tatctggaga aaaaggtagt ttggggaatt tattgttgta gtgcttctgt ctttggattg  19560
aacttcccac aactctcctt tttaaagcag aacacagctg ggcatggtgg ctcctgcttg  19620
taattccagg gctttgggag gttgaggtgg ggggatcact tgaggccagg agttgaagac  19680
ccatgtctct acaataaaat aaaattagtt gggcatggtg gtacgtgcct gtagtcctac  19740
ctactctgga ggctgaggca gcaggattgc ttgagcccag gagttcaagg ctgcagtgag  19800
```

```
ccatcattag ccactgcact ccagcctagg tggcagagcg ggacccagtc tcttaaaaag  19860
aaagaaaagc agaacgtgag ccagttttca tcaattccta tactttttct tttgcatgta  19920
cacatacatt ttaactttac ataatgagtt cggcctgttt catttatccc tcagagctgg  19980
gctccagtga ggtctgtaag ggcaagcata cttgatcccc aatgaagaat gagagatgca  20040
aagcactaaa ttatttcttt tctcaccaca cagcaagata gatttaatga acttaacacc  20100
ttttgattag tggcctttta aattattccc actttccttt ggcagatggg tattaagttc  20160
tcaggatttg tttacaaata agactaactt catctgtatt agctcagttt tggtaggcct  20220
aattccatta tcactgccat ttccttgttt taagaaatca aaatttctta gcttgaaaaa  20280
caattgaaat tgttaaaaag tggaatagga gagccccggg ggcctgtata aggaatttac  20340
tgaatccctg gttttctgta ccttgttttt ccttctgcat agatttgctt aactgttttt  20400
gtggcgtgta tttttttttt ttcgcagttt cgctcttgtt gcccaggctg gagtgcaatg  20460
gcgcaatctc agctcactgc aacctctgtc tcctgggttc aagttattct cctgcctcag  20520
cctctcgagt agctgagatt acaggcatgc gcgaccacgc caggctaatt ttgtattttt  20580
agtagagacg gggtttctcc atgttggtca ggctggtctc aaactcctga cctcaggtga  20640
ttcacccgcc tcgacctccc aaactgctgg gattacaggc gtgagccacc acgcctggcc  20700
agctgttgtt ataactggag ttctatgtgc ttgtgaccat tcttggtttc tccgaatatc  20760
ctagaacttt ggtggcgccc tattatacag gttgttgaag aaatgttacc atgtggattg  20820
agtaggaaac aattctcttt atcttggcaa tattatggca tggcactact taaagtacaa  20880
attaaaagag gggatgcta cagaactagc tgacaggcac tttgatagag gtggatttct  20940
cagttcttaa aatagctctt tataaaggaa gccagaggca ttgtggagga gaattcttac  21000
ataactcata gggttagacc acatccgacc ttttctgtgt ggcttcatgg ctctcttggt  21060
tgagaaagca ttagtttctc cttccattag tttcaacctc ttgatttctt gacccccccta  21120
ctatattttg tgctgagaac acaagggtat taacaaccca cattgtagag gatcgctcag  21180
taataaagac tggagaataa aatgcagcat gggaatattg gcaattactc agttctaaat  21240
ttctcttgga aatgagggaa agcatacaga atagagctgg aatgaatagg ataatttttt  21300
ttttttttgc taagttggta gccagaatat aacagctccg cacaactgta aatgtccact  21360
cttcaatcca catgaagaaa agggtaaaaa tatggttgaa ctcaaccact agttgcccat  21420
tagaacagac tttcccagtg tactgcattt caatactttt tcttttatct cttttcagat  21480
cttcctcaga agaataggct tgttgtttta cagtgttagt gatccattcc ctttgacgat  21540
ccctaggtgg agatggggca tgaggatcct ccaggggaaa agctcactac cactgggcaa  21600
caaccctagg tcaggaggtt ctgtcaagat actttcctgg tcccagatag gaagataaag  21660
tctcaaaaac aaccaccaca cgtcaaggtg cgtaagctgt ccctaaaagc ataataagta  21720
gtcttaattt tgattttgtt ttccagtata cattgcactt agtgtttcac tgaggtcgta  21780
ttcatcatta ttctgcatat gatttggtaa aaacagcttc ctaactaacc tgggaagcaa  21840
ctgggtgtga gattaactgg ttaaagtgat gatgtaaaga gggtagcggg ttgcatgtgt  21900
tcgggtgttt ggagtgggac tatagcacgt ggcagaggct tacagctaag ttgttctttt  21960
aggagaacat ggacaactgt cacatcagtg acattgatca catgggcaaa tcattctgtt  22020
ccatgtggtc cccaaagtct ctcttaaagc cttacagaag aactttgcca atcatttaca  22080
tacttcagga tggcttggga tgccatggtg tataatacaa caagtgagag gtgtgtcttt  22140
ttatgctatg gttgctgatt gatggaagcc gcataaatac aaatggaaac ctgactaaaa  22200
```

```
atggcacaaa gttatctgtc atcaggcagg agctaaagaa ccaggaccct acattctcta  22260
ggtcagtgtt gggagaggct gattagcgag tgagaattgg cagataaagg tgaccattcg  22320
gtgcaataaa tcctgaacgt ataggctttg cccagcattc ttcgtaaata gtgggtagct  22380
ataaatttca tgaaatattt tcatgggtaa gaactcttga aatgttataa ttgactagaa  22440
atctctgtag atttagaaat agagagttac taacaaattg ttagaaagtc taggaactag  22500
aaagctaagt tgagagttat ctaggaagat ctatctattg tactcataat ctttagataa  22560
attctcctag ggccagtagt ctatgtgaat tttcttttc ttcttcttct tcttcttttt  22620
ttttgtattt tagctgcaat gttaaacaac ctatgtgaat tttcttattg tgagaatatt  22680
tgccttccag agtgactcac ctttatctca aagagcaata ttgtgagttt tgaaaatgct  22740
gctctaaggc tgtgttttgt tagtcctgag ccaggagact taaagcaaac ttgaggggtc  22800
ttaaaacatc gaagtgagcc ttaaacattg ggaagacctt atgtttttcc ctctcatatc  22860
tattattttt gtgatctcag ttattaatca tttaaaggga ctctttccta gctgattggc  22920
acttaaaaca ggatggaagt cttttttttt ttttttttt ttgagatgga gttttgctct  22980
tgttgcccag gctggagtgc aatggtgcaa tctcagctca ctgcaacctc tgcctcccgg  23040
gttcaagcga ttctcctgcc tcagcctccc aagtagctgg gattacagtc atgcaccacc  23100
acgcccggct aattttgtat ttttaataga gacggtgttt ctccatgttg gtcaggctgg  23160
tctcaaactc ctgacctcag gtgatccgcc cacctcaacc tcccaaagtg ctgggattat  23220
gggcgtgagc caccgcgccc ggcagttctg gtctttaact aaggtataag gctatgactg  23280
gtagtggtgt ctctagtgac tcatcaagtg atatttggca agacattttc ccatttatgc  23340
cagtttccta ttctgttgaa tgaggaaatt ttctctctaa agacctaaaa gttttgactt  23400
tataggtttc aaagttctgt ggaaacattt tctattgctt attaatttga atcttatgta  23460
actctagcac agtactcaat atttatggca tttacatggt ttatctcatg ttttttttata  23520
gctcttcatt gttcctatct gccaaatcat tatacttcct acaagcagtg cagagagctg  23580
agtcttcagc aggtccaaga aatttgaaca cactgaagga agtcagcctt cccacctgaa  23640
gatcaacatg cctggcactc tagcacttga ggatagctga atgaagtaag ttgttgatgt  23700
tgcagtcctg tgaggatcac ttcagaactg ttataacagc tgttttttgg gagctggtgt  23760
tggatggggt gtgttggtct aatgtgaagt ggggctaaat gtgagatgga aagatgacca  23820
gtcttccata ttactgactg ggttcactga agcaactcaa agacattatg gtcttcttac  23880
cagttgtatc acagaagaat ttagcctttg cttgtgtgtt ctatgtcttc actgtatagg  23940
ccctctgtca ttcttagagc cttaaacgtt gagaagctta aaacaccatt tctgctttct  24000
gctgaaaggg taaccctttc tcatctccgt ttgtgagaga ctctgtcgtc agttaagatt  24060
agtgtaaaaa gaaaactaaa ctctgaagta gccattataa aagtgtgaga atgaagtcag  24120
ttttctaaag agttggggaa aggtgatgct aaaggagggg attgagcaag tcctatcaaa  24180
gagcctttta tgaaaatact tagtcatctg tgacatccca tttggctctt ccagaaatcc  24240
tagtaaatag ttgtaacagg atgttaagag gcatacattg tgtgttttaa atcctctgct  24300
actcattagg tatatgacct ttgacaactt aaagtctcta gacttctctg tttgtgaggg  24360
ttaaatgaaa tcatgtatgt aaagtgctca cctattgcag tgcctggcac atgtcaagta  24420
aaaggtaacc caagaagact cataagttca tttcccacaa tataagtgac cactagcact  24480
atcaggtagc aggcagagtt ggcatgcttt ggttctatgt aagaaatccc taaggtaaaa  24540
gtttataaat agaagagcat ctgtgttggt attggtggtt gttattattg tagtactata  24600
```

```
agtagtattc gtagtaacaa tagtttatta taattactaa tgacactttt tgattttttt  24660
tatctttctg tgatgctttt catgcctctt gtgcccctca ctgtatcttg cctcttctac  24720
tacttacttc ctctgaatgt ctgcctttgc ttatctcttg cactcaagtg tgtatttctt  24780
tgtctctttc tttcttgtct ttgctctttg ttctctatct aaagtgtgtc ttacccattt  24840
ccatgtttct cttgctaatt tctttcgtgt gtgcctttgc ctcattttct ctttttgttc  24900
acaagagtgg tctgtgtctt gtcttagaca tatctctcat ttttcatttt gttgctattt  24960
ctctttgctc tcctagatgt ggctcttctt tcacgcttta tttcatgtct cctttttggg  25020
tcacatgctg tgtgcttttt gtccttttct tgttctgtct acctctcctt tctctgccta  25080
cctctctttt ctctttgtga actgtgatta tttgttaccc cttccccttc tcgttcgttt  25140
taaatttcac ctttttttctg agtctggcct cctttctgct gtttctactt tttatctcac  25200
atttctcatt tctgcatttc ctttctgcct ctcttgggct attctctctc tcctccccctg  25260
cgtgcctcag catctcttgc tgtttgtgat tttctatttc agtattaatc tctgttggct  25320
tgtatttgtt ctctgcttct tccctttcta ctcacctttg agtatttcag cctcttcatg  25380
aatctatctc cctctctttg atttcatgta atctctcctt aaatatttct ttgcatatgt  25440
gggcaagtgt acgtgtgtgt gtgtcatgtg tggcagaggg gcttcctaac ccctgcctga  25500
taggtgcaga acgtcggcta tcagagcaag cattgtggag cggttcctta tgccaggctg  25560
ccatgtgaga tgatccaaga ccaaaacaag gccctagact gcagtaaaac ccagaactca  25620
agtagggcag aaggtggaag gctcatatgg atagaaggcc caaagtataa gacagatggt  25680
ttgagacttg agacccgagg actaagatgg aaagcccatg ttccaagata gatagaagcc  25740
tcaggcctga aaccaacaaa agcctcaaga gccaagaaaa cagagggtgg cctgaattgg  25800
accgaaggcc tgagttggat ggaagtctca aggcttgagt tagaagtctt aagacctggg  25860
acaggacaca tggaaggcct aagaactgag acttgtgaca caaggccaac gacctaagat  25920
tagcccaggg ttgtagctgg aagacctaca acccaaggat ggaaggcccc tgtcacaaag  25980
cctacctaga tggatagagg acccaagcga aaaaggtatc tcaagactaa cggccggaat  26040
ctggaggccc atgacccaga acccaggaag gatagaagct tgaagacctg gggaaatccc  26100
aagatgagaa ccctaaaccc tacctctttt ctattgttta cacttcttac tcttagatat  26160
ttccagttct cctgtttatc tttaagcctg attcttttga gatgtacttt ttgatgttgc  26220
cggttacctt tagattgaca gtattatgcc tgggccagtc ttgagccagc tttaaatcac  26280
agcttttacc tatttgttag gctatagtgt tttgtaaact tctgtttcta ttcacatctt  26340
ctccacttga gagagacacc aaaatccagt cagtatctaa tctggctttt gttaacttcc  26400
ctcaggagca gacattcata taggtgatac tgtatttcag tcctttcttt tgaccccaga  26460
agccctagac tgagaagata aaatggtcag gttgttgggg aaaaaaaagt gccaggctct  26520
ctagagaaaa atgtgaagag atgctccagg ccaatgagaa gaattagaca agaaatacac  26580
agatgtgcca gacttctgag aagcacctgc cagcaacagc ttccttcttt gagcttaggt  26640
gagcaggatt ctggggtttg ggatttctag tgatggttat ggaaagggtg actgtgcctg  26700
ggacaaagcg aggtcccaag gggacagcct gaactccctg ctcatagtag tggccaaata  26760
atttggtgga ctgtgccaac gctactcctg ggtttaatac ccatctctag gcttaaagat  26820
gagagaacct gggactgttg agcatgttta atactttcct tgattttttt cttcctgttt  26880
atgtgggaag ttgatttaaa tgactgataa tgtgtatgaa agcactgtaa aacataagag  26940
aaaaaccaat tagtgtattg gcaatcatgc agttaacatt tgaaagtgca gtgtaaattg  27000
```

```
tgaagcatta tgtaaatcag gggtccacag tttttctgta aggggtcaaa tcataaatac  27060
tttagactgt gggccatatg gtttctgtta catatttgtt ttttaaacaa cgtttttata  27120
aggtcaaaat cattcttagt ttttgagcca attggatttg gcctgctgtt catagcttac  27180
caccccctga tgtattattt gttattcaga gaaaatttct gaatactact agtttccttt  27240
tctgtgcctg tccctgtgct aggcactaaa aatgcaatga ttattgatat ctaggtgacc  27300
tgaaaaaaaa tagtgaatgt gctttgtaaa ctgtaaagca cttgtattct actgtgataa  27360
gcgttgtgga tacaaagaaa ggagcaagca taaaaaagtg ctctttcaaa aggatatagt  27420
actatgcaga cacaaggaat tgtttgataa atgaataaat tatatgtata tttgaggcca  27480
atttgtgttt gctgctctgg taattttgag taaaaatgca gtattccagg tatcagaaac  27540
gaaaacacat ggaaactgct tttaaacttt aaaatatact gaaaacataa gggactaagc  27600
ttgttgtggt cacctataat gtgccagata ccatgctggg tgctagagct accaaagggg  27660
gaaaagtatt ctcatagaac aaaaaatttc agaaaggtgc atattaaagt gctttgtaaa  27720
ctaaagcatg atacaaatgt caatgggcta catatttatg aatgaatgaa tggatgaatg  27780
aatattaagt gcctcttaca taccagctat tttgggtact gtaaaataca agattaattc  27840
tcctatgtaa taagaggaaa gtttatcctc tatactattc agatgtaagg aatgatatat  27900
tgcttaattt taaacaatca agactttact ggtgaggtta agttaaatta ttactgatac  27960
atttttccag gtaaccagga aagagctagt atgaggaaat gaagtaatag atgtgagatc  28020
cagaccgaaa gtcacttaat tcagcttgcg aatgtgcttt ctaaattata aagcacttgt  28080
aaatgaaaaa tttgatgctt tctgtatgaa taaaactttc tgtaagctag gtattgtctc  28140
tacaaaattc tcattgtata gttaaaccac agtgagaagg gttctataag tagttataca  28200
aaccaagggt ttaaatacct gttaaataga tcaattttga ttgcctacta tgtgaactca  28260
ctgttaaagg cactgaaaat ttatcatatt tcatttagcc acagccaaaa ataaggcaat  28320
acctatgtta gcattttgtg aactctaagg caccatataa atgtaactgt tgattttctc  28380
acttggtgct gggtactagg tttataaaat tgtatgatag ttattatatt gtgcaaataa  28440
agtaggaaaa tttgaataac aatgattatc ttttgaatac gcatacgcaa gggattggtt  28500
gtctgaagaa tgccactata gtagttatct attgtgtgcc aatctcattg ctaggcattg  28560
gggatgcaaa gataaaccat ctttattgtg tcttgggtag cagaagaaaa tatgtgtaaa  28620
atcaatttat aatttgtaaa ctgccaccca tatataagct atatctgctg aatgatcatt  28680
gattactctt atccttagag ataacaactg ggggcacaaa catttattat cattattgaa  28740
cctacaacag agatctatgt gtagatttac aaagcctaca gttctataca gataggaatg  28800
aactattggc ttactgaatg gtgattactt tctgtggggc tcggaactac atgccctagg  28860
atataaaaat gatgttatca ttatagagtg ctcacagaag gaaatgaagt aatataggtg  28920
tgagatccag accaaaagtc atttaacaag tttattcagt gatgaaaaca tgggacaaat  28980
ggactaatat aaggcagtgt actaagctga gtagagagat aaagtcctgt ccagaagata  29040
catgcttcct ggcctgattg aggagatgga aaatttttgc aaaaaacaag gtgttgtggt  29100
cttccatcca gtttcttaag tgctgatgat aaaagtgaat tagacccacc ttgacctggc  29160
ctacagaagt aaaggagtaa aaataaatgc ctcaggcgtg ctttttgatt catttgataa  29220
acaaagcatc ttttatgtgg aatataccat tctgggtcct gaggataaga gagatgaggg  29280
cattagatca ctgacagctg aagatagaag aacatctttg gtttgattgt ttaaataata  29340
tttcaatgcc tattctctgc aaggtactat gtttcgtaaa ttaaataggt ctggcccaga  29400
```

-continued

```
agacccactc aattgccttt gagattaaaa aaaaaaaaaa aaagaaagaa aaatgcaagt  29460
ttctttcaaa ataaagagac atttttccta gtttcaggaa tcccccaaat cacttcctca  29520
ttggcttagt ttaaagccag gagactgata aaagggctca gggtttgttc tttaattcat  29580
taactaaaca ttctgctttt attacagtta aatggttcaa gatgtaacaa ctagttttaa  29640
aggtatttgc tcattggtct ggcttagaga caggaagaca tatgagcaat aaaaaaaaga  29700
ttcttttgca tttaccaatt tagtaaaaat ttattaaaac tgaataaagt gctgttctta  29760
agtgcttgaa agacgtaaac caaagtgcac tttatctcat ttatcttatg gtggaaacac  29820
aggaacaaat tctctaagag actgtgtttc tttagttgag aagaaacttc attgagtagc  29880
tgtgatatgt tcgatactaa ggaaaaacta aacagatcac ctttgacatg cgttgtagag  29940
tgggaataag agagggcttt ttattttttc gttcatacga gtattgatga agatgatact  30000
aaatgctaaa tgaaatatat ctgctccaaa aggcatttat tctgacttgg agatgcaaca  30060
aaaacacaaa aatggaatga agtgatactc ttcatcaaac agaagtgact gttatctcaa  30120
ccattttgtt aaatcctaaa cagaaaacaa aaaaaatcat gacgaaaaga cacttgctta  30180
ttaattggct tggaaagtag aatataggag aaaggttact gtttattttt tttcatgtat  30240
tcattcattc tacaaatata ttcgggtgcc aataggtact tggtataagg tttttggccc  30300
cagagacatg ggaaaaaaat gcatgccttc ccagagaatg cctaatactt tccttttggc  30360
ttgttttctt gttaggggca tggcttagtc cctaaataac attgtgtggt ttaattccta  30420
ctccgtatct cttctaccac tctggccact acgataagca ggtagctggg ttttgtagtg  30480
agcttgctcc ttaagttaca ggaactctcc ttataataga cacttcattt tcctagtcca  30540
tccctcatga aaaatgactg accactgctg ggcagcagga gggatgatga ccaactaatt  30600
cccaaacccc agtctcattg gtaccagcct tggggaacca cctacacttg agccacaatt  30660
ggttttgaag tgcatttaca aggtttgtct attttcagtt ctttactttt tacatgctga  30720
cacatacata cactgcctaa atagatctct ttcagaaaca atcctcagat aacgcatagc  30780
aaaatggaga tggagacatg atttctcatg caacagcttc tctaattata ccttagaaat  30840
gttctccttt ttatcatcaa atctgctcaa gaagggcttt ttatagtaga ataatatcag  30900
tggatgaaaa cagcttaaca ttttaccatg cttaagtttt aagaataaaa taaaaattgg  30960
aaataattgg ccaaaattga aaggaaaaat ttttttaaaa tttctctaaa tgtaggcctg  31020
gctgggcttt gaccttttcc gtttttaaat cactcacaga gggtgggaca ggaggaagag  31080
tgaaggaaaa ggtcaaacct gttttaaggg caacctgcct ttgttctgaa ttggtcttaa  31140
gaacattacc agctccaggt ttaaattgtt cagtttcatg cagttccaat agctgatcat  31200
tgttgagatg aggacaaaat cctttgtcct cactagtttg ctttacattt ttgaaaagta  31260
ttatttttgt ccaagtgctt atcaactaaa ccttgtgtta ggtaagaatg gaatttatta  31320
agtgaatcag tgtgaccctt cttgtcataa gattatctta aagctgaagc caaaatatgc  31380
ttcaaaagaa gaggacttta ttgttcattg tagttcatac attcaaagca tctgaactgt  31440
agtttctata gcaagccaat tacatccata agtggagaag gaaatagata aatgtcaaag  31500
tatgattggt ggagggagca aggttgaaga taatctgggg ttgaaatttt ctagttttca  31560
ttctgtacat ttttagttag acatcagatt tgaaatatta atgtttacct ttcaatgtgt  31620
ggtatcagct ggactcagta acaccccttt cttcagctgg ggatggggaa tggattattg  31680
gaaaatggaa agaagaaagt aactaaaagc cttcctttca cagtttctgg catcactacc  31740
actactgatt aaacaagaat aagagaacat tttatcatca tctgctttat tcacataaat  31800
```

-continued

```
gaagttgtga tgaataaatc tgcttttatg cagacacaag gaattaagtg gcttcgtcat  31860

tgtccttcta cctcaaagat aatttattcc aaaagctaag ataaatggaa gactcttgaa  31920

cttgtgaact gatgtgaaat gcagaatctc ttttgagtct ttgctgtttg gaagattgaa  31980

aaatattgtt cagcatgggt gaccaccaga aagtaatctt aagccatcta gatgtcacaa  32040

ttgaaacaaa ctggggagtt ggttgctatt gtaaaataaa atatactgtt ttga        32094
```

NUCLEIC ACID SILENCING SEQUENCES

CROSS-REFERENCE TO RELATED APPLICATIONS

This application claims the benefit of the filing date of U.S. Application Ser. No. 61/084,918, which was filed on Jul. 30, 2008 and which is hereby incorporated by reference in its entirety.

STATEMENT REGARDING FEDERALLY SPONSORED RESEARCH OR DEVELOPMENT

This invention was made with government support awarded by the National Institutes of Health under Grant Nos. R01GM53234 and T32HD07439. The government has certain rights in this invention.

TECHNICAL FIELD

This invention relates to compositions and methods for silencing gene expression from a whole chromosome or chromosome segment, and more particularly to the use of an Xist gene or other chromosomal silencing RNA to silence expression from trisomic, translocated, duplicated, or partially duplicated genomic sequences.

BACKGROUND

Naturally occurring chromosomal imbalances are an exceptionally important clinical problem, in part because they are extremely common. Almost 1% of all live births and a much higher percentage of conceptions are affected. Many of the abnormalities involve "extra" chromosomal material, and many of these are so deleterious that they cause spontaneous abortion. Trisomies, in which the fetus carries three of a given chromosome rather than a pair, are usually lethal. Some are not; trisomy 13 (Patau syndrome), trisomy 18 (Edward syndrome), trisomy 21 (Down syndrome), triple-X syndrome, as well as duplications of the X and Y chromosomes (e.g., XXY and XYY) are seen in live births, although babies born with Patau syndrome or Edward syndrome usually do not live more than a year or two.

Down syndrome is extremely common relative to other severe genetic disorders. In the United States alone, over 350,000 people are living with the severe handicaps typical of Down syndrome, and there are millions of affected people around the world. Although Down syndrome children are often happy and highly loved, their disorder greatly impacts them, their entire families, and society. Mental retardation, with poor verbal functioning, is the most debilitating outcome, but there are also other medical issues, including much greater risks of early onset Alzheimer's disease, leukemia, and cardiac defects. Because Down syndrome individuals often are at or just below the threshold of independent functioning, even small increases in function could have significant positive consequences for them and their families.

Although the incidence of Down syndrome increases with the mother's age, 80% of Down syndrome babies are born to women under 35 who are not currently subject to prenatal screening. Upon birth of the Down syndrome baby, the whole family is faced with the enormous challenges associated with caring for and nurturing such a child. For older mothers who do have pre-natal screening, the parents are faced with the heart-wrenching decision of birthing a mentally retarded child or terminating the pregnancy, with no hope of systemic therapy. We believe that whole chromosome therapy would result in a paradigm shift in the minds of many scientists, families, and clinicians, who currently presume that gene therapy for this multi-gene disorder, with such pleiotropic effects, is just not possible.

SUMMARY

The present invention features compositions and methods for introducing, into cells, nucleic acids whose expression results in chromosomal silencing. The nucleic acids are targeted to specific chromosomal regions where they subsequently reduce the expression of deleterious genes, or cause the death of deleterious cells. Where the nucleic acid sequence is a silencing sequence, it may encode an Xist RNA or other non-coding, silencing RNA. Accordingly, the present invention features nucleic acid constructs that include a transgene (e.g., a silencing sequence encoding an Xist RNA or other non-coding RNA that silences a segment of a chromosome); first and second sequences that direct insertion of the silencing sequence into a targeted chromosome; and, optionally, a selectable marker. Below, we may refer to the first and second sequences that direct insertion of the silencing sequence into a targeted chromosome as "first and second targeting elements." These sequences or elements can be readily selected and inserted into the nucleic acid constructs using methods well known in the art.

In the present application, we use the term "Xist" to refer to an Xist gene or the encoded Xist RNA regardless of the origin of the sequence. For example, the present compositions can include, and the present methods can be carried out with, an Xist gene encoding an Xist RNA from humans or another mammal (e.g., a rodent such as a mouse, dog, cat, cow, horse, sheep, goat, or another mammalian or non-mammalian animal). We mention this as the scientific literature has adopted a loose convention whereby the term is fully capitalized (XIST) when referring to a human sequence but not fully capitalized (Xist) when referring to the murine sequence. That convention is not used here, and we wish to make clear that human and non-human sequences may be used as described herein.

The "silencing sequence" is a nucleotide sequence that encodes an RNA that silences a chromosome or a segment or region thereof. While the invention is not limited to the use of silencing sequences that work by any particular molecular mechanism, silencing sequences are believed to encode RNA that binds across the chromosome or chromosome segment and induces repressive changes to chromatin that silence gene expression at the level of transcription. The silencing sequence can include, but is not limited to, a naturally occurring DNA sequence, and "silencing" is a term of art that is understood to refer to a significant reduction in the level of transcription of a gene within the silenced or targeted region of a chromosome.

The silencing sequence can be a full-length Xist gene sequence, a sequence encoding another full-length silencing RNA (examples of which are provided below), or any biologically active fragment or other biologically active variant thereof. The sequence is "biologically active" where its activity is sufficient to effect a therapeutically beneficial outcome. The level of activity of a biologically active fragment or other variant may vary so long as a useful chromosomal silencing RNA is produced. Xist RNA is referred to as a chromosomal silencing RNA because it silences by binding across the chromosome or chromosome segment, and therefore silences at the level of transcription, by inducing repressive changes to chromatin. While Xist RNA is a well studied example of a chromosomal silencing RNA, other non-coding RNAs can silence specific clusters of imprinted genes or segments of a chromosome. These other chromosomal silencing RNAs include Air RNA, HOTAIR RNA, and Kcnq1ot1 RNA (see Goodrich and Kugel, *Crit. Rev. Biochem. and Mol. Biol.* 44:3-15, 2009), any of which can be formulated and used as described herein for Xist. Other intergenic noncoding RNAs, which may be useful in the present nucleic acid constructs and the silencing methods described herein are described by Khalil et al. (*Proc. Natl. Acad. Sci. USA* 106:11675-11680, 2009).

The silencing sequence can exclude one or more introns (wholly or partially) or one or more exons (wholly or partially). However, the silencing sequence cannot exclude all exons. For example, the silencing sequence can be an Xist gene sequence exclusive of one or more introns or one or more exons (but not all exons). For example, the silencing sequence can include about 6 kb to about 10 kb of exon 1 of an Xist gene sequence (e.g., about 6-7 kb, 7-8 kb, 8-9 kb, 6.5-8.5 kb, or about 7.5 kb). More specifically, the silencing sequence can be or can include the Xist cDNA sequence having accession number M97168 or a biologically active fragment or other variant thereof (SEQ ID NO:1).

The silencing sequence can be a mammalian sequence (e.g., a human sequence) and can further include a regulatory sequence (e.g., a regulatory sequence that promotes expression of the Xist RNA). More specifically, the regulatory sequence can include a promoter, which may be constitutively active, inducible, tissue-specific, or a developmental stage-specific promoter. Enhancers and polyadenylation sequences can also be included.

The targeted chromosome can be any autosome or an X or Y chromosome. For example, the targeted chromosome can be chromosome 13, chromosome 18, or chromosome 21. The targeted chromosome can be the third chromosome within a trisomic cell or any region of a chromosome that is aberrant (e.g., a gene or genetic sequence that is duplicated, partially duplicated and/or translocated).

Numerous selectable markers can be incorporated in the nucleic acid constructs. These markers are discussed further below and many such markers will be known to one of ordinary skill in the art. Sequences including a selectable marker can, for example, upon transcription and translation, confer resistance to a toxin or encode proteins that produce an observable characteristic. Thus, expression of the selectable marker sequence allows one to distinguish or "select" genetically modified cells from non-modified cells.

Numerous vectors are also known in the art, and any vector (including viral and non-viral vectors) can be used to deliver the present nucleic acids to a patient or a cell in culture. Accordingly, the invention features vectors and isolated or cultured cells that include any of the nucleic acid constructs described herein.

In another embodiment, the invention features compositions (e.g., pharmaceutically acceptable compositions) that include the nucleic acid constructs or vectors described above (and elsewhere herein) and, alternatively or in addition, a vector that facilitates delivery of the transgene to a cell and/or incorporation of the transgene into the targeted chromosome. Thus, the invention encompasses pharmaceutically acceptable compositions that include nucleic acid constructs carrying a transgene (e.g., a silencing sequence), first and second sequences that direct insertion of the silencing sequence into a targeted chromosome and, optionally, a selectable marker. The targeted integration may be facilitated by inclusion in the construct of sequences homologous to the site of desired chromosomal integration (i.e., the first and second sequences or targeting elements), coupled with the transgene (e.g., sequence encoding Xist RNA or other chromatin-associated silencing RNA).

As noted, the invention features compositions that also include vectors that facilitate delivery of the transgene. Well established targeting methods that rely on homologous recombination can be made more efficient by use of zinc finger nucleases to direct integration at specific sites. Thus, the present compositions can include a cleavage vector comprising a sequence encoding a first chimeric zinc finger nuclease (ZFN) or an adeno associated virus, which can specifically integrate the transgene and deliver it to cells. We describe the ZFNs as "chimeric" as they include at least one zinc finger DNA binding domain effectively linked to at least one nuclease capable of cleaving DNA. Ordinarily, cleavage by a ZFN at a target locus results in a double stranded break (DSB) at that locus.

Various combinations of the constructs and vectors described herein can also be formulated as pharmaceutical compositions. For example, the present compositions can include an adeno associated virus into which a silencing sequence has been inserted or a combination of (a) a nucleic acid construct or vector that silences a targeted chromosomal region or induces cell death following targeted chromosomal integration and (b) a cleavage vector encoding a chimeric ZFN.

The cleavage vector can include more than one chimeric ZFN, any of which can include a DNA binding domain and a cleavage domain. The DNA binding domain binds a genomic sequence that is present in each of the two strands of the targeted chromosome such that the cleavage domain generates a double stranded break in the targeted chromosome at a site into which the first and second sequences will direct insertion of the silencing sequence.

The same cleavage vector that encodes a first chimeric ZFN can include one or more additional sequences encoding one or more additional chimeric ZFNs (e.g., two, three, four, or more ZFNs). Alternatively, additional chimeric ZFNs can be carried on a separate vector. The second and any subsequent chimeric ZFNs can include a DNA binding domain and a cleavage domain. The first chimeric ZFN and the second chimeric ZFN bind, respectively, to distinct sequences in each of the two strands of the targeted chromosome such that the respective cleavage domains generate a double stranded break in the targeted chromosome at a site into which the first and second sequences within the nucleic acid construct will direct insertion of the silencing sequence (or other sequence (e.g., a sequence that causes cell death)). As when the nucleic acid constructs or vectors, including adeno associated vectors, are used alone, the ZFNs can target an autosome. For example, ZFNs can target chromosome 13, chromosome 18, or chromosome 21.

Also within the scope of the invention are RNAs and proteins encoded by the cleavage vector and compositions that include them (e.g., lyophilized preparations or solutions, including pharmaceutically acceptable solutions or other pharmaceutical formulations).

In another embodiment, the invention features cells that include the nucleic acid constructs, vectors (e.g., an adeno associated vector), and compositions described herein. The cell can be isolated in the sense that it can be a cell within an environment other than that in which it normally resides (e.g., the cell can be one that is removed from the organism in which it originated). The cell can be a germ cell, a stem cell (e.g., an embryonic stem cell, an adult stem cell, or an induced pluripotent stem cell (iPS cell or IPSC)), or a precursor cell. Where adult stem cells are used, the cell can be a hematopoietic stem cell, a cardiac muscle stem cell, a mesenchymal stem cell, or a neural stem cell. The cell can also be a differentiated cell (e.g., a fibroblast or neuron).

The methods of the invention can be used to treat patients who have a birth defect, genetic disease, or cancer associated with a genetic aberration (e.g., a trisomy, partial duplication of a chromosomal region, translocation, or ring X-chromosome). Any of the methods can include the step of identifying a patient in need of treatment; any of the patients can be human; and any of the methods can be carried out by either administering the present compositions to the patient or removing cells from the patient, treating the cells, and "readministering" those cells. For example, the invention features methods of treating a genetic disorder associated with a trisomic chromosome by identifying a patient in need of treatment; and administering to the patient a nucleic acid construct, vector, and/or cleavage vector as described herein. The targeted chromosome can be the trisomic chromosome, and the amount of the construct or vector administered will be an amount sufficient to improve a condition associated with the disorder. Where cells are harvested from a patient to treat a condition or disorder described herein (or an associated symptom), the methods can include the steps of identifying a patient in need of treatment; harvesting cells from the patient; transfecting the cells with one or more of the types of constructs and/or vectors described herein; and administering to the patient a sufficient number of the transfected cells to treat the condition or improve a condition or symptom associated with the disorder. The symptoms associated with many birth defects and other conditions are well known. For example, individuals having Down Syndrome often experience mental retardation, hypotonia, cardiac defects, Alzheimer's Disease, hematological abnormalities and leukemia (see Antonarakis and Epstein, *Trends Mol. Med.* 12:473-479, 2006). As noted above, treatment can also be carried out in vivo by administering present compositions to the patient via pharmaceutically acceptable compositions.

The cells can include differentiated cells (e.g., white blood cells or fibroblasts) and/or undifferentiated cells (e.g., stem cells or precursor cells). The cells can also be differentiated cells that are induced, ex vivo, into iPS cells, or multi-potent stem cells or stem cells of particular lineage, such as neural stem cells. The condition can be a neurological or blood disorder such as Alzheimer's Disease and leukemia, respectively, or a muscular defect, including defects of the heart. Where the condition is myelodysplastic disease which leads to leukemia, it can be an acute lymphocytic leukemia, an acute myelogenous leukemia, or an acute megakaryoblastic leukemia.

In any of the present methods, cells can be transfected with a cleavage vector that includes a sequence encoding a first chimeric zinc finger nuclease (ZFN) having a DNA binding domain and a cleavage domain. As in other embodiments, the DNA binding domain binds a genomic sequence that is present in each of the two strands of the targeted chromosome such that the cleavage domain generates a double stranded break in the targeted chromosome at a site into which the first and second sequences will direct insertion of the silencing sequence or other therapeutically useful sequence (e.g., a toxin or pro-apoptotic protein). Where desirable, the transgene (e.g., a silencing sequence encoding an Xist RNA) can be targeted to a polymorphic sequence that is present in just one chromosome (e.g., one of a set of trisomic chromosomes). Additionally, integration of the Xist transgene can be targeted so as to directly disrupt a particularly deleterious gene, such as the APP gene, over-expression of which leads to the exceptionally high rate and early onset of Alzheimer's Disease among Down Syndrome individuals.

The invention also includes compositions and methods for the silencing of a duplicated genomic region or trisomic chromosome using an approach of random transgene integration followed by cell selection, where the silencing of the trisomic chromosomal material provides a significant selective advantage as compared to silencing of other disomic chromosomes. As a result, patient cells in which the deleterious extra chromosomal material has been silenced by a large non-coding RNA may have a selective advantage; thus, even where Xist transgenes have been inserted at random into the genome of patient cells, cells in which the trisomic chromosome has been silenced may be selected for over those cells in which a disomic chromosome has been silenced (since the latter would generate a functional monosomy that is likely lethal to the cell). In the case of translocated chromosomes, targeting of the transgene can be directed to the unique site generated at the translocation junction, to selectively silence that abnormal chromosome, or to introduce a sequence encoding a toxin, pro-apoptotic protein, or other factor that results in cell death of deleterious cells. For example, using the present methods, one can introduce a sequence encoding a toxin, pro-apoptotic protein, or other factor that results in cell death into a translocated chromosome associated with cancer. This approach can be extended to silencing of duplicated regions of specific chromosomes that are associated with genetic conditions, such as duplication of segments of Chromosome 15q11-13 in Autism. This duplication, which is thought to be the most frequent cytogenetic abnormality in autism, can be targeted by the present methods and is described further in Nakatani et al. (*Cell* 137:1236-1246, 2009). This approach can also be extended to silencing the inappropriate expression of imprinted regions in genetic disease, as in Prader-Willi/Angelman syndrome, also on Chr 15 and associated with autism.

To illustrate a particular application, Xist mediated chromosomal therapy could be used to ameliorate transient myeloproliferative disorder (TMD) in Down Syndrome children and possibly prevent the later development of acute leukemia. Successful bone marrow transplants for diseases like leukemia depend upon immune compatibility, to avoid Graft versus Host Disease (GVHD). To avoid graft rejection, the patient's own cells can be used and transgenically modified prior to transplant. There are two scenarios to acquire and modify stem cells for bone marrow transplant. In the first, the patient's own bone marrow stem cells can be obtained and an Xist transgene can be introduced and targeted to chromosome 21. When Xist expression silences the trisomic chromosome, these cells can then be transplanted back into the patient following standard bone transplant procedures following the destruction of the patient's bone marrow using irritation. Alternatively modified patient bone marrow cells can be transplanted without first irradiating the patient to destroy the unmodified bone marrow. This would produce a situation where the patient's bone marrow would be mosaic for trisomy 21 (a mixture of modified and unmodified cells). We expect that the modified cells would have a growth advantage over the non-modified fully trisomic cells, and the modified cells would eventually out grow the "diseased" cells (see Douillard-Guilloux et al., *J. Gene Med.* 11:279-287, 2009). In the second approach, the patient's fibroblast (skin) cells can be used to produce iPS cells, into which a transgenic Xist gene is inserted and targeted to chromosome 21. IPS cells that silence one of the three trisomic chromosomes will then be differentiated into adult hemopoietic stem cells and introduced back into the patient as stated above.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 6A-E are a series of five contiguous panels showing the complete exon sequence of the *Homo sapiens* X (inactive)-specific transcript (Xist), GenBank Accenssion No. M97168.1, SEQ ID NO:1.

FIGS. 7A-J are a series of 10 contiguous panels showing the *Homo sapiens* DNA sequence from clone RP13-216E22 on chromosome Xq13.1-21.1 with the X (inactive)-specific transcript (non-protein coding) (Xist), non-coding RNA, GenBank Accession No. AL353804.22, SEQ ID NO:2.

DETAILED DESCRIPTION

Down Syndrome, caused by trisomy of chromosome 21, is the leading cause of mental retardation in newborns, impacting one in every 600-700 live births in the U.S. and across the world. Many families with Down Syndrome children find them loving, happy children, but they are challenged with mild to moderate mental retardation and frequently have a number of medical conditions requiring treatment or surgery. Despite the enormous clinical importance of Down Syndrome and related chromosomal imbalances, there has been little hope or effort for gene therapy in Down Syndrome. Historically, devising therapeutic strategies for trisomies has been particularly challenging because more is involved than a single defective gene or even several defective genes. Down syndrome, for example, involves a quantitative imbalance in tens or hundreds of genes across a 50 Mb chromosome, the most important of which are still not yet well understood (Antonarakis and Epstein, *Trends Mol. Med.* 12:473-479, 2006). Thus, unlike other genetic diseases in which silencing of an individual gene might produce an effective therapy, genetic therapy for trisomies such as Down syndrome is much more challenging. This is because chromosomal trisomies (and segmental duplications or translocations) involve the over-expression of potentially hundreds of genes across a ~50 Mb or larger chromosome, rendering ineffective standard approaches to gene therapy which treat single gene defects.

This invention makes possible an approach to "chromosome therapy" for trisomies or segmental duplications by reducing the challenge of individually correcting over-expression of tens or hundreds of genes, to the much more tractable approach of introducing just one gene, for example Xist, which then silences the whole chromosome.

Figure 1:
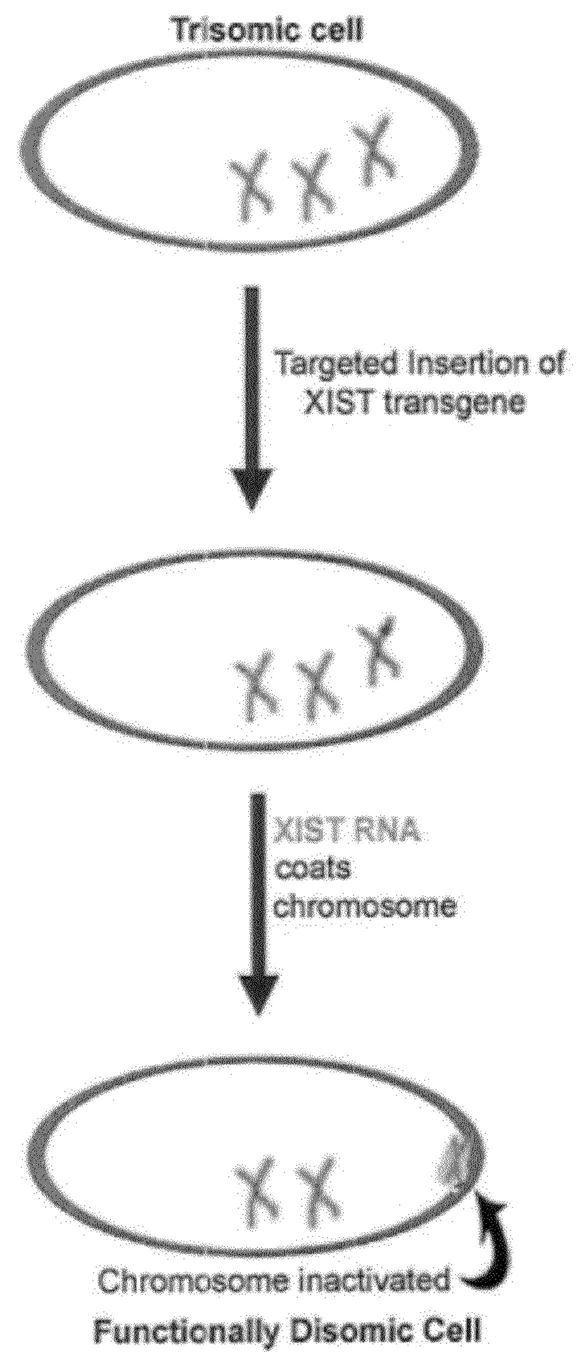
FIG. 1 is a schematic diagram illustrating the process of chromosomal inactivation. Three chromosomes are shown in the cell initially. Following targeted insertion of an Xist transgene, Xist RNA exerts its effect on chromosomal sequences that are cis to the Xist transgene, resulting in inactivation of one chromosome and a functionally disomic cell.
Figure 2:
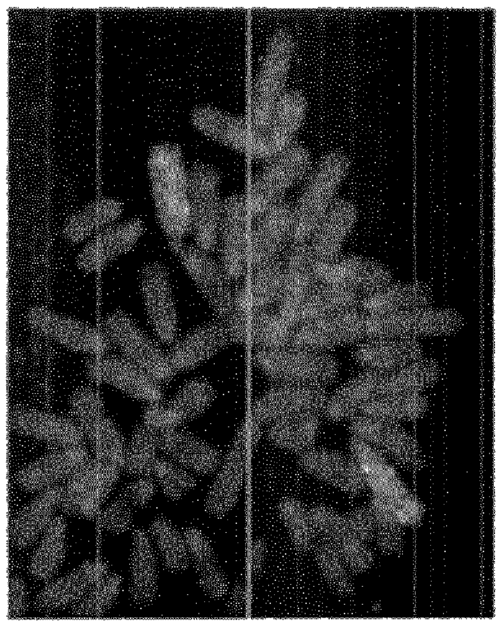
FIG. 2 is an image of chromosomes from an XXX mouse cell showing that Xist RNA (green in color and brighter in black-and-white) coats two X-chromosomes and inactivates both.

We set out to develop an innovative approach to chromosome therapy that would translate the system nature devised to dosage compensate the X chromosome in females. Nature assures proper "gene dosage" of X-linked genes between females (XX) and males (XY) via the Xist gene, which produces a large, non-coding RNA (Brown et al., *Cell,* 71:527-542, 1992; Clemson et al., *J. Cell Biol.* 132:259-275, 1996) that is expressed from and accumulates exclusively on the inactive X chromosome (Xi), "painting" the whole structure of the interphase chromosome territory (reviewed in Hall and Lawrence, *Semin. Cell Dev. Biol.* 14:369-378, 2003). Brown et al. discloses the cDNA sequence of Xist, which can be used in the design and construction of the nucleic acid constructs described herein. FIG. 2 shows mouse Xist RNA on two mitotic X chromosomes in a cell with X trisomy. Nature has also devised a counting mechanism such that all but one X chromosome is silenced (thus trisomy X has essentially normal gene dosage and is viable). Once Xist RNA coats the chromosome, a series of chromatin modifications occurs which are key hallmarks of the inactive X, including histone H3K27 methylation, H2A ubiquitination, macroH2A, and hypoacetylation of histone H4 (e.g. FIG. 5). Importantly, although Xist RNA is essential to initially enact this silencing process, once formed, the heterochromatic chromosome remains largely inactivated, even if Xist expression is later experimentally silenced (reviewed in Hall and Lawrence, *Semin. Cell Dev. Biol.* 14:369-378, 2003).

The new system would result in the silencing of additional or duplicated material (e.g., trisomies or segmental duplications) or translocated genomic material (e.g., the translocation of chromosomal arms that sometimes gives rise to birth defects or the translocations seen in certain cancers). The silencing would not be targeted to an intact X chromosome but could be targeted to an abnormal X chromosome lacking the Xist gene.

Where the intention is to "turn off" an extra chromosome, one can incorporate a silencing sequence using the compositions and methods described herein. The silencing sequence (e.g., an Xist gene of a human or other mammal such as a mouse or another silencing sequence described herein) is targeted to the region to be silenced (e.g., to the trisomic chromosome).

In another embodiment, where the intention is to kill a genetically aberrant cell (e.g., a cell in which a cancer-related translocation has occurred), one can incorporate a silencing sequence at the unique site of the translocation using the compositions and methods described herein. Silencing of the translocation would create a functional monosomy for the involved autosomal material which, depending on the chromosomal region silenced and the extent of the chromosomal region silenced would induce cell death or impede cell proliferation. In addition to incorporating a silencing sequence or as an alternative to incorporating a silencing sequence, one can use the present nucleic acid constructs and methods to target a "cell death" gene to the site of the translocation. For example, the nucleic acid construct can include an Xist gene and/or a gene encoding a toxin or pro-apoptotic factor. The toxins that can be expressed may include Shiga toxins 1 and 2 (Stx1 and Stx2); botulinum toxin from *Clostridium botulinum*; a virulence factor produced by *Bacillus anthracis* (e.g., a tripartite exotoxin referred to as anthrax toxin); a *Vibrio cholerae* multifunctional-autoprocessing RTX toxin; pertussis toxin from *Bordetella pertussis*; VacA from *Helicobacter pylori*: diphtheria exotoxin from *Corynebacterium diphtheriae*; ricinus communis; pasteurella multocida toxin (PMT); β-toxin-like peptide (named BmKBT) and two MkTx I homologues (named MkTx II and MkTx III), from a venom gland cDNA library of the Chinese scorpion *Buthus martensii* Karsch; haemorrhagic toxin acutolysin A from *Agkistrodon acutus: Bacillus thuringiensis* (Bt) toxin Cry1A and Cry1A (b); and Type A *Clostridium perfringens* cpb2. The pro-apoptotic proteins that can be expressed include, for example, Bcl-2-associated X protein (BAX), BH3 interacting domain death agonist (BID), Bcl-2 homologous antagonist killer (BAK), and Bcl-2-associated death promoter (BAD).

As noted, the translocation or duplication may be associated with a birth defect or may be a translocation associated with a cancer. The targeted chromosomal regions are then regions at or near the site of the translocation or duplication. These sites can be determined through genetic and sequence analysis, and several examples are known in the art. For example, one can target the following known sites of translocations: t(2;5)(p23;q35), which is associated with anaplastic large cell lymphoma; t(8;14), which is associated with Burkitt's lymphoma (c-myc); t(9;22)(q34;q11)/Philadelphia chromosome, which is associated with CML and ALL; t(11;14), which is associated with Mantle cell lymphoma (Bcl-1); t(11;22)(q24;q11.2-12), which is associated with Ewing's sarcoma; t(14;18)(q32;q21), which is associated with follicular lymphoma (Bcl-2); t(17;22), which is associated with dermatofibrosarcoma protuberans; t(15;17), which is associated with acute promyelocytic leukemia; t(1;12)(q21;p13), which is associated with acute myelogenous leukemia; t(9;12)(p24;p13), which is associated with CML and ALL (TEL-JAK2); t(X;18)(p11.2;q11.2), which is associated with synovial sarcomas; t(12;15)(p13;q25)-(TEL-TrkC), which is associated with acute myeloid leukemia, congenital fibrosarcoma, and secretory breast carcinoma.

Where the transgene is delivered to the patient, it will be useful to use a delivery system such as adeno associated virus, which also has the potential for site-specific integration.

Thus, the strategies described herein are applicable to trisomies, translocations, or any partial duplication of genomic DNA or aberration. For example, the present compositions and methods can be used to silence fragment or ring X-chromosomes associated with severe mental retardation.

Our strategies are based on our belief that trisomies can be treated by silencing essentially the whole trisomic chromosome, which would obviate the need to decipher the complex pathologies of the resulting syndromes and determining which specific genes are most "important" (if that is even possible at any practical level) (Antonarakis et al., *Trends Mol. Med.* 12:473-479, 2006). The silencing can be carried out in a variety of cell types which naturally represent or are induced to represent a variety of developmental stages (e.g., in early embryonic stem cells or induced pluripotent stem cells, fetal cells, neonatal cells, and other types of stem cells including hematopoietic cells, neural stem cells, mesenchymal stem cells, and other types of stem cells). In preparation for human therapies, the silencing can be carried out in a mouse model of Down syndrome. Several such models are available and known in the art. One could use any of the nucleic acid constructs described herein to determine if either the abnormal phenotype (or any aspect thereof) or embryonic lethality of a Down Syndrome mouse model could be rescued or ameliorated.

Figure 3:
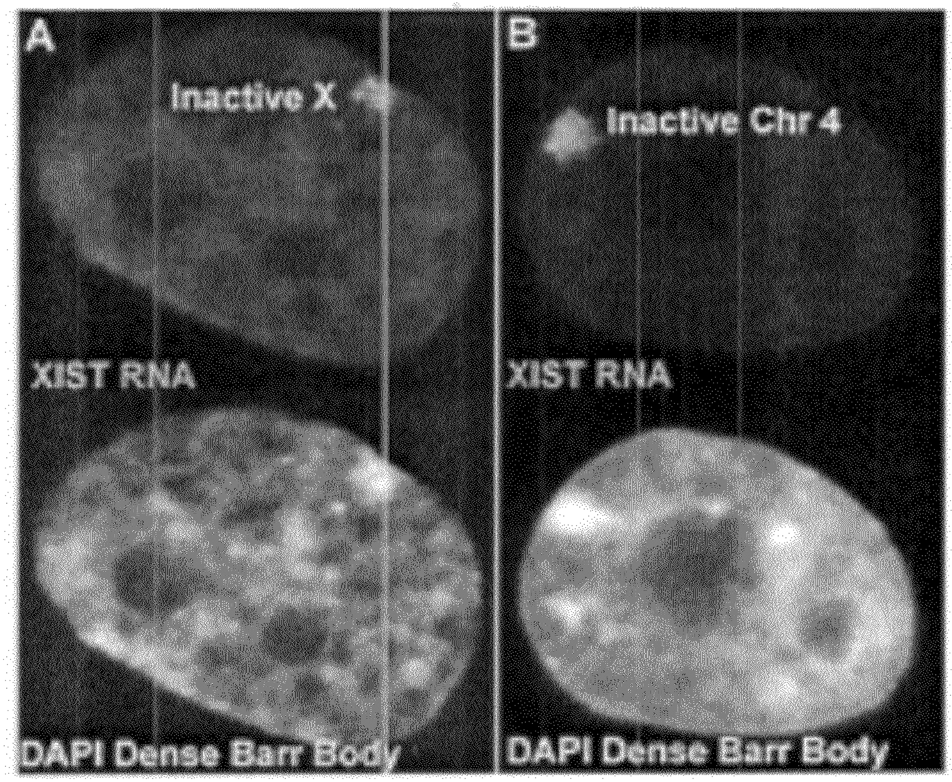
FIG. 3A is a photograph showing Xist RNA localized to an inactive X chromosome in a cell (upper photograph) and the corresponding DAPI dense Barr Body in the same cell (lower photograph).
FIG. 3B is a photograph showing Xist RNA localized to an inactive human Chr 4 carrying a transgenic Xist gene (upper photograph) and the lower panel shows the corresponding DAPI dense Barr Body in the same cell (lower photograph). Inactivation of the autosome occurred in an adult somatic cell (derived from a fibrosarcoma).
Figure 4:
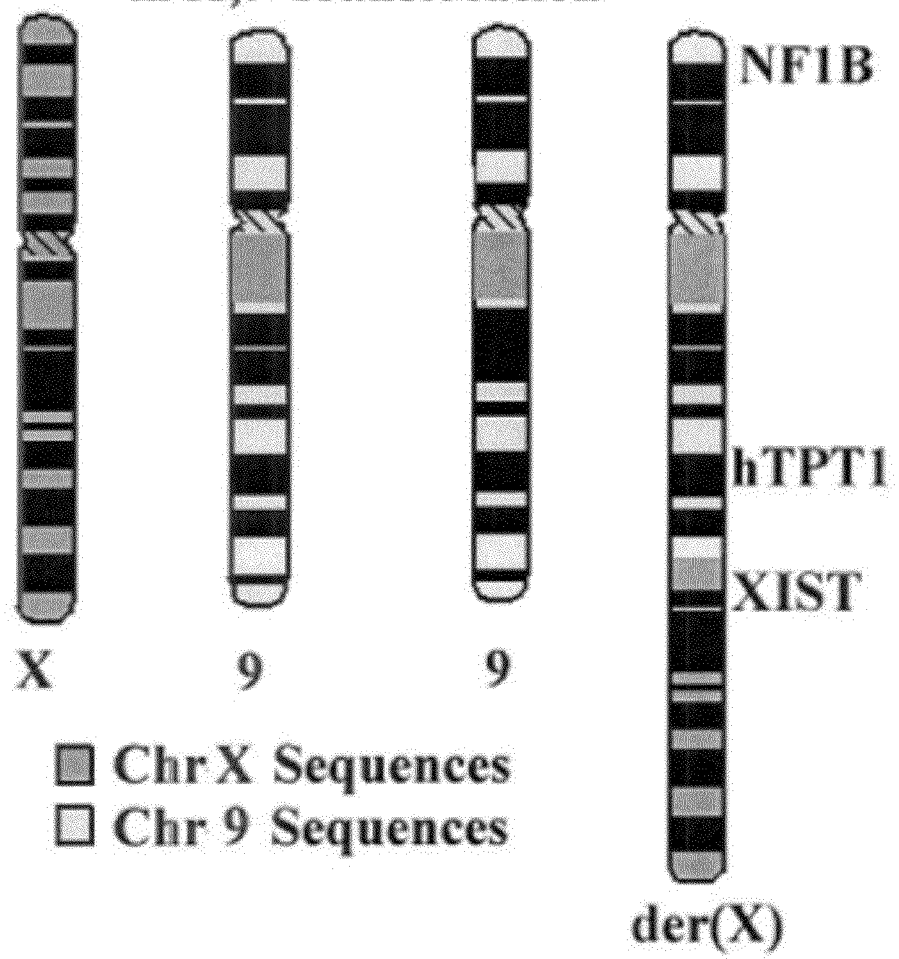
FIG. 4 is a schematic diagram of a karyotype of chromosomes involved in X;9 translocation, in which Xist RNA was shown to silence the duplicated Chromosome 9 material in the transgene, thereby avoiding the deleterious effects of partial Chr. 9 trisomy.

Although the potential therapeutic use of Xist transgenes for chromosomal trisomies has not been envisioned in the art, we believe that the mechanism whereby nature silences one X-chromosome in females can be extended to autosomal material, based on analysis of patients that carry naturally occurring X:autosome translocations. Two patients carrying X-autosome translocations in the context of trisomy for that autosome avoided otherwise devastating clinical consequences due to silencing of autosomal regions by endogenous Xic regions (Hall et al., *Proc. Natl. Acad. Sci. USA,* 99:8677-8682, 2002) (FIG. 4). In addition, we have shown that it is possible for an Xist transgene randomly integrated into a human autosome to induce silencing in somatic cells, when it had previously been believed that it could do so only in mouse embryonic stem cells (Hall et al., *Hum. Mol. Genet.,* 11:3157-3165, 2002) (e.g. see "Chr. 4 Barr Body in FIG. 3). We have cultured and used the transgenic cells described herein, and we have observed highly stable Xist expression and autosome silencing. We have also found evidence that two cultured (neoplastic) cell lines support chromosome silencing to a large degree at most of the random integration sites tested (Chow et al., *Proc. Natl. Acad. Sci. USA* 104:10104-10109, 2007). A caveat to these studies is that they were done in transformed cell lines, leaving open the possibility that the neoplastic changes somehow allow formation of Xi heterochromatin. However, several recent studies from our lab and others demonstrate that cancer cells most commonly lose heterochromatin, including the inactive X (Pageau et al., 2007), thus we believe this is unlikely to be the explanation. No prior studies have described the use of a transgenic construct that is integrated into an autosome in a site-specific manner. The present nucleic acid constructs include targeting elements (e.g., first and second targeting elements) that drive integration of a silencing sequence (e.g., an Xist transgene) into a selected or targeted region of the genome (e.g., into a trisomic chromosome). The first and second sequences and/or the first and second targeting elements are nucleic acid sequences that share sequence homology (including sequence identity) with a chromosomal site and, due to base pairing between the first and second sequences (and/or the first and second targeting elements) and sequences present at the chromosomal site, promote site-specific integration of all or part of a nucleic acid construct of which they are a part into the chromosomal site.

Integrated Mouse Xist or human Xist transgenes can silence an autosome, as shown by studies in mouse embryonic stem cells (Wutz and Jaenisch, *Mol. Cell,* 5:695-705, 2000; Savarese et al., *Mol. Cell. Biol.* 26:7167-7177, 2006) and in human somatic (fibrosarcoma) cells (FIG. 3; Hall et al., *Hum. Mol. Genet.* 11:3157-3165, 2002; Chow et al., *Proc. Natl. Acad. Sci. USA* 104:10104-10109, 2007). Natural autosomal silencing by Xist was also shown in patient cells, with an autosomal trisomy due to X;autosome translocations (Hall et al., *Proc. Natl. Acad. Sci. USA* 99:8677-8682, 2002; (FIG. 4)). Although the silencing of autosomal material may not be quite as complete or may vary somewhat between autosomal regions, autosomes studied to date are largely if not entirely silenced in response to Xist RNA. While Chr. 21 has not been directly tested, its small (~50 Mb) acrocentric (essentially no short arm) structure is favorable, since Xist RNA would not need to spread far or across a centromere.

The fact that, to our knowledge, targeted inactivation of autosomes has never been discussed in the literature, possibly due to the belief that an Xist transgene cannot silence a chromosome outside a very narrow and early embryonic window and/or because the use of Xist transgenes for chromosomal therapeutic purposes was not envisioned. However, our studies of human Xist transgenes in adult cells and in differentiated embryonic cells (induced to express Xist post-differentiation) lead us to believe that the potential for Xist-mediated chromosome therapy in somatic cells is significant.

The present compositions and methods are applicable to abnormalities involving duplication of chromosomal material. Duplication of even a small chromosome fragment has severe clinical consequences. For example, Turner's syndrome (45, X) females have only one X-chromosome but typically have a quite mild phenotype, with normal intelligence but primary amenorrhea and sterility. However, Turner syndrome fetuses often have a fragment of the second X chromosome, which can result in either a very severe phenotype or the Turner-like mild one. A key to whether this fragment will be deleterious is whether or not it contains the Xist gene (Nussbaum et al., *Thompson and Thompson Genetics in Medicine*, Philadelphia, Pa., Saunders/Elsevier, 2007). If the Xist gene is present, the chromosome fragment is silenced and the deleterious effects are avoided. Thus, Xist could be inserted into an abnormal chromosome that lacks Xist sequences. Another category of duplication events arises via imbalanced translocations, and we have previously characterized two examples in which the imbalance was rescued by the Xist gene on the translocated chromosome. FIG. 4 shows the karyotype of an individual with a normal phenotype, even though they carried a Chr. 9 trisomy which would otherwise be lethal. Instead, the extra chr. 9 material was silenced by the Xist gene on the translocated chromosome. We showed that Xist RNA coated much of the Chr. 9 material, as it did Chr. 14 material in an analogous example, and in both cases Xist nullified what would have been a devastating trisomy (reviewed in Hall and Lawrence, *Semin. Cell Dev. Biol.* 14:369-378, 2003). Similarly, Xist transgenes could potentially silence any rearrangement which creates duplication (partial trisomy) for part of a chromosome.

Nucleic acid constructs: Accordingly, the present invention features nucleic acid constructs that include a silencing sequence and one or more targeting sequences (e.g., first and second sequences that flank the silencing sequence and direct insertion of the silencing sequence into a targeted chromosome). The silencing sequence can be or can include the sequence of an XIC (X inactivation complex) locus or any portion thereof that encodes an RNA capable of silencing the chromosome into which it has been inserted. For example, the constructs can include an XIC locus lacking the sequences 3' to Xist that trigger the "counting" mechanism. Other constructs can include the Xist gene, with or without some or all of the intronic sequences, or a biologically active variant of the Xist gene (e.g., a fragment or other mutant). For information regarding the structure of XIC, one can consult Wutz and Gribnau (*Curr. Opin. Genetics Dev.* 17:387-393, 2007).

The silencing sequence (e.g., an Xist transgene) can silence the expression of one or more genes located within a trisomic and/or translocated chromosomal region located in cis to the integrated Xist transgene. In certain embodiments, the targeting elements are sequences homologous to those that occur naturally in the trisomic and/or translocated chromosomal region and will promote integration of the silencing sequence (e.g., an Xist transgene) to the corresponding trisomic and/or translocated chromosomal region. The targeted region may be a polymorphic region (i.e., a region where corresponding sequences differ between paired chromosomes in an individual). Whether the present nucleic acid constructs are used alone or in combination with a second moiety that enhances or facilitates homologous recombination (e.g., a zinc finger nuclease), the targeted region can be one having only one or more polymorphic sites, such as single nucleotide polymorphisms (SNPs). Zinc finger domains can recognize and target highly specific chromosomal sequences, including SNPs, which can be used to facilitate targeted integration of the transgene to particular alleles in just one of the homologouse chromosomes. As noted, a vector that may facilitate both insertion of a transgene and delivery to a cell is an adeno associated virus, but delivery of the transgene to cells in vitro may be done by commonly used transfection methods, without the use of any adeno-associated, lenti or other virus.

In certain other embodiments, the targeting elements are homologous to non-naturally occurring sequences that have been introduced into a trisomic and/or translocated region by recombinant methods. In these embodiments, the targeting elements will promote integration of the transgene at a site defined by the non-naturally occurring sequences, such as FRT sequences, which can promote integration into that site.

Regardless of whether the silencing sequence is inserted with the assistance of a polymorphism on the targeted chromosome or whether the nucleic acid constructs are used in combination with a second moiety that enhances or facilitates homologous recombination, the present compositions and methods can be designed to target just one copy of a chromosome if desired. These methods can also be used to target one or more than one site on a targeted chromosome (e.g., two, three, or four sites), which may or may not be in close proximity to one another. While it is our expectation that the RNA encoded by the silencing sequence or transgene will silence most if not all of the genes residing on the targeted chromosome, one can nevertheless target specific genes (e.g., genes associated with Alzheimer's Disease (e.g., APP), leukemias (e.g., RUNX1) or other conditions that occur with increased frequency in patients with trisomies or translocation).

As would be understood in the art, the term "recombination" is used to indicate the process by which genetic material at a given locus is modified as a consequence of an interaction with other genetic material. Homologous recombination indicates that recombination has occurred as a consequence of interaction between segments of genetic material that are homologous or identical. In contrast, "non-homologous" recombination indicates a recombination occurring as a consequence of the interaction between segments of genetic material that are not homologous (and therefore not identical). Non-homologous end joining (NHEJ) is an example of non-homologous recombination.

As used herein, an Xist transgene refers to a nucleic acid sequence having the sequence of all or part of a naturally occurring Xic region so long as it (a) includes an Xist RNA coding sequence or a biologically active variant thereof and (b) is functional (e.g., the Xist transgene is capable of silencing the expression of one or more genes in cis when integrated into a chromosome). The Xist transgene may carry one or more regulatory elements found in the Xic region that are not a part of the Xist coding sequence. For example, deletion of the DXPas34 locus found 3' to the Xist coding sequence eliminates Xist expression in mammalian embryonic stem cells as described in Debrand et al. (*Mol. Cell. Bio.,* 19:8513-8525, 1999) herein incorporated by reference. As a further example, silencing by mouse Xist transgenes have been shown to require a conserved repeat sequence located at the 5' end of Xist (Wutz et al., *Nat. Genetics,* 30:167-174, 2002).

The Xist transgene need not include the whole of the Xist gene sequence, although it may. For example, the Xist transgene may be derived from an Xist cDNA cloned from one of multiple naturally occurring splice variants. This cDNA may lack sequences corresponding to one or more introns or exons or portions thereof. Additionally, the Xist transgene may include non-naturally occurring Xist coding sequences. For example, the Xist coding sequence may be mutated (e.g., truncated) or otherwise variant with respect to naturally occurring Xist coding sequences so long as it includes sequences that are required for transgene function. For example, deletion analysis demonstrates that the first exon of human Xist is sufficient for both transcript localization and the induction of silencing (Chow et al. *Proc. Natl. Acad. Sci. USA* 104:10104-10109, 2007). Thus, smaller Xist constructs can be generated that are more easily manipulated but still biologically active.

Non-limiting examples of Xist transgenes (derived from mouse and human sequences) that are useful in this invention are described in the following references which are herein incorporated by reference: Chow et al. (*Proc. Natl. Acad. Sci. USA* 104:10104-10109, 2007); Hall et al. (*Proc. Natl. Acad. Sci. USA* 99:8677-8682, 2002); Chow et al. (*Genomics,* 82:309-322, 2003); and Wutz et al. (*Nat. Genet.,* 2002, 30:167-174, 2002).

The nucleic acid constructs of this invention include targeting sequences or elements that promote sequence specific integration of an Xist transgene into a chromosomal site (e.g., by homologous recombination). Methods for achieving site-specific integration by ends-in or ends-out targeting are known in the art and in the nucleic acid constructs of this invention, the targeting elements are selected and oriented with respect to the Xist transgene according to whether ends-in or ends-out targeting is desired. In certain embodiments, two targeting elements flank the Xist transgene.

As described previously, the targeting element may be identical in sequence to a naturally occurring sequence found in a trisomic and/or translocated chromosomal region. For example, a targeting element may be identical in sequence to a sequence found in any one of human chromosomes 9, 13, 14, 18, or 21 (as described in Hattori et al., *Nature,* 405:311-319, 2000) or in any other chromosome. In another example, a targeting element may be identical in sequence to a sequence found in any one of mouse chromosomes 16, 17, or $T(17^{16})$65Dn.

A targeting sequence or element may vary in size. In certain embodiments, a targeting element may be at least or about 100, 200, 300, 400, 500, 600, 700, 800, 900, 1000, 2000, 3000, 4000, 5000, 6000, 7000, 8000, 9000, 10000 bp in length (or any integer value in between). In certain embodiments, a targeting element is homologous to a sequence that occurs naturally in a trisomic and/or translocated chromosomal region, including a polymorphic sequence which may be present on just one of the homologous chromosomes.

Accordingly, in one aspect, the invention provides an isolated or purified nucleic acid construct that includes a silencing sequence (e.g., an Xist transgene) and one or more targeting sequences that are oriented with respect to each other in such a way that the Xist transgene can be integrated in a site-specific fashion into a chromosomal site when the nucleic acid construct is introduced into a cell.

The construct elements as described here may be variants of naturally occurring sequences. Preferably, any construct element (e.g., an Xist transgene, other non-coding, silencing RNA, or a targeting element) includes a nucleotide sequence that is at least 60% identical to its corresponding naturally occurring sequence (its reference sequence, e.g., an Xist coding region, a human Chr 21 sequence, or any duplicated or translocated genomic sequence). More preferably, the silencing sequence or the sequence of atargeting element is at least 65%, 70%, 75%, 80%, 85%, 90%, 91%, 92%, 93%, 94%, 95%, 96%, 97%, 98%, 99% identical to its reference sequence (e.g., SEQ ID NO:1 or SEQ ID NO:2).

As used herein, "% identity" of two nucleic acid sequences is determined using the algorithm of Karlin and Altschul (*Proc. Natl. Acad. Sci. USA,* 87:2264-2268, 1990), modified as in Karlin and Altschul, *Proc. Natl. Acad. Sci. USA,* 90:5873-5877, 1993). Such an algorithm is incorporated into the NBLAST and XBLAST programs of Altschul et al. (*J. Mol. Biol.* 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et at (*Nucl. Acids Res.,* 25:3389-3402, 1997). When utilizing BLAST and Gapped-BLAST programs the default parameters of the respective programs (e.g., XBLAST and NBLAST) are used to obtain nucleotide sequences homologous to a nucleic acid molecule of the invention.

The nucleic acid constructs of the invention can be prepared by recombinant methods that are known in the art.

Moreover, the present invention provides a vector containing one or more of the nucleic acid constructs described herein. The vector may be useful for propagating the nucleic acid construct or may contain elements useful for integrating the Xist transgene into a chromosome once the vector has been introduced into a mammalian cell. For example, the vector may be an expression vector designed to express a recombinase, such as Fok1 recombinase, coupled with a zinc finger nuclease, designed to aid in the integration of the silencing sequence (e.g., an Xist transgene) into a chromosome at a specific site.

For expression in animal cells, such as embryonic stem cells, adult bone marrow stem cells, CHO, COS, and NIH3T3 cells, the expression vector must have a promoter such as an SV40 promoter (Mulligan et al., *Nature* 277:108, 1979), MMLV-LTR promoter, EF1α promoter (Mizushima et al., *Nucl. Acids Res.* 18:5322, 1990), and CMV promoter. The vector may also carry an inducible promoter, for example, a doxycycline inducible promoter, or a promoter that may be activated to express Xist RNA by excision of intervening sequences, using a Cre-lox system. More generally, the nucleic acid construct that includes a silencing sequence can also include one or more control elements that facilitate expression of the silencing sequences. These control elements include promoter, enhancer, and termination sequences, and the promoter may be a constitutively active, inducible, tissue-specific or developmental stage-specific promoter.

Our findings further support the conclusion that chromosome inactivation also occurs in mature cells (e.g., in differentiated cells), but at a slower rate than in embryonic cells. Regarding developmental competence, we note that, in addition to the requirement for expression of an integrated Xist transgene, the cells must respond to Xist to support initiation of chromosome inactivation, which normally occurs during the earliest transition of pluripotent embryonic stem cells to more committed/differentiated cells. While all somatic cells in adult females are competent to maintain the silenced state, it has been believed that only early embryonic stem cells can initiate chromosome silencing in response to Xist. A study in mouse ES cells reported that if expression of Xist was delayed just two days after differentiation, the cells had lost the competence to initiate chromosome inactivation (Wutz et al. 2000, Molecular Cell). However, our study in human somatic cells (Hall et al., 2002, PNAS) first showed that a randomly integrated Xist transgene was able to initiate chromosome inactivation of the autosome (carrying the ectopic Xist gene) in human HT1080 cells, derived from an adult male fibrosarcoma. Our studies in Chow et al. (PNAS 2007) confirmed this for HT1080 cells and human 293 cells; however, because both of these somatic cell lines have neoplastic origins, it has been thought that their capacity to initially form the heterochromatic chromosome may not reflect the capacity of fully normal cells. However, in other work, we and others have shown that cancer cells tend to lose heterochromatin, including Xi (Pageau et al., 2007, Nature Reviews Cancer).

To further investigate whether normal, non-neoplastic somatic cells are competent to initiate chromosome inactivation post-differentiation, we differentiated mouse ES cells carrying an inducible-Xist transgene, essentially the same experimental system used in Wutz et al. Our findings demonstrate that these normal murine ES cells are able to support chromosome silencing post-differentiation. ES cells were differentiated for several (4-9) days prior to induction of Xist expression with doxycycline, and then cells were evaluated at various intervals up to two weeks following Xist expression. Whereas Wutz et al. waited just 2 days after Xist expression to evaluate whether chromosome silencing had taken place, we surmised that the multi-step inactivation process may occur more slowly in somatic cells. Indeed, our findings demonstrate that the vast majority of cells in these differentiated cultures had supported chromosome silencing, between 7-14 days after Xist expression. Thus, these findings indicate that the successful chromosome silencing in Hall et al. (2002) was likely not due to the neoplastic nature of the cells used, but to the long, ten-day time-frame over which the cells were evaluated.

While naturally occurring stem cells may have an enhanced competence to respond to Xist to initiate chromosome silencing, differentiated somatic cells, such as fibroblasts, can also be induced to form induced pluripotent stem cells (iPS cells) by introduction of specific genes that control developmental programs. The iPS cells have properties essentially like those of ES cells, and thus would be competent to not only initiate X-inactivation in response to Xist, but to form a variety of stem cells committed to specific cell types, such as neural, hematopoeitic, cardiac myoblasts, etc., which may enhance their therapeutic utility.

The present nucleic acid constructs can be used to integrate a silencing sequence (e.g., the Xist transgene) into a chromosome in murine or human embryonic, iPS, or adult stem cells (for example, see Zhang, *J. Hematotherapy & Stem Cell Research* 12:625-634, 2003, herein incorporated by reference). For example, bone marrow stem cells and induced pluripotent stem cells may be used. Pluripotency can be induced as described above by the methods of Wernig et al. (*Nature* 448:318-325, 2007); Shi et al. (*Cell Stem Cell.* 2:525-528, 2008); and Nakagawa et al. (*Nature Biotechnol.,* 26:101-106, 2008), all of which are incorporated by reference herein. In addition, neural precursor cells as described in Zhang et al. (*Nature Biotechnology,* 19:1129-1133, 2001) may be used. For example, the following steps could be used to generate a population of corrected patient stem cells of a particular type that will not be subject to immune rejection (because they are isogenic to the patient's DNA), but which can provide therapeutic value. 1) providing fibroblasts or lymphocytes or other cells from a patient with trisomy 21 (Down Syndrome); 2) treating these cells with reprogramming factors shown to generate induced pluripotent stem cells or early developmental cells; 3) introducing into these cells a zinc finger nuclease (with Fok1 recombinase) specifically designed to promote efficient integration of exogenous DNA at a specific location; 4) introducing an Xist transgene flanked by sequences homologous to the desired site of integration under the control of a promoter designed to be expressed as desired, and verifying that Xist is expressed and silences the chromosome; and 6) culturing the Xist-transgenic iPS cells under conditions that promote the generation of neural, hematological, cardiac or other desired stem cells. The corrected stem cells (in which the deleterious chromosome or region has been silenced) can then be reintroduced into the patient's body so as to achieve therapeutic benefit, by introducing the appropriate type of stem cells into the appropriate tissue or organ. For example, in Down Syndrome there is thought to be loss of neurons or neural function that appears to be progressive with age that contributes to mental retardation. Similarly, Alzheimer's Disease is associated with loss of proper neuron function. As has been shown in mouse models of another neurological disease, intracranial injection of normal neural stem cells can provide therapeutic benefit (Lee et al., *Nature Med.* 13:439-447, 2007) and, more generally, cell implantation methods, including via intracranial surgery, are known in the art. Similarly, Down Syndrome is associated with hematological abnormalities that could be treated by correcting patient cells that are natural bone marrow stem cells or induced bone marrow stem cells (from iPS cells or other mesenchymal stem cells). In a patient with TMD (transient myeloproliferative disorder, which often precedes leukemia) or leukemia, the corrected bone marrow stem cells could be introduced into the patient's blood, to repopulate the bone marrow with more normal stem cells. Similarly, babies with Down Syndrome have a high rate of congenital heart defects, which in some cases could be treated by the use of cardiac stem cell therapy, where the stem cells used would be isogenic with the patient's DNA but would be corrected by silencing the trisomic chromosome.

In addition, the vector may contain a marker for the selection of transfected cells (for instance, a drug resistance gene for selection by a drug such as neomycin, hygromycin, and G418). Such vectors include pMAM, pDR2, pBK-RSV, pBK-CMV, pOPRSV, pOP13, and so on. More generally, the term "marker" refers to a gene or sequence whose presence or absence conveys a detectable phenotype to the host cell or organism. Various types of markers include, but are not limited to, selection markers, screening markers, and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as green fluorescent protein (GFP), GUS or β-galactosidase. Molecular markers are, for example, sequence features that can be uniquely identified by oligonucleotide probing, for example RFLP (restriction fragment length polymorphism), or SSR markers (simple sequence repeat). To amplify the gene copies in host cell lines, the expression vector may include an aminoglycoside transferase (APH) gene, thymidine kinase (TK) gene, *E. coli* xanthine guanine phosphoribosyl transferase (Ecogpt) gene, dihydrofolate reductase (dhfr) gene, and such as a selective marker.

In vivo expression of the DNA of the invention may be performed by constructing the DNA into an appropriate vector and transfecting the construct into the body using retrovirus, liposome, cationic liposome, adeno-associated virus (particularly where chromosome 19 is targeted), lentivirus, electroporation and so on. It is possible to use such a construct to perform gene therapy for diseases resulting from chromosomal trisomies and/or translocations or duplications. Examples of vectors used for this purpose include retrovirus vector (such as pZIPneo), but are not limited thereto. General manipulations, such as insertion of the DNA into the vector, may be performed by using standard methods (Molecular Cloning, 5.61-5.63). The vector may be administered to the patient through in vivo administration or by way of methods that are carried out, at least partially, ex vivo. For example, the vector may be administered to cells harvested from a patient and maintained in culture. The construct-carrying or vector-carrying cells can then be introduced to the patient. For example, stem cells or hematopoietic cells can be harvested from a patient or obtained from another source, modified in culture as described here to include insertion of a silencing sequence into a targeted site, and administered to the patient. To facilitate the method, the recipient patient may be subjected to bone marrow ablation.

Facilitating targeting with zinc finger nucleases: Targeting the present "silencing" constructs to particular chromosomes or regions of chromosomes can be facilitated by introducing chimeric zinc finger nucleases (ZFNs) into a cell. These nucleases exploit endogenous cellular mechanisms for homologous recombination and repair of double stranded breaks in genetic material. ZFNs can be used to target a wide variety of endogenous nucleic acid sequences in a cell or organism. The present compositions include cleavage vectors that target a ZFN to a region within a trisomic chromosome or within a translocated sequence, and the methods include transfection or transformation of a host cell or organism by introducing a cleavage vector encoding a ZFN (e.g., a chimeric ZFN), or by introducing directly into the cell the mRNA that encodes the recombinant zinc finger nuclease, or the protein for the ZFN itself. One can then identify a resulting cell or organism in which a selected endogenous DNA sequence is cleaved and exhibits a mutation or DNA break at a specific site, into which the transgene will become integrated.

To help clarify the nucleic acid to which we are referring, we tend to use the term "nucleic acid construct" to describe a nucleic acid that includes the silencing sequence and the term "cleavage vector" to describe a nucleic acid that encodes the ZFN. It is to be understood, however, that both are, or include, nucleic acid sequences (e.g., DNA); both can be properly referred to as constructs; and both can be properly referred to as vectors, particularly when they include nucleic acid sequences that facilitate entry into a host cell.

The methods can include construction of a vector or isolation of an mRNA encoding a chimeric ZFN by, for example, selecting a zinc finger DNA binding domain capable of preferentially binding to a specific host DNA locus to be mutated; further selecting a non-specific DNA cleavage domain capable of cleaving double-stranded DNA when operatively linked to the binding domain and introduced into the host cell; further selecting a promoter region capable of inducing expression in the host cell; and further operatively linking DNA encoding the binding domain and the cleavage domain and the promoter region to produce a DNA construct. Elements are operatively linked when they work in concert. For example, a control element and a transgene are operatively linked when the control element alters the expression of the transgene. To bring a transgene under the control of a promoter, one positions the 5' end of the transcription initiation site of the transcriptional reading frame generally between about 1 and about 50 nucleotides "downstream" (i.e., 3') of the chosen promoter. The "upstream" promoter stimulates transcription of the DNA.

The nucleic acid (e.g., DNA) construct is then introduced into a target host cell and at least one host cell exhibiting recombination at the target locus in the host DNA is identified.

The ZFN can be a chimeric protein molecule that directs targeted genetic recombination or targeted mutation in a host cell by causing a double stranded break at the target locus. For example, a ZFN can include a DNA-binding domain that includes at least one zinc finger, and that binding domain can be operatively linked to a DNA-cleavage domain. The DNA-binding domain is at the N-terminus of the chimeric protein molecule, and the DNA-cleavage domain is located at the C-terminus of the molecule.

The ZFN can include multiple (e.g., at least three (e.g., 3, 4, or 5)) zinc fingers in order to improve its target specificity. The zinc finger domain can be derived from any class or type of zinc finger. For example, the zinc finger domain can include the $Cys_2His_2$ type of zinc finger that is very generally represented, for example, by the zinc finger transcription factors TFIIIA or Sp1. In a preferred embodiment, the zinc finger domain comprises three $Cys_2His_2$ type zinc fingers.

The DNA recognition and/or the binding specificity of a ZFN can be altered in order to accomplish targeted genetic recombination at any chosen site in cellular DNA. Such modification can be accomplished using known molecular biology and/or chemical synthesis techniques. ZFNs comprising zinc fingers having a wide variety of DNA recognition and/or binding specificities are within the scope of the present invention.

The ZFN DNA-cleavage domain can be derived from a class of non-specific DNA cleavage domains, for example the DNA-cleavage domain of a Type II restriction enzyme such as FokI. Thus, a chimeric ZFN useful in the present methods can include three $Cys_2His_2$ type zinc fingers and a DNA-cleavage domain derived from the Type II restriction enzyme FokI. In this event, each zinc finger contacts three consecutive base pairs of DNA creating a 9 bp recognition sequence for the ZFN DNA binding domain. The DNA-cleavage domain of the embodiment requires dimerization of two ZFN DNA-cleavage domains for effective cleavage of double-stranded DNA. This imposes a requirement for two inverted recognition (target DNA) sites within close proximity for effective targeted genetic recombination. If all positions in the target sites are contacted specifically, these requirements enforce recognition of a total of 18 base pairs of DNA. There may be a space between the two sites. The space between recognition sites for ZFNs may be equivalent to 6 to 35 bp of DNA. The region of DNA between the two recognitions sites may be referred to as the "spacer".

A linker, if present, between the cleavage and recognition domains of the ZFN can be a sequence of amino acid residues that result in a flexible linker is flexible, although linkerless constructs tend to improve target site specificity. A linkerless construct has a strong preference for binding to and then cleaving between recognition sites that are 6 bp apart. However, with linker lengths of between 0 and about 18 amino acids in length, ZFN-mediated cleavage occurs between recognition sites that are between 5 and 35 bp apart. For a given linker length, there will be a limit to the distance between recognition sites that is consistent with both binding and dimerization. As noted, there may be no linker between the cleavage and recognition domains, and the target locus can include two nine nucleotide recognition sites in inverted orientation with respect to one another, separated by a six nucleotide spacer.

To target genetic recombination or mutation, two 9 bp zinc finger DNA recognition sequences are identified in the host DNA. These recognition sites will be in an inverted orientation with respect to one another and separated by about 6 bp of DNA. ZFNs are then generated by designing and producing zinc finger combinations that bind DNA specifically at the target locus, and then linking the zinc fingers to a cleavage domain of a Type II restriction enzyme.

A silencing sequence flanked by sequences (typically 400 bp-5 kb in length) homologous to the desired site of integration can be inserted (e.g. by homologous recombination) into the site cleaved by the endonuclease, thereby achieving a targeted insertion. When used in combination with a ZFN construct, the silencing sequence may be referred to as "donor" nucleic acid or DNA.

The various active sequences, including the silencing sequence and the sequence encoding a chimeric ZFN can be introduced into a host cell on the same vector or separately (e.g., on separate vectors or separate types of vectors at the same time or sequentially). Methods for introducing the various nucleic acids, constructs, and vectors are discussed further below and are well known in the art.

The nucleic acid constructs including a silencing sequence, whether used alone or in combination with a ZFN can either introduce a therapeutic sequence or disrupt a targeted sequence, gene, or chromosome in a somatic cell or in a germ cell. In some cases, a therapeutic Xist transgene may be inserted in such a way as to simultaneously disrupt a deleterious gene, such as the APP gene that leads to high incidence of Alzheimer's. Cells with such disruption in the targeted gene can be "selected for" in order to create an organism without a functioning target sequence or for administration to a patient. Accordingly, the constructs, other compositions, and methods of the present invention are applicable to a wide range of cell types and organisms. While our own intention is to develop therapies for human patients, the silencing methods we have discovered can be carried out with a single celled or multicellular organism; an oocyte; a gamete; a germline cell in culture or in a host organism; a somatic cell in culture or in a host organism; an insect cell, including an insect selected from the group consisting of Coleoptera, Diptera, Hemiptera, Homoptera, Hymenoptera, Lepidoptera, or Orthoptera, including a fruit fly, a mosquito and a medfly; a plant cell, including a monocotyledon cell and a dicotyledon cell; a mammalian cell, including but not limited to a cell of a mouse, rat, pig, sheep, cow, dog, cat, or human; an avian cell, including, but not limited to a cell of a chicken, turkey, duck or goose; or a fish cell, including, but not limited to zebrafish, trout and salmon.

DNA encoding an identifiable marker can also be included with either the nucleic acid construct including the silencing sequence or the vector carrying the ZFN-encoding sequence. Such markers may include a gene or sequence whose presence or absence conveys a detectable phenotype to the host cell or organism. Various types of markers include, but are not limited to, selection markers, screening markers and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as Green Fluorescent Protein (GFP), beta-glucuronidase (GUS) or beta-galactosidase. Markers may also be negative (e.g., codA) or positive selectable markers. Molecular markers are, for example, sequence features that can be uniquely identified by oligonucleotide probing, for example RFLP (restriction fragment length polymorphism), or SSR markers (simple sequence repeat).

The compositions and methods described herein can be used to accomplish germline gene therapy in mammals.

The frequency of homologous recombination in any given cell is influenced by a number of factors. Different cells or organisms vary with respect to the amount of homologous recombination that occurs in their cells and the relative proportion of homologous recombination that occurs is also species-variable. The length of the region of homology between donor and target affects the frequency of homologous recombination events, the longer the region of homology, the greater the frequency. The length of the region of homology needed to observe homologous recombination is also species specific. However, differences in the frequency of homologous recombination events can be offset by the sensitivity of selection for the recombinations that do occur. It will be appreciated that absolute limits for the length of the donor-target homology or for the degree of donor-target homology cannot be fixed but depend on the number of potential events that can be scored and the sensitivity of the selection for homologous recombination events. Where it is possible to screen $10^9$ events, for example, in cultured cells, a selection that can identify 1 recombination in $10^9$ cells will yield useful results. Where the organism is larger, or has a longer generation time, such that only 100 individuals can be scored in a single test, the recombination frequency must be higher and selection sensitivity is less critical. Random integration is discussed elsewhere herein. We note here, however, that random integration can be used in combination with selection for cells that have targeted the desired gene or chromosome.

Transformation can be carried out by a variety of known techniques which depend on the particular requirements of each cell or organism. Such techniques have been worked out for a number of organisms and cells and are readily adaptable. Stable transformation involves DNA entry into cells and into the cell nucleus. For single-celled organisms and organisms that can be regenerated from single-cells (which includes all plants and some mammals), transformation can be carried out in culture, followed by selection for transformants and regeneration of the transformants. Methods often used for transferring DNA or RNA into cells include forming DNA or RNA complexes with cationic lipids, liposomes or other carrier materials, micro-injection, particle gun bombardment, electroporation, and incorporating transforming DNA or RNA into virus vectors. Other techniques are well known in the art.

Where silencing is limited to less than an entire chromosome, boundary elements or sequences associated with escape from inactivation can be used to help impede the spread of the silencing RNA. For a description of a unique sequence feature of the X-chromosome that always escapes inactivation see McNeil et al. (*Genome Res.* 16:477-484, 2006). This sequence is among those that can be used to confer "escape" from silencing. See also Filippova et al. (*Dev. Cell.* 8:31-42, 2005).

In the following paragraphs, we describe some delivery systems useful in practicing the present invention.

Liposomal formulations: In certain embodiments of the invention, the oligo- or polynucleotides and/or expression vectors containing silencing sequences and/or ZFNs may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Also contemplated are cationic lipid-nucleic acid complexes, such as lipofectamine-nucleic acid complexes. Lipids and liposomes suitable for use in delivering the present constructs and vectors can be obtained from commercial sources or made by methods known in the art.

Microinjection: Direct microinjection of DNA into various cells, including egg or embryo cells, has also been employed effectively for transforming many species. In the mouse, the existence of pluripotent embryonic stem (ES) cells that can be cultured in vitro has been exploited to generate transformed mice. The ES cells can be transformed in culture, then microinjected into mouse blastocysts, where they integrate into the developing embryo and ultimately generate germline chimeras. By interbreeding heterozygous siblings, homozygous animals carrying the desired gene can be obtained.

Viral Vectors as Expression Constructs: Other viral vectors may be employed as expression constructs in the present invention. Vectors derived from, for example, vaccinia virus, adeno-associated virus (MV), and herpes viruses may be employed. Extensive literature is available regarding the construction and use of viral vectors. For example, see Miller et al. (*Nature Biotechnol.* 24:1022-1026, 2006) for information regarding adeno associated viruses. Defective hepatitis B viruses, may be used for transformation of host cells. In vitro studies show that the virus can retain the ability for helper-dependent packaging and reverse transcription despite the deletion of up to 80% of its genome. Potentially large portions of the viral genome can be replaced with foreign genetic material. The hepatotropism and persistence (integration) are particularly attractive properties for liver-directed gene transfer. The chloramphenicol acetyltransferase (CAT) gene has been successfully introduced into duck hepatitis B virus genome in the place of the viral polymerase, surface, and pre-surface coding sequences. The defective virus was cotransfected with wild-type virus into an avian hepatoma cell line, and culture media containing high titers of the recombinant virus were used to infect primary duckling hepatocytes. Stable CAT gene expression was subsequently detected.

Non-viral Methods: Several non-viral methods are contemplated by the present invention for the transfer into a host cell of DNA constructs encoding ZFNs and, when appropriate, donor DNA. These include calcium phosphate precipitation, lipofectamine-DNA complexes, and receptor-mediated transfection. Some of these techniques may be successfully adapted for in vivo or ex vivo use.

In one embodiment of the invention, the expression constructs may simply consist of naked recombinant DNA, or in some cases mRNA for the recombinant ZFN. Transfer of the construct may be performed by any of the nuclei acid transfer methods mentioned above which physically or chemically permeabilize the cell membrane. For example, polyomavirus DNA in the form of $CaPO_4$ precipitates was successfully injected into liver and spleen of adult and newborn mice which then demonstrated active viral replication and acute infection. In addition, direct intraperitoneal injection of $CaPO_4$ precipitated plasmid expression vectors results in expression of the transfected genes.

EXAMPLES

Silencing a trisomic chromosome in human somatic cells and in a trisomic mouse model of DS: We will introduce an Xist transgene into human and mouse trisomic cells, and demonstrate silencing of the trisomic chromosome in culture. We believe that human Xist transgenes can: (1) initiate silencing outside of the normal very early development window in normal (non-neoplastic) human somatic cells and/or stem cells; (2) be targeted to and effectively silence an autosome (e.g., trisomic human chromosome 21) in human cultured cells; and with higher efficiency techniques, (3) stably silence the trisomic chromosome in mouse ES cells and mice in an established mouse model of Down Syndrome, thereby ameliorating the deleterious phenotype. Trisomic mouse models of Down Syndrome are available and can be used to test both chromosome silencing and amelioration of the phenotype of DS mice (see below).

Experiments in Mouse ES or iPS Cells and a Mouse Model of Down Syndrome: The goal of these studies is to first target an Xist transgene into ES, iPS or bone marrow cells derived from one or more mouse models of Down Syndrome and verify that the trisomic chromosome is effectively silenced. Two available mouse DS models carry trisomy chr. 16 (syntenic to human 21) and one carries an actual human Chr 21 as the third chromosome (further detailed below).

Trisomic mouse models of DS: Mouse chromosome 16 is largely syntenic to human chromosome 21, and mouse models of DS have been developed that are either trisomic for mouse chr. 16, or carry as the third chromosome an actual human chromosome 21 (reviewed in Reeves *Trends Mol. Med.* 12:237-240, 2006). There are mouse strains with segmental trisomies, such as Ts65Dn, which carries a segment (15.6-Mb) of mouse chromosome 16 on a marker chromosome (Reeves et al., *Nat. Genet.* 11:177-184, 1995). The extra $T(17^{16})$65Dn marker chromosome produces a trisomy for the mouse orthologs of about half of the human genes on chr. 21. Mice display a number of DS-like phenotypes, including an overall reduction in size and growth rate, altered noradrenergic transmission in the hippocampus and cerebral cortex and degeneration of basal forebrain cholinergic neurons, and defects in cranial bone development (Hill et al., *J. Anat.* 210:394-405, 2007; Olson et al., *Hum. Mol. Genet.* 16:774-782, 2007). In addition, trisomic females have smaller and fewer litters and trisomic males display hypospermia. Another mouse model, Ts16, carries an essentially complete third copy of mouse chr. 16, involving a Robertsonian translocation of chr 16 (Epstein et al., *Ann. NY Acad. Sci.* 450:157-168, 1985). As with other mouse full trisomies, these mice die during fetal development, so all studies are done on the fetal mice or cells derived from fetuses. However, for our purposes the severity of the phenotype would potentially make the therapeutic benefits clearer, if we should see an increase in viability upon inactivation of one copy of chromosome 16. The Rb(6.16)24Lub/Rb(16.17)7Bnr$F_1$ Robertsonian translocation mouse strain (used to generate Ts16) and the Ts65Dn mouse strain are available from the Jackson Laboratory.

Another interesting mouse DS model (Tc1) carries an almost complete human chromosome 21, and exhibits several characteristics that are reminiscent of Down Syndrome (O'Doherty et al., *Science* 309:2033-2037, 2005). However, this model is less attractive as it is not clear how well human Xist would silence a human chromosome in an otherwise mouse nucleus; our prior study of mouse/human hybrids showed that human Xist RNA may not localize properly. Thus, we have decided to begin with the Ts65n model which carries a partial chr 16 trisomy and is more straightforward. We summarize the approach for this system, but other models can be tested similarly.

Generation of mouse Down's syndrome ES cells and iPS cells: The Ts65Dn mouse model (B6EiC3Sn a/A-Ts($17^{16}$)65Dn) has been obtained from the Jackson Laboratory (stock number 001924) (Roper et al., *Genetics* 172:437-443, 2006). Female $T(17^{16})$65Dn mice have been mated to 129SV/EV males, and a number of litters produced. DS pups have been identified by karyotyping cytogenetic preps, and using FISH on interphase cells from tail tip fibroblasts and whole blood.

Generation of trisomic ES cells: Blastocysts will be harvested from the mating of Ts65Dn females with 129SV/EV males, to derive ES cells, using standard procedures. DS embryos can also be generated by somatic cell nuclear transfer of a fibroblast from a Ts65Dn mouse into an enucleated normal mouse egg.

Generation of trisomic iPS cells: Fibroblasts from DS pups have been isolated and iPS cells generated using lentivirus expression of 4 pluripotency genes (mOct4, mSox2, mKlf4, mc-Myc). Twenty hours post-transduction, the virally transduced cells were resuspended in ES cell growth medium and re-seeded. The following day the pluripotency genes were induced with doxycycline. Colonies that appear (ours started showing up by day 3), are replated onto inactivated feeder MEFs. Doxycycline is removed once colonies are verified to express the other pluripotency markers (SSEA-1, Nanog, etc), between 14 and 22 days. Resulting colonies are then cultured on feeders in the absence of dox, similar to normal mouse ES cells. These iPS cells can now be used to target Xist to chromosome 16.

Targeting the Xist transgene to a trisomic chromosome in mouse cells and assessing silencing of Chr 16: The Xist transgene will be targeted into a specific region of chromosome 16 in the trisomic iPS cells. We will target the region critical for Down's syndrome on chromosome 16, using as preferred targeting sites some of the genes important to the pathology of Down's syndrome (e.g. Runx-1, APP, Dyrk1A, etc). The transgene can have a constitutive or inducible promoter. We have begun to construct a targeting transgene which incorporates Xist cDNA sequences from an Xist cDNA that we have obtained by Anton Wutz (Research Institute of Molecular Pathology, Vienna) (Savarese et al., *Mol. Cell. Biol.* 26:7167-7177, 2006). This Xist transgene contains a inducible promoter and Xist cDNA, but lacks the 3' sequence necessary for counting. Thus, it will not be susceptible to random inactivation in the female ES cells. We are modifying this transgene with appropriate promoters, homologous targeting sequences, and inducible system to make it appropriate for targeting the Xist transgene to the specific chromosome in iPS cells. It will be expressed during cell differentiation, for optimal silencing.

We will be using established mouse gene targeting protocols on our iPS cells. We are currently designing an Xist targeting construct using a vector previously validated to efficiently target the Runx1 gene. Runx1 is located in the critical region of chr16, has been linked to leukemia, and likely plays a role in the hematological abnormalities seen in DS individuals (mouse and human). The targeting vector can also include a GFP mini-gene to facilitate identification of transgenic cells and to confirm silencing of this gene. Selectable markers will facilitate identification of properly targeted clones, using known procedures. Similarly, targeting can be to the APP gene which is known to be important to Alzheimer's Disease or other gene important in other diseases.

In mouse models of DS, we can not only manipulate mouse ES or iPS cells, which are known to support chromosome silencing, but also test two critical points in the proof-of-principle: that stable silencing of the third chromosome (carrying an Xist transgene) can be achieved, and that this can have ameliorating effects on the disorder, at the whole organism level. Our plan is to initially target the Xist transgene into a trisomic chromosome of "Down Syndrome" mouse ES/iPS cells, induce silencing and confirm that it silences, and then generate mice (or chimeric mice) from these engineered ES/iPS cells. If this procedure successfully silences and mitigates the phenotype, we can use an inducible promoter to induce Xist expression at later stages of development, to determine how late effective silencing and mitigation of the disorder can be achieved. Also, the original TS64DN non-modified mice may also be used to examine the effects of reintroducing bone marrow, after chromosome modification, on the hematological abnormalities in DS mice (these studies are further detailed below).

Figure 5:
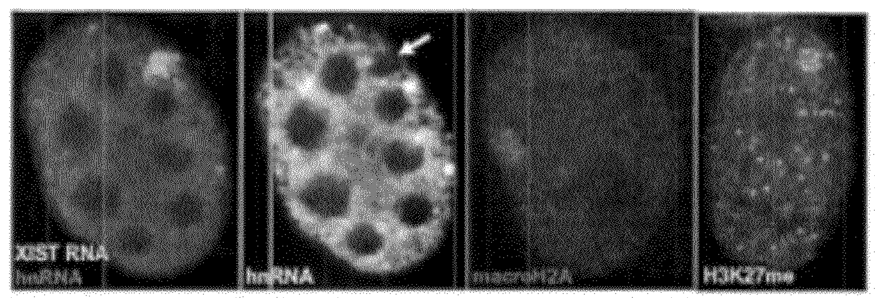
FIG. 5 is a panel of four images of the same cell showing, from left to right, Xist RNA localization, hnRNA, macroH2A localization, and H3K27me localization.

Validation of targeting and silencing: As we have previously published, single cell analysis by molecular cytological methods (immunofluorescence and FISH), will be used to validate targeting and the extent of chromosomal silencing in differentiated iPS cell cultures (FIG. 5). RNA FISH for single genes or real-time PCR or microarrays will be used to examine gene expression levels in targeted versus non-targeted iPS cells. We will initially determine by fluorescence in situ hybridization whether the Xist gene is expressing and producing a localized accumulation that "paints" the chromosome. This is a very distinctive relationship of RNA to the chromosome that is almost always correlated with silencing, which our lab first discovered and established (Clemson et al., *J. Cell Biol.* 132:259-275, 1996). If Xist RNA coated chromosomes are observed, we will then use other Xi hallmarks (e.g. hybridization to hnRNA, immunofluorescence to H3K27 methylation or macroH2A) to further validate the silencing, as shown in FIG. 5 and in our published papers.

In addition, as stated above, we will generate mice from the modified mouse iPS (or ES) cells to test the prediction that the trisomic chromosome can be silenced and the deleterious phenotype will be substantially ameliorated (this is further detailed below).

Experiments in human primary or iPS Down syndrome Cells: Several DS human cell types are available to generate DS iPS lines from, including DS patient fibroblasts and bone marrow. We have acquired three primary DS fibroblast lines and two bone marrow cell lines, and have TERT immortalized one female DS fibroblast line. We plan to generate iPS cells from both primary as well a TERT immortalized DS lines, using lentivirus expression of 4 pluripotency genes similar to the methodology used in developing the mouse DS iPS cell lines. We have also acquired a DS iPS line from Harvard Stem Cell Institute.

Studies in Human Primary Cells: Although iPS cells can now be made from primary lines, we can also test the developmental competence of terminally differentiated primary human cells to support silencing in response to an inducible Xist transgene integrated into an autosome. This may help define whether more differentiated cell types may also be available for chromosome therapy in the future. Some of our studies have been aimed at determining whether somatic or only stem cells can support chromosome silencing of an autosome. A prior study of transgenic mouse ES cells concluded that Xist did not induce silencing just a few days after the earliest embryonic differentiation (Wutz et al.), however this study examined silencing just two days after Xist expression. We have shown that adult human somatic cells can initiate silencing of an autosome carrying an Xist transgene (Hall et al., *Proc. Natl. Acad. Sci. USA* 99:8677-8682). However, the study indicated this took at least 10 days to occur in somatic cells. Thus, we will examine chromosome silencing after two or more weeks and are hopeful that somatic cells will largely retain the ability to induce chromosome silencing, albeit more slowly than in ES cells. Our recent findings indicate that human ES cells (hESCs) also support silencing of the normal X chromosome in culture similar to that seen for the mouse. We have also derived a sub-line of neural stem cells (from hESCs), and we will test their competence to support silencing, which may be particularly relevant to future DS therapeutic applications. It may also be possible to partially reprogram somatic cells, such that they more closely resemble adult stem cells instead of ES/iPS cells, and assess the competence of these partially reprogrammed cells to inactivate.

Wutz lab (Savarese et al., *Mol. Cell. Biol.* 26:7167-7177, 2006) suggests that bone marrow stem cells may retain capacity to support chromosome silencing post-embryonic differentiation, but our close reading of this data suggests to us that some or many more cell-types in fetal or adult mice still retain the capacity for X-inactivation. For reasons summarized below, we are particularly interested in testing this strategy in DS bone marrow cells. Thus, for these experiments, rather than use transformed cell lines, we will test several different primary somatic cell types, including DS patient fibroblasts and bone marrow cells, primary diploid myoblasts, epithelial cells, and trisomic amniocytes (available from Coriell Cell Repositories, Camden, N.J.). The developmental competence of these cells will be compared to TERT immortalized primary DS lines, and embryonic and neural stem cells, including those derived from induced pluripotent stem (iPS) cells generated from patient somatic cells.

These questions regarding the developmental competence of cells to enact chromosome silencing do not require targeted integration (we will use the methodology that provides the highest efficiency of integration), and is similar to work we have done successfully with transformed cell lines.

Incorporation of the ZFN technology to target the Xist transgene to a trisomic chromosome in human cells and assess silencing of Chr 21 (or Chr 13): We will test the best strategies to target human Chr 21 (or Chr 13) and to confirm the effectiveness of silencing. Conventional targeting strategies as well as a new zinc-finger based methodology will be used for targeting the Xist transgene to Chr 21. This will be assessed both with and without the use of selection, and by using the endogenous or an inducible promoter (as in our papers). Selection might be utilized with future ES/iPS methodologies, but would not be an option in vivo; see Moehle et al. (*Proc. Natl. Acad. Sci. USA,* 104:3055-3060, 2007). The constructs lack the sequences 3' to Xist that trigger the "counting" mechanism, so this will not complicate results.

We will use site-specific targeting, using zinc finger nucleases (ZFNs). This approach provides much higher integration efficiency, without a requirement for selection. More specifically, this method uses the cells own machinery for double strand break repair to improve the efficiency of gene targeting. The zinc finger motifs can be engineered to recognize almost any sequence, and we will engineer ZFN transgenes that target two or more sites of Chr. 21. The transgene encoding the ZFN can be introduced along with a vector carrying the gene to be inserted flanked by a few hundred by of DNA homologous to the target site. Recent studies have achieved targeted integration rates of about 5 to 20% without selection with integration of up to 8 kb of DNA (Urnov et al., *Nature* 435:646-651, 2005; Moehle et al., *Proc. Natl. Acad. Sci. USA* 104U; 3055-3060, 2007). If very high efficiency is obtained, it is possible that we could get integration into two copies of the chromosome in some cells. If this occurs, we will target polymorphic sites. In addition, these methods have shown particular promise for use in human ES cells.

We will begin these studies in 293 cancer cells that transfect at very high efficiency, and then move on to TERT immortalized trisomy 21 fibroblasts, and iPS cells generated from these DS lines. We anticipate that most autosomal material is competent to be inactivated in response to Xist RNA. However, because there is some sequence specificity to this process, we will determine the effectiveness of chromosome 21 silencing specifically using molecular cytological assays. Presuming this shows silencing, we will use microarray analysis to determine the profile of gene expression for Chr. 21 genes, in comparison to the trisomic cells (without the transgene) and normal cells. In addition to the trisomy 21 cells, one of the human ES cell lines approved by the NIH carries a trisomy for chr. 13. We will study chr. 13 inactivation in these cells, both as undifferentiated ES cells and as cells differentiated along a neuronal pathway.

Utilizing random integration of Xist: In some studies, we will use the ZFN technology described above, but analyses can also be done using our protocol for random integration with the same constructs and transfection approach that we have successfully used before (Hall et al. 2002b; Chow et al. 2007). In these experiments, transgenes can be designed to select against cells in which the trangene has not integrated. If integration is into a disomic chromosome which is then silenced, this would create a functional monosomy, which would reduce or severely reduce cell viability. In contrast, if the random integration involved the trisomic chromosome in a DS cell line, there is likely to be a growth advantage to these "corrected" cells within the population, and this, coupled with selection against cells where integration generated a functional monosomy, may generate a strong selection for the desired cells in which the random integration was into the trisomic chromosome, even without targeting methodologies. This same natural selective disadvantage of functionally monosomic cells may provide a natural protection against the less frequent occurrence that two of the trisomic chromosomes are silenced, as such cells would be selected against as they are in human development. (In individuals mosaic for Down Syndrome where a non-disjunction even generates a trisomic cell-line and a monosomic cell line, the monosomic cell line is not see; these cells die.) However, we have also shown that transfectants can be selected for drug expression (prior to chr. inactivation), and the integration site and impact on chromosome silencing can be determined in several different clones or in pooled populations of random integrants.

Further Studies Using the Down's Syndrome Mouse Models

Use trisomic mouse ES/iPS cells carrying the Xist-transgene to generate mice and assess phenotype: The targeted ES/iPS cells can be injected into blastocysts of albino C57Bl/6 E3.5 to generate mice in which coat color changes can be used to assess the degree of chimerism or into the blastocysts of trisomic Ts65n blastocysts. The latter mice would be "mosaic" for the Xist-transgenic trisomic cells and uncorrected trisomic cells, providing a good model of partial correction. In addition, routine methods using blastocysts that have undergone tetraploid fusion can generate mice completely derived from the modified ES cells.

To assess the corrective effects of Xist-mediated silencing of the $T(17^{16})65Dn$ chromosome in this model for DS, we will measure birth weight and growth throughout the postnatal period, as well as correction of defects in craniofacial skeletal formation. Bone defects have been analyzed in mice using X-rays and microCT analysis (Lengner et al., *J. Cell Biol.* 172:909-921, 2006), and we will also examine hematopoietic properties and make appropriate crosses to determine whether the Xist transgene corrects the deficiency in male fertility. In addition, maintenance of gene silencing will be assayed in a variety of organs by both qPCR for genes present of the $T(17^{16})65Dn$ chromosome as well as by analysis of GFP expression, and by standard molecular cytological methods.

Relevance of trisomy 21 to hematological abnormalities and bone marrow stem cells: We will test this strategy to silence the trisomic chromosome in bone marrow cells. There is a direct and measurable clinical impact of trisomy on bone marrow function. DS children develop hematological abnormalities, ranging from mild to severe. For example, neonates with DS commonly develop a transient myeloproliferative disorder (TMD; also termed transient leukemia). Although TMD often is self-resolving, it is highly predictive of later development of acute leukemia, can result directly in significant morbidity, and may be fatal in 10-20% of affected infants. Most importantly, it is well established that DS children have a greatly increased risk of progressing to leukemia, such that 2% of childhood leukemia patients have DS. The incidence of ALL and AML is 20 fold higher than normal, and the normally very rare AMKL (acute megakaryoblastic leukemia) is increased a remarkable 500 fold (Lange, *Br. J. Haematol.* 110:512-524, 2000). Finally, most DS children have MCV (mean corpuscular volume) above the $97^{th}$ percentile. While not a significant clinical concern, this is indicative of disordered hematopoiesis and provides a prevalent "marker" of the syndrome (also in the mouse DS model), that could be readily evaluated in "corrected" cells.

Regarding the Ts65Dn model (above), an important report just appeared which demonstrates that it also provides a good model for many of the hematological abnormalities seen in human DS (Kirsammer et al., *Blood* 111(2), 2008). The DS mice exhibit a highly penetrant myeloproliferative disease, as well as macrocytosis, dysplastic megakaryocyte morphology, and myelofibrosis. Therefore, we will test the chromosome silencing strategy in bone marrow stem cells from the Ts65Dn mouse. In addition to the clinical impact of trisomy on hematological abnormalities, the study of bone marrow is advantageous because it is an accessible source of cells that can be genetically manipulated, and then replaced. Furthermore, a study of the Xist mechanism, using random integration of inducible Xist transgenes, provided evidence that hematopoeitic precursor cells of adult mice are most readily competent to support chromosome silencing (Savarese et al., *Mol. Cell. Biol.* 26:7167-7177, 2006). (This study was unrelated to any concept regarding therapeutic use of Xist transgenes.) We will use inducible mouse Xist transgene constructs as described in Savarese (supra), and we can include in these constructs GFP, which will facilitate sorting and enrichment of cells carrying the Xist transgene. Ultimately, the silencing of the transgenic chromosome would be verified using procedures described above and the modified cells will be reintroduced, after bone marrow ablation by radiation. At various intervals after "chromosome correction", hematological analysis will be carried out to determine whether or to what extent the aforementioned anomalies of the DS mouse, particularly the myeloproliferative disease and the prevalent macrocytosis, have been ameliorated.

Use of inducible Xist transgene to test phenotypic benefits later in development: To determine the extent of the therapeutic benefit achieved when the trisomic chromosome is silenced later in development, we will generate ES/iPS cells that contain the doxycyclin inducible Xist transgene, or another inducible Xist construct (e.g. Cre/Lox mediated removal of drug resistance gene generating a new construct where Xist is transcribed using the drug resistance promoter). The inducible Xist transgene can then be turned on in both undifferentiated ES/iPS cells as well as at different times during differentiation and in terminally differentiated cells to assess the developmental competence of inactivation.

The same inducible transgenic iPS/ES cells can be used to induce the "rescue" later in fetal development, allowing the evaluation of phenotypic benefits in more differentiated cells. Addition of doxycyclin to the drinking water of the pregnant dams bearing the chimeric mice for 14 days should result in activation of the tet promoter controlling Xist expression, and Xist-mediated silencing of the $T(17^{16})65Dn$ chromosome. A similar strategy has been used previously in mice to regulate Xist expression in hematopoietic precursor cells (Savarese et al., *Mol. Cell. Biol.* 26:7167-7177, 2006).

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising:

(i) a vector comprising a nucleic acid construct comprising:

a silencing sequence encoding an Xist RNA; and first and second sequences that direct insertion of the silencing sequence into human chromosome 13, 18, or 21 or mouse chromosome 16; and (ii) a nucleic acid encoding a chimeric zinc finger nuclease (ZFN), or a ZFN polypeptide, that targets the human chromosome 13, 18, or 21 or mouse chromosome 16.

2. The composition of claim 1, wherein the silencing sequence is a full-length Xist gene sequence.

3. The composition of claim 1, wherein the silencing sequence is an Xist gene sequence exclusive of one or more introns.

4. The composition of claim 1, wherein the silencing sequence comprises about 6 kb to about 10 kb of exon 1 of an Xist gene sequence.

5. The composition of claim 4, wherein the silencing sequence comprises the Xist cDNA sequence having accession number M97168 or a biologically active fragment or other variant thereof.

6. The composition of claim 1, wherein the silencing sequence comprises a biologically active fragment or other biologically active variant of a naturally occurring Xist gene sequence.

7. The composition of claim 1, further comprising a regulatory sequence.

8. The composition of claim 7, wherein the regulatory sequence is a constitutively active, inducible, tissue-specific, or developmental stage-specific promoter.

9. The composition of claim 1, wherein the first and second sequences direct insertion of the silencing sequence into a polymorphic region of the targeted chromosome.

10. An isolated trisomic cell comprising the composition of claim 1.

11. The isolated trisomic cell of claim 10, wherein the cell is a somatic cell or a stem cell.

12. The composition of claim 1, wherein the vector comprising the nucleic acid construct further comprises a selectable marker.

13. A method of reducing gene expression from a trisomic human chromosome 13, 18, or 21 or mouse chromosome 16 in a cell, the method comprising:

providing a cell comprising a trisomic human chromosome 13, 18, or 21 or mouse chromosome 16; and introducing into the cell (i) a vector comprising a nucleic acid construct comprising:

a silencing sequence encoding an Xist RNA; and first and second sequences that direct insertion of the silencing sequence into human chromosome 13, 18, or 21 or mouse chromosome 16; and (ii) a nucleic acid encoding a chimeric zinc finger nuclease (ZFN), or a ZFN polypeptide, that targets the human chromosome 13, 18, or 21 or mouse chromosome 16, in an amount sufficient to reduce gene expression from the trisomic chromosome.

* * * * *

UNITED STATES PATENT AND TRADEMARK OFFICE

CERTIFICATE OF CORRECTION

PATENT NO. : 8,212,019 B2
APPLICATION NO. : 12/512964
DATED : July 3, 2012
INVENTOR(S) : Jeanne B. Lawrence and Lisa L. Hall It is certified that error appears in the above-identified patent and that said Letters Patent is hereby corrected as shown below:

Title page, Item (56) (other publications), line 7:
delete “ai.” and replace with --al.--.

Title page, Item (56) (other publications), line 13:
delete “PCT/US209/” and replace with --PCT/US2009/--.

Replace the paragraph beginning at page 22, column 1, line 14, with the following amended paragraph:
This invention was made with government support awarded by the National Institutes of Health under Grant Nos. ~~R01GM53234 and T32HD07439~~ GM053234, HD007439, and GM068138. The government has certain rights in this invention.

Signed and Sealed this
Eleventh Day of September, 2012

David J. Kappos
*Director of the United States Patent and Trademark Office*

UNITED STATES PATENT AND TRADEMARK OFFICE

CERTIFICATE OF CORRECTION

PATENT NO. : 8,212,019 B2
APPLICATION NO. : 12/512964
DATED : July 3, 2012
INVENTOR(S) : Jeanne B. Lawrence and Lisa L. Hall It is certified that error appears in the above-identified patent and that said Letters Patent is hereby corrected as shown below:

On the Title page, Item (56) References Cited, column 2, line 11, delete "o fan" and replace with -- of an --.

In the Specification

Column 1, line 16, delete "R01GM53234 and T32HD0739" and replace with -- GM053234, GM068138, HD007439, and GM096400 --.

Signed and Sealed this
Eighteenth Day of March, 2014

Michelle K. Lee
*Deputy Director of the United States Patent and Trademark Office*